(12) United States Patent
Gillespie et al.

(10) Patent No.: US 7,645,773 B2
(45) Date of Patent: Jan. 12, 2010

(54) THIAZOLES AS INHIBITORS OF 11β-HYDROXYSTEROID DEHYDROGENASE

(75) Inventors: Paul Gillespie, Westfield, NJ (US); Robert Alan Goodnow, Jr., Gillette, NJ (US); Agnieszka Kowalczyk, Mine Hill, NJ (US); Kang Le, Green Brook, NJ (US); Qiang Zhang, Parsippany, NJ (US)

(73) Assignee: Hoffmann-La Roche Inc., Nutley, NJ (US)

( * ) Notice: Subject to any disclaimer, the term of this patent is extended or adjusted under 35 U.S.C. 154(b) by 35 days.

(21) Appl. No.: 11/650,645

(22) Filed: Jan. 8, 2007

(65) Prior Publication Data

US 2007/0167622 A1     Jul. 19, 2007

Related U.S. Application Data

(60) Provisional application No. 60/759,676, filed on Jan. 18, 2006.

(51) Int. Cl.
*A61K 31/4709*   (2006.01)
*A61K 31/427*    (2006.01)
*C07D 403/02*    (2006.01)
*C07D 215/00*    (2006.01)
*C07D 277/20*    (2006.01)

(52) U.S. Cl. .................. 514/311; 514/365; 540/480; 546/152; 548/202

(58) Field of Classification Search .............. 548/200, 548/146, 202; 540/480; 546/152; 514/311, 514/365
See application file for complete search history.

(56) References Cited

U.S. PATENT DOCUMENTS

| 4,260,765 | A | 4/1981 | Harrison et al. |
| 5,244,867 | A | 9/1993 | Ditrich et al. |
| 5,256,633 | A | 10/1993 | Ditrich et al. |
| 5,284,821 | A | 2/1994 | Ditrich et al. |
| 2003/0198965 | A1 | 10/2003 | Freier |
| 2004/0122033 | A1 | 6/2004 | Nargund et al. |
| 2004/0133011 | A1 | 7/2004 | Waddell et al. |
| 2005/0137209 | A1 | 6/2005 | Oksenberg et al. |
| 2005/0245532 | A1 | 11/2005 | Hoff et al. |
| 2005/0245745 | A1 | 11/2005 | Link et al. |

FOREIGN PATENT DOCUMENTS

| EP | 0 419 944 A2 | 4/1991 |
| JP | 09221476 | 8/1997 |
| JP | 2002201193 | 7/2002 |
| WO | WO9534540 | 12/1995 |
| WO | WO 96/22294 A1 | 7/1996 |
| WO | WO9839325 | 9/1998 |
| WO | WO0177101 | 10/2001 |
| WO | WO0190090 | 11/2001 |
| WO | WO0190091 | 11/2001 |
| WO | WO0190092 | 11/2001 |
| WO | WO0190093 | 11/2001 |
| WO | WO0190094 | 11/2001 |
| WO | WO02076435 A2 | 10/2002 |
| WO | WO02085899 | 10/2002 |
| WO | WO 03/027085 A2 | 4/2003 |
| WO | WO03043999 | 5/2003 |
| WO | WO03044000 | 5/2003 |
| WO | WO03044009 | 5/2003 |
| WO | WO03059267 | 7/2003 |
| WO | WO2004011410 | 7/2003 |
| WO | WO03065983 | 8/2003 |
| WO | WO03068242 | 8/2003 |
| WO | WO03075660 | 9/2003 |
| WO | WO03088917 | 10/2003 |
| WO | WO03090680 | 11/2003 |
| WO | WO03099821 | 12/2003 |
| WO | WO03104207 | 12/2003 |
| WO | WO03104208 | 12/2003 |
| WO | WO2004007501 | 1/2004 |
| WO | WO2004033427 | 4/2004 |
| WO | WO2004041264 | 5/2004 |
| WO | WO2004058741 | 7/2004 |
| WO | WO2004065351 | 8/2004 |
| WO | WO2004089415 | 10/2004 |
| WO | WO2004089416 | 10/2004 |
| WO | WO2004089470 | 10/2004 |
| WO | WO2004089471 | 10/2004 |
| WO | WO2004089896 | 10/2004 |
| WO | WO2004103980 | 12/2004 |

(Continued)

OTHER PUBLICATIONS

"Acid Lipase." Retrieved online via Internet [Feb. 6, 2008] URL: http://www.ninds.nih.gov/disorders/acid_lipase/acid_lipase.htm.*

(Continued)

*Primary Examiner*—Kamal A Saeed
*Assistant Examiner*—Samantha L Shterengarts
(74) *Attorney, Agent, or Firm*—George W. Johnston; Dennis P. Tramaloni; Samuel H. Megerditchian

(57) ABSTRACT

Provided herein are compounds of the formula (I):

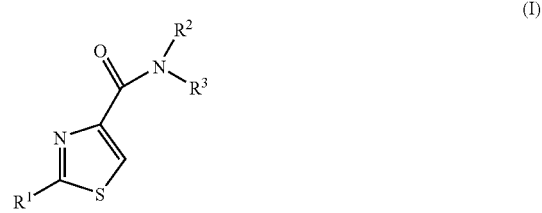

as well as pharmaceutically acceptable salts thereof, wherein the substituents are as those disclosed in the specification. These compounds, and the pharmaceutical compositions containing them, are useful for the treatment of diseases such as, for example, type II diabetes mellitus and metabolic syndrome.

17 Claims, No Drawings

FOREIGN PATENT DOCUMENTS

| WO | WO2004106294 |    | 12/2004 |
| --- | --- | --- | --- |
| WO | WO2004112781 |    | 12/2004 |
| WO | WO2004112782 |    | 12/2004 |
| WO | WO2005016877 |    | 2/2005 |
| WO | WO2005035534 | A1 | 4/2005 |
| WO | WO2005042513 | A1 | 5/2005 |
| WO | WO2005044192 |    | 5/2005 |
| WO | WO2005046685 | A1 | 5/2005 |
| WO | WO2005047250 | A1 | 5/2005 |
| WO | WO2005060963 | A1 | 7/2005 |
| WO | WO2005063247 |    | 7/2005 |
| WO | WO2005073200 |    | 8/2005 |
| WO | WO2005075471 |    | 8/2005 |
| WO | WO2005095350 | A1 | 10/2005 |
| WO | WO2005097759 |    | 10/2005 |
| WO | WO2005097764 |    | 10/2005 |
| WO | WO 2005/103050 | A2 | 11/2005 |
| WO | WO2005103023 | A1 | 11/2005 |
| WO | WO2005110992 | A1 | 11/2005 |
| WO | WO2005116002 |    | 12/2005 |
| WO | WO 2006/127587 | A1 | 11/2006 |

OTHER PUBLICATIONS

"Barth." Retrieved online via Internet [Feb. 6, 2008] URL: http://www.ninds.nih.gov/disorders/barth/barth.htm.*
"Gangliosidoses." Retrieved online via Internet [Feb. 6, 2008] URL: http://www.ninds.nih.gov/disorders/gangliosidoses/Gangliosidoses.htm.*
"Pompe." Retrieved online via Internet [Feb. 6, 2008] URL: http://www.ninds.nih.gov/disorders/pompe/pompe.htm.*
"Farber's." Retrieved online via Internet [Feb. 6, 2008] URL: http://www.ninds.nih.gov/disorders/Farbers/farbers.htm.*
De Fronzo, R. A. Drugs 1999, 58 Suppl. 1, 29.
Inzucchi, S. E. JAMA 2002, 287, 360.
Turner, R. C. et al. JAMA 1999, 281, 2005.
Tadayyon, M. and Smith, S.A. Expert Opin. Investig. Drugs 2003, 12, 307.
Salas, M. and Caro, J. J. Adv. Drug React. Tox. Rev. 2002, 21, 205-217.
E. S. Ford et al. JAMA 2002, 287, 356.
Y. Kotolevtsev et al. Proc. Natl. Acad. Sci. USA 1997, 94, 14924.
N. M. Morton et al. J. Biol. Chem. 2001, 276, 41293.
H. Masuzaki et al. Science, 2001, 294, 2166.
B. R. Walker et al. J. Clin. Endocrinol. Metab. 1995, 80, 3155.
R. C. Andrews et al. J. Clin. Endocrinol. Metab. 2003, 88, 285.
T. C. Sandeep et al. Proc. Natl. Acad. Sci USA 2004, 101, 6734.
S. Diederich, et. al., Eur. J. Endocrinol. 2000, 142, 200.
R.A.S. Schweizer, et. al., Mol. Cell. Endocrinol. 2003, 212, 41.
J. Exp. Chem. 2005, 202, 517-527.
J. Endocrinol. Invest., 2004, 27, 969-974.
Sycheva, T.P., et al., Chemical Abstracts (1964), XP002442436 & Zhurnal Obshchei Khimii, 33, (11), pp. 3659-3661 (1963).
T. Ross Kelly et al., Tetrahedron Letters, vol. 32, No. 34, pp. 4263-4266 (1991), XP002442370.
Golo Heckmann and Thorsten Bach, Angewandte Chemie, vol. 117, pp. 1223-1226 (2005), XP002442371.
S. Richard Baker, et al., Bioorganic & Medicinal Chemistry Letters, vol. 15, pp. 4727-4730 (2005), XP002442372.
Chemical Abstracts Service (2004), XP002442437.
Roberto Fatturusso, et al., J. Med. Chem., vol. 48, pp. 1649-1656 (2005), XP002442373.

* cited by examiner

THIAZOLES AS INHIBITORS OF 11β-HYDROXYSTEROID DEHYDROGENASE

PRIORITY TO RELATED APPLICATIONS

This application claims the benefit of U.S. Provisional Application No. 60/759,676, filed Jan. 18, 2006, which is hereby incorporated by reference in its entirety.

FIELD OF THE INVENTION

The invention relates to inhibitors of 11β-hydroxysteroid dehydrogenase. The inhibitors include, for example, thiazoles and derivatives thereof and are useful for the treatment of diseases such as type II diabetes mellitus and metabolic syndrome.

All documents cited or relied upon below are expressly incorporated herein by reference.

BACKGROUND OF THE INVENTION

Diabetes mellitus is a serious illness that affects an increasing number of people across the world. Its incidence is escalating parallel to the trend of greater obesity in many countries. The serious consequences of the disease include increased risk of stroke, heart disease, kidney damage, blindness, and amputation. Diabetes is characterized by decreased insulin secretion and/or an impaired ability of peripheral tissues to respond to insulin, resulting in increased plasma glucose levels. There are two forms of diabetes: insulin-dependent and non-insulin-dependent, with the great majority of diabetics suffering from the non-insulin-dependent form of the disease, known as type 2 diabetes or non-insulin-dependent diabetes mellitus (NIDDM). Because of the serious consequences, there is an urgent need to control diabetes.

Treatment of NIDDM generally starts with weight loss, a healthy diet and an exercise program. These factors are especially important in addressing the increased cardiovascular risks associated with diabetes, but they are generally ineffective in controlling the disease itself. There are a number of drug treatments available, including insulin, metformin, sulfonylureas, acarbose, and thiazolidinediones. However, each of these treatments has disadvantages, and there is an ongoing need for new drugs to treat diabetes.

Metformin is an effective agent that reduces fasting plasma glucose levels and enhances the insulin sensitivity of peripheral tissue. Metformin has a number of effects in vivo, including an increase in the synthesis of glycogen, the polymeric form in which glucose is stored [De Fronzo, R. A. Drugs 1999, 58 Suppl. 1, 29]. Metformin also has beneficial effects on lipid profile, with favorable results on cardiovascular health—treatment with metformin leads to reductions in the levels of LDL cholesterol and triglycerides [Inzucchi, S. E. JAMA 2002, 287, 360]. However, over a period of years, metformin loses its effectiveness [Turner, R. C. et al. JAMA 1999, 281, 2005] and there is consequently a need for new treatments for diabetes.

Thiazolidinediones are activators of the nuclear receptor peroxisome-proliferator activated receptor-gamma. They are effective in reducing blood glucose levels, and their efficacy has been attributed primarily to decreasing insulin resistance in skeletal muscle [Tadayyon, M. and Smith, S. A. Expert Opin. Investig. Drugs 2003, 12, 307]. One disadvantage associated with the use of thiazolidinediones is weight gain.

Sulfonylureas bind to the sulfonylurea receptor on pancreatic beta cells, stimulate insulin secretion, and consequently reduce blood glucose levels. Weight gain is also associated with the use of sulfonylureas [Inzucchi, S. E. JAMA 2002, 287, 360] and, like metformin, they lose efficacy over time [Turner, R. C. et al. JAMA 1999, 281, 2005]. A further problem often encountered in patients treated with sulfonylureas is hypoglycemia [Salas, M. and Caro, J. J. Adv. Drug React. Tox. Rev. 2002, 21, 205-217].

Acarbose is an inhibitor of the enzyme alpha-glucosidase, which breaks down disaccharides and complex carbohydrates in the intestine. It has lower efficacy than metformin or the sulfonylureas, and it causes intestinal discomfort and diarrhea which often lead to the discontinuation of its use [Inzucchi, S. E. JAMA 2002, 287, 360]

Because none of these treatments is effective over the long term without serious side effects, there is a need for new drugs for the treatment of type 2 diabetes.

The metabolic syndrome is a condition where patients exhibit more than two of the following symptoms: obesity, hypertriglyceridemia, low levels of HDL-cholesterol, high blood pressure, and elevated fasting glucose levels. This syndrome is often a precursor of type 2 diabetes, and has high prevalence in the United States estimated at 24% (E. S. Ford et al. JAMA 2002, 287, 356). A therapeutic agent that ameliorates the metabolic syndrome would be useful in potentially slowing or stopping the progression to type 2 diabetes.

In the liver, glucose is produced by two different processes. The first is gluconeogenesis, where new glucose is generated in a series of enzymatic reactions from pyruvate; and the second is glycolysis, where glucose is generated by the breakdown of the polymer glycogen.

Two of the key enzymes in the process of gluconeogenesis are phosphoenolpyruvate carboxykinase (PEPCK) which catalyzes the conversion of oxalacetate to phosphoenolpyruvate, and glucose-6-phosphatase (G6Pase) which catalyzes the hydrolysis of glucose-6-phosphate to give free glucose. The conversion of oxalacetate to phosphoenolpyruvate, catalyzed by PEPCK, is the rate-limiting step in gluconeogenesis. On fasting, both PEPCK and G6Pase are upregulated, allowing the rate of gluconeogenesis to increase. The levels of these enzymes are controlled in part by the corticosteroid hormones (cortisol in human and corticosterone in mouse). When the corticosteroid binds to the corticosteroid receptor, a signaling cascade is triggered which results in the upregulation of these enzymes.

The corticosteroid hormones are found in the body along with their oxidized 11-dehydro counterparts (cortisone and 11-dehydrocorticosterone in human and mouse, respectively), which do not have activity at the glucocorticoid receptor. The actions of the hormone depend on the local concentration in the tissue where the corticosteroid receptors are expressed. This local concentration can differ from the circulating levels of the hormone in plasma, because of the actions of redox enzymes in the tissues. The enzymes that modify the oxidation state of the hormones are 11beta-hydroxysteroid dehydrogenases forms I and II. Form I (11β-HSD1) is responsible for the reduction of cortisone to cortisol in vivo, while form II (11β-HSD2) is responsible for the oxidation of cortisol to cortisone. The enzymes have low homology and are expressed in different tissues. 11β-HSD1 is highly expressed in a number of tissues including liver, adipose tissue, and brain, while 11β-HSD2 is highly expressed in mineralocorticoid target tissues, such as kidney and colon. 11β-HSD2 prevents the binding of cortisol to the mineralocorticoid receptor, and defects in this enzyme have been found to be associated with the syndrome of apparent mineralocorticoid excess (AME).

Since the binding of the 11β-hydroxysteroids to the corticosteroid receptor leads to upregulation of PEPCK and therefore to increased blood glucose levels, inhibition of 11β-HSD1 is a promising approach for the treatment of diabetes. In addition to the biochemical discussion above, there is evidence from transgenic mice, and also from small clinical studies in humans, that confirm the therapeutic potential of the inhibition of 11β-HSD1.

Experiments with transgenic mice indicate that modulation of the activity of 11β-HSD1 could have beneficial therapeutic effects in diabetes and in the metabolic syndrome. For example, when the 11β-HSD1 gene is knocked out in mice, fasting does not lead to the normal increase in levels of G6Pase and PEPCK, and the animals are not susceptible to stress- or obesity-related hyperglycemia. Moreover, knockout animals which are rendered obese on a high-fat diet have significantly lower fasting glucose levels than weight-matched controls (Y. Kotolevtsev et al. Proc. Natl. Acad. Sci. USA 1997, 94, 14924). 11β-HSD1 knockout mice have also been found to have improved lipid profile, insulin sensitivity, and glucose tolerance (N. M. Morton et al. J. Biol. Chem. 2001, 276, 41293). The effect of overexpressing the 11β-HSD1 gene in mice has also been studied. These transgenic mice displayed increased 11β-HSD1 activity in adipose tissue, and they also exhibit visceral obesity which is associated with the metabolic syndrome. Levels of the corticosterone were increased in adipose tissue, but not in serum, and the mice had increased levels of obesity, especially when on a high-fat diet. Mice fed on low-fat diets were hyperglycemic and hyperinsulinemic, and also showed glucose intolerance and insulin resistance (H. Masuzaki et al. Science, 2001, 294, 2166).

The effects of the non-selective 11β-hydroxysteroid dehydrogenase inhibitor carbenoxolone have been studied in a number of small trials in humans. In one study, carbenoxolone was found to lead to an increase in whole body insulin sensitivity, and this increase was attributed to a decrease in hepatic glucose production (B. R. Walker et al. J. Clin. Endocrinol. Metab. 1995, 80, 3155). In another study, decreased glucose production and glycogenolysis in response to glucagon challenge were observed in diabetic but not healthy subjects (R. C. Andrews et al. J. Clin. Endocrinol. Metab. 2003, 88, 285). Finally, carbenoxolone was found to improve cognitive function in healthy elderly men and also in type 2 diabetics (T. C. Sandeep et al. Proc. Natl. Acad. Sci USA 2004, 101, 6734).

A need exists in the art, therefore, for 11β-HSD1 inhibitors that have efficacy for the treatment of diseases such as, for example, type II diabetes mellitus and metabolic syndrome. Further, a need exists in the art for 11β-HSD1 inhibitors having IC50 values less than about 1 μM.

SUMMARY OF THE INVENTION

In one embodiment of the present invention, provided is a compound of the formula (I):

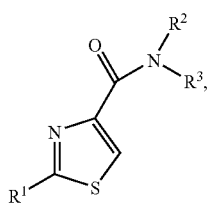

(I)

wherein:

$R^1$ is 5- to 8-membered cycloalkyl,
  phenyl, unsubstituted or mono-, bi-, or tri-substituted independently with halogen, lower alkyl, halo-lower-alkyl, phenyl, —OCH$_3$, —O(CH$_2$)nCH$_3$, —(CH$_2$)nOH, —OH, —NH$_2$, —OCF$_3$, —O(CH$_2$)n-phenyl, —SCH$_3$, —NHSO$_2$CH$_3$, thiophene, morpholine, —C(O)CH$_3$, —N(CH$_3$)$_2$ or —NO$_2$,
  5- or 6-membered saturated, partially unsaturated, or aryl ring which is connected by a ring carbon atom and which has from 1 to 3 hetero ring atoms selected from the group consisting of sulfur, nitrogen and oxygen, unsubstituted or substituted with halogen, lower alkoxy, or lower alkyl,
  9- or 10-membered bicyclic unsaturated or partially unsaturated ring which is connected by a ring carbon and which has from 1 to 3 hetero ring atoms selected from the group consisting of sulfur, nitrogen and oxygen, unsubstituted or mono-, bi- or tri-substituted with halogen or lower alkyl;

one of $R^2$ or $R^3$ is H or branched or unbranched lower alkyl, and the other is $C_4$-$C_{10}$ alkyl, —CH$_2$-phenyl, mono-, bi- or tri-cyclic 5- to 10-membered carbocyclic ring unsubstituted or mono- or bi-substituted with lower alkyl, hydroxy, or oxo, or bicyclic partially unsaturated 9- or 10-membered ring, or $R^2$ and $R^3$, together with the N atom to which they are attached, form a saturated or partially unsaturated 6- to 8-membered monocyclic or 7- to 10-membered bicyclic ring, which contains the N atom to which $R_2$ and $R_3$ are attached, and optionally another hetero atom which is selected from O and S, unsubstituted or mono- or bi-substituted with branched or unbranched lower alkyl, halogen, hydroxy, hydroxy-alkyl, pyridine, carboxy, phenyl, oxo, —CH$_2$-phenyl or 5- to 10-membered cycloalkyl; and n is zero, 1 or 2, or a pharmaceutically acceptable salt thereof, with the proviso that the following compounds are excluded:

[2-(2,3-Dihydro-benzo[1,4]dioxin-2-yl)-thiazol-4-yl]-pyrrolidin-1-yl-methanone;

[2-(2,3-Dihydro-benzo[1,4]dioxin-2-yl)-thiazol-4-yl]-morpholin-4-yl-methanone;

(4-Phenyl-3,6-dihydro-2H-pyridin-1-yl)-(2-phenyl-thiazol-4-yl)-methanone;

(2-Benzo[1,2,5]oxadiazol-5-yl-thiazol-4-yl)-morpholin-4-yl-methanone;

Morpholin-4-yl-(2-pyridin-3-yl-thiazol-4-yl)-methanone;

[2-(4-Methyl-pyridin-3-yl)-thiazol-4-yl]-piperidin-1-yl-methanone;

[2-(4-Methyl-pyridin-3-yl)-thiazol-4-yl]-morpholin-4-yl-methanone;

[2-(5-Methyl-isoxazol-3-yl)-thiazol-4-yl]-piperidin-1-yl-methanone; and

[2-(3-Methyl-5-trifluoromethyl-pyrazol-1-yl)-thiazol-4-yl]-morpholin-4-yl-methanone.

In another embodiment of the present invention, provided is a pharmaceutical composition, comprising a therapeutically effective amount of a compound of the formula (I):

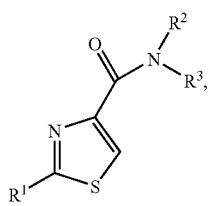

(I)

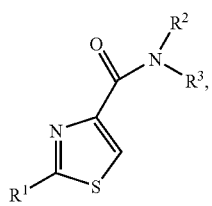

(I)

wherein:

R¹ is 5- to 8-membered cycloalkyl,
  phenyl, unsubstituted or mono-, bi-, or tri-substituted independently with halogen, lower alkyl, halo-lower-alkyl, phenyl, —OCH₃, —O(CH₂)nCH₃, —(CH₂)nOH, —OH, —NH₂, —OCF₃, —O(CH₂)n-phenyl, —SCH₃, —NHSO₂CH₃, thiophene, morpholine, —C(O)CH₃, —N(CH₃)₂ or —NO₂,
  5- or 6-membered saturated, partially unsaturated, or aryl ring which is connected by a ring carbon atom and which has from 1 to 3 hetero ring atoms selected from the group consisting of sulfur, nitrogen and oxygen, unsubstituted or substituted with halogen, lower alkoxy, or lower alkyl,
  9- or 10-membered bicyclic unsaturated or partially unsaturated ring which is connected by a ring carbon and which has from 1 to 3 hetero ring atoms selected from the group consisting of sulfur, nitrogen and oxygen, unsubstituted or mono-, bi- or tri-substituted with halogen or lower alkyl;
one of R² or R³ is H or branched or unbranched lower alkyl, and the other is C₄-C₁₀ alkyl, —CH₂-phenyl, mono-, bi- or tri-cyclic 5- to 10-membered carbocyclic ring unsubstituted or mono- or bi-substituted with lower alkyl, hydroxy, or oxo, or bicyclic partially unsaturated 9- or 10-membered ring, or R² and R³, together with the N atom to which they are attached, form a saturated or partially unsaturated 6- to 8-membered monocyclic or 7- to 10-membered bicyclic ring, which contains the N atom to which R₂ and R₃ are attached, and optionally another hetero atom which is selected from O and S, unsubstituted or mono- or bi-substituted with branched or unbranched lower alkyl, halogen, hydroxy, hydroxy-alkyl, pyridine, carboxy, phenyl, oxo, —CH₂-phenyl or 5- to 10-membered cycloalkyl; and n is zero, 1 or 2, or a pharmaceutically acceptable salt thereof, and a pharmaceutically acceptable carrier.

In a further embodiment of the present invention, provided is a method for treating a metabolic disease or disorder, comprising the step of administering to a patient in need thereof a therapeutically effective amount of a compound of the formula (I):

wherein:

R¹ is 5- to 8-membered cycloalkyl,
  phenyl, unsubstituted or mono-, bi-, or tri-substituted independently with halogen, lower alkyl, halo-lower-alkyl, phenyl, —OCH₃, —O(CH₂)nCH₃, —(CH₂)nOH, —OH, —NH₂, —OCF₃, —O(CH₂)n-phenyl, —SCH₃, —NHSO₂CH₃, thiophene, morpholine, —C(O)CH₃, —N(CH₃)₂ or —NO₂,
  5- or 6-membered saturated, partially unsaturated, or aryl ring which is connected by a ring carbon atom and which has from 1 to 3 hetero ring atoms selected from the group consisting of sulfur, nitrogen and oxygen, unsubstituted or substituted with halogen, lower alkoxy, or lower alkyl,
  9- or 10-membered bicyclic unsaturated or partially unsaturated ring which is connected by a ring carbon and which has from 1 to 3 hetero ring atoms selected from the group consisting of sulfur, nitrogen and oxygen, unsubstituted or mono-, bi- or tri-substituted with halogen or lower alkyl;
one of R² or R³ is H or branched or unbranched lower alkyl, and the other is C₄-C₁₀ alkyl, —CH₂-phenyl, mono-, bi- or tri-cyclic 5- to 10-membered carbocyclic ring unsubstituted or mono- or bi-substituted with lower alkyl, hydroxy, or oxo, or bicyclic partially unsaturated 9- or 10-membered ring, or R² and R³, together with the N atom to which they are attached, form a saturated or partially unsaturated 6- to 8-membered monocyclic or 7- to 10-membered bicyclic ring, which contains the N atom to which R₂ and R₃ are attached, and optionally another hetero atom which is selected from O and S, unsubstituted or mono- or bi-substituted with branched or unbranched lower alkyl, halogen, hydroxy, hydroxy-alkyl, pyridine, carboxy, phenyl, oxo, —CH₂-phenyl or 5- to 10-membered cycloalkyl; and n is zero, 1 or 2, or a pharmaceutically acceptable salt thereof.

DETAILED DESCRIPTION

The present invention is directed to inhibitors of 11β-HSD1. In a preferred embodiment, the invention provides for pharmaceutical compositions comprising thiazoles of the formula (I):

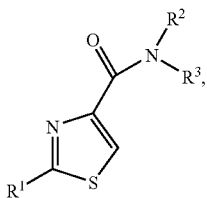

as well as pharmaceutically acceptable salts thereof, that are useful as inhibitors of 11β-HSD1.

It is to be understood that the terminology employed herein is for the purpose of describing particular embodiments, and is not intended to be limiting. Further, although any methods, devices and materials similar or equivalent to those described herein can be used in the practice or testing of the invention, the preferred methods, devices and materials are now described.

As used herein, the term "alkyl" means, for example, a branched or unbranched, cyclic ("cycloalkyl") or acyclic, saturated or unsaturated (e.g. alkenyl or alkynyl) hydrocarbyl radical which may be substituted or unsubstituted. Where cyclic, the alkyl group is preferably $C_3$ to $C_{12}$, more preferably $C_4$ to $C_{10}$, more preferably $C_4$ to $C_7$. Where acyclic, the alkyl group is preferably $C_1$ to $C_{10}$, more preferably $C_1$ to $C_6$, more preferably methyl, ethyl, propyl (n-propyl or isopropyl), butyl (n-butyl, isobutyl or tertiary-butyl) or pentyl (including n-pentyl and isopentyl), more preferably methyl. It will be appreciated therefore that the term "alkyl" as used herein includes alkyl (branched or unbranched), substituted alkyl (branched or unbranched), alkenyl (branched or unbranched), substituted alkenyl (branched or unbranched), alkynyl (branched or unbranched), substituted alkynyl (branched or unbranched), cycloalkyl, substituted cycloalkyl, cycloalkenyl, substituted cycloalkenyl, cycloalkynyl and substituted cycloalkynyl. A preferred example of cycloalkyl includes cycloalkenyl.

As used herein, the term "lower alkyl" means, for example, a branched or unbranched, cyclic or acyclic, saturated or unsaturated (e.g. alkenyl or alkynyl) hydrocarbyl radical wherein said cyclic lower alkyl group is $C_5$, $C_6$ or $C_7$, and wherein said acyclic lower alkyl group is $C_1$, $C_2$, $C_3$ or $C_4$, and is preferably selected from methyl, ethyl, propyl (n-propyl or isopropyl) or butyl (n-butyl, isobutyl or tertiary-butyl). It will be appreciated therefore that the term "lower alkyl" as used herein includes, for example, lower alkyl (branched or unbranched), lower alkenyl (branched or unbranched), lower alkynyl (branched or unbranched), cycloloweralkyl, cycloloweralkenyl and cycloloweralkynyl.

As used herein, the term "aryl" means, for example, a substituted or unsubstituted carbocyclic aromatic group, such as phenyl or naphthyl, or a substituted or unsubstituted heteroaromatic group containing one or more, preferably one, heteroatom, such as pyridyl, pyrrolyl, furanyl, thienyl, thiazolyl, isothiazolyl, oxazolyl, isoxazolyl, oxadiazolyl, thiadiazolyl pyrazolyl, imidazolyl, triazolyl, pyrimidinyl pyridazinyl, pyrazinyl, triazinyl, indolyl, indazolyl, quinolyl, quinazolyl, benzimidazolyl, benzothiazolyl, benzisoxazolyl and benzisothiazolyl. In a preferred embodiment, the term "heteroaryl", alone or combination with other groups, means a monocyclic or bicyclic radical of 5 to 12 ring atoms having at least one aromatic ring containing one, two, or three ring heteroatoms selected from N, O, and S, the remaining ring atoms being C. One or two ring carbon atoms of the heteroaryl group may be replaced with a carbonyl group. The heteroaryl group may be substituted independently with one, two, or three substituents, preferably one or two substituents. Such substituents include, for example, halogen, hydroxy, $C_{1-6}$ alkyl, halo $C_{1-6}$ alkyl, $C_{1-6}$ alkoxy, $C_{1-6}$ alkyl sulfonyl, $C_{1-6}$ alkyl sulfinyl, $C_{1-6}$ alkylthio, amino, amino $C_{1-6}$ alkyl, mono- or di-substituted amino-$C_{1-6}$ alkyl, nitro, cyano, acyl, carbamoyl, mono- or di-substituted amino, aminocarbonyl, mono- or di-substituted amino-carbonyl, aminocarbonyl $C_{1-6}$ alkoxy, mono- or di-substituted amino-carbonyl-$C_{1-6}$ alkoxy, hydroxy-$C_{1-6}$ alkyl, carboxyl, $C_{1-6}$ alkoxy carbonyl, aryl $C_{1-6}$ alkoxy, heteroaryl $C_{1-6}$ alkoxy, heterocyclyl $C_{1-6}$ alkoxy, $C_{1-6}$ alkoxycarbonyl $C_{1-6}$ alkoxy, carbamoyl $C_{1-6}$ alkoxy and carboxyl $C_{1-6}$ alkoxy, preferably selected from the group consisting of halogen, hydroxy, $C_{1-6}$ alkyl, halo $C_{1-6}$ alkyl, $C_{1-6}$ alkoxy, $C_{1-6}$ alkyl sulfonyl, $C_{1-6}$ alkyl sulfinyl, $C_{1-6}$ alkylthio, amino, mono-$C_{1-6}$ alkyl substituted amino, di-$C_{1-6}$ alkyl substituted amino, amino $C_{1-6}$ alkyl, mono-$C_{1-6}$ alkyl substituted amino-$C_{1-6}$ alkyl, di-$C_{1-6}$ alkyl substituted amino-$C_{1-6}$ alkyl, nitro, carbamoyl, mono- or di-substituted amino-carbonyl, hydroxy-$C_{1-6}$ alkyl, carboxyl, $C_{1-6}$ alkoxy carbonyl and cyano.

The alkyl and aryl groups may be substituted or unsubstituted. Where substituted, there will generally be, for example, 1 to 3 substituents present, preferably 1 substituent. Substituents may include, for example: carbon-containing groups such as alkyl, aryl, arylalkyl (e.g. substituted and unsubstituted phenyl, substituted and unsubstituted benzyl); halogen atoms and halogen-containing groups such as haloalkyl (e.g. trifluoromethyl); oxygen-containing groups such as alcohols (e.g. hydroxyl, hydroxyalkyl, aryl(hydroxyl)alkyl), ethers (e.g. alkoxy, aryloxy, alkoxyalkyl, aryloxyalkyl), aldehydes (e.g. carboxaldehyde), ketones (e.g. alkylcarbonyl, alkylcarbonylalkyl, arylcarbonyl, arylalkylcarbonyl, arycarbonylalkyl), acids (e.g. carboxy, carboxyalkyl), acid derivatives such as esters(e.g. alkoxycarbonyl, alkoxycarbonylalkyl, alkylcarbonyloxy, alkylcarbonyloxyalkyl), amides (e.g. aminocarbonyl, mono- or di-alkylaminocarbonyl, aminocarbonylalkyl, mono-or di-alkylaminocarbonylalkyl, arylaminocarbonyl), carbamates (e.g. alkoxycarbonylamino, arloxycarbonylamino, aminocarbonyloxy, mono-or di-alkylaminocarbonyloxy, arylminocarbonloxy) and ureas (e.g. mono- or di-alkylaminocarbonylamino or arylaminocarbonylamino); nitrogen-containing groups such as amines (e.g. amino, mono- or di-alkylamino, aminoalkyl, mono- or di-alkylaminoalkyl), azides, nitriles (e.g. cyano, cyanoalkyl), nitro; sulfur-containing groups such as thiols, thioethers, sulfoxides and sulfones (e.g. alkylthio, alkylsulfinyl, alkylsulfonyl, alkylthioalkyl, alkylsulfinylalkyl, alkylsulfonylalkyl, arylthio, arysulfinyl, arysulfonyl, arythioalkyl, arylsulfinylalkyl, arylsulfonylalkyl); and heterocyclic groups containing one or more, preferably one, heteroatom, (e.g. thienyl, furanyl, pyrrolyl, imidazolyl, pyrazolyl, thiazolyl, isothiazolyl, oxazolyl, oxadiazolyl, thiadiazolyl, aziridinyl, azetidinyl, pyrrolidinyl, pyrrolinyl, imidazolidinyl, imidazolinyl, pyrazolidinyl, tetrahydrofuranyl, pyranyl, pyronyl, pyridyl, pyrazinyl, pyridazinyl, piperidyl, hexahydroazepinyl, piperazinyl, morpholinyl, thianaphthyl, benzofuranyl, isobenzofuranyl, indolyl, oxyindolyl, isoindolyl, indazolyl, indolinyl, 7-azaindolyl, benzopyranyl, coumarinyl, isocoumarinyl, quinolinyl, isoquinolinyl, naphthridinyl, cinnolinyl, quinazolinyl, pyridopyridyl, benzoxazinyl, quinoxalinyl, chromenyl, chromanyl, isochromanyl, phthalazinyl and carbolinyl).

The lower alkyl groups may be substituted or unsubstituted. Where substituted, there will generally be, for example, 1 to 3 substitutents present, preferably 1 substituent.

As used herein, the term "alkoxy" means, for example, alkyl-O— and "alkoyl" means, for example, alkyl-CO—. Alkoxy substituent groups or alkoxy-containing substituent groups may be substituted by, for example, one or more alkyl groups.

As used herein, the term "halogen" means, for example, a fluorine, chlorine, bromine or iodine radical, preferably a fluorine, chlorine or bromine radical, and more preferably a fluorine or chlorine radical.

"Pharmaceutically acceptable salt" refers to conventional acid-addition salts or base-addition salts that retain the biological effectiveness and properties of the compounds of formula I and are formed from suitable organic or inorganic acids or organic or inorganic bases. Sample acid-addition salts include those derived from inorganic acids such as hydrochloric acid, hydrobromic acid, hydroiodic acid, sulfuric acid, sulfamic acid, phosphoric acid and nitric acid, and those derived from organic acids such asp-toluenesulfonic acid, salicylic acid, methanesulfonic acid, oxalic acid, succinic acid, citric acid, malic acid, lactic acid, fumaric acid, and the like. Sample base-addition salts include those derived from ammonium, potassium, sodium and, quaternary ammonium hydroxides, such as for example, tetramethylammonium hydroxide. The chemical modification of a pharmaceutical compound (i.e. drug) into a salt is a well known technique which is used in attempting to improve properties involving physical or chemical stability, e.g., hygroscopicity, flowability or solubility of compounds. See, e.g., H. Ansel et. al., Pharmaceutical Dosage Forms and Drug Delivery Systems (6th Ed. 1995) at pp. 196 and 1456-1457.

"Pharmaceutically acceptable ester" refers to a conventionally esterified compound of formula I having a carboxyl group, which esters retain the biological effectiveness and properties of the compounds of formula I and are cleaved in vivo (in the organism) to the corresponding active carboxylic acid. Examples of ester groups which are cleaved (in this case hydrolyzed) in vivo to the corresponding carboxylic acids are those in which the hydrogen is replaced with lower alkyl which is optionally substituted, e.g., with heterocycle, cycloalkyl, etc. Examples of substituted lower alkyl esters are those in which lower alkyl is substituted with pyrrolidine, piperidine, morpholine, N-methylpiperazine, etc. The group which is cleaved in vivo may be, for example, ethyl, morpholino ethyl, and diethylamino ethyl. In connection with the present invention, —$CONH_2$ is also considered an ester, as the —$NH_2$ may be cleaved in vivo and replaced with a hydroxy group, to form the corresponding carboxylic acid.

Further information concerning examples of and the use of esters for the delivery of pharmaceutical compounds is available in Design of Prodrugs. Bundgaard H. ed. (Elsevier, 1985). See also, H. Ansel et. al., Pharmaceutical Dosage Forms and Drug Delivery Systems (6th Ed. 1995) at pp. 108-109; Krogsgaard-Larsen, et. al., Textbook of Drug Design and Development (2d Ed. 1996) at pp. 152-191.

In the practice of the method of the present invention, an effective amount of any one of the compounds of this invention or a combination of any of the compounds of this invention or a pharmaceutically acceptable salt or ester thereof, is administered via any of the usual and acceptable methods known in the art, either singly or in combination. The compounds or compositions can thus be administered orally (e.g., buccal cavity), sublingually, parenterally (e.g., intramuscularly, intravenously, or subcutaneously), rectally (e.g., by suppositories or washings), transdermally (e.g., skin electroporation) or by inhalation (e.g., by aerosol), and in the form or solid, liquid or gaseous dosages, including tablets and suspensions. The administration can be conducted in a single unit dosage form with continuous therapy or in a single dose therapy ad libitum. The therapeutic composition can also be in the form of an oil emulsion or dispersion in conjunction with a lipophilic salt such as pamoic acid, or in the form of a biodegradable sustained-release composition for subcutaneous or intramuscular administration.

Useful pharmaceutical carriers for the preparation of the compositions hereof, can be solids, liquids or gases; thus, the compositions can take the form of tablets, pills, capsules, suppositories, powders, enterically coated or other protected formulations (e.g. binding on ion-exchange resins or packaging in lipid-protein vesicles), sustained release formulations, solutions, suspensions, elixirs, aerosols, and the like. The carrier can be selected from the various oils including those of petroleum, animal, vegetable or synthetic origin, e.g., peanut oil, soybean oil, mineral oil, sesame oil, and the like. Water, saline, aqueous dextrose, and glycols are preferred liquid carriers, particularly (when isotonic with the blood) for injectable solutions. For example, formulations for intravenous administration comprise sterile aqueous solutions of the active ingredient(s) which are prepared by dissolving solid active ingredient(s) in water to produce an aqueous solution, and rendering the solution sterile. Suitable pharmaceutical excipients include starch, cellulose, glucose, lactose, talc, gelatin, malt, rice, flour, chalk, silica, magnesium stearate, sodium stearate, glycerol monostearate, sodium chloride, dried skim milk, glycerol, propylene glycol, water, ethanol, and the like. The compositions may be subjected to conventional pharmaceutical additives such as preservatives, stabilizing agents, wetting or emulsifying agents, salts for adjusting osmotic pressure, buffers and the like. Suitable pharmaceutical carriers and their formulation are described in Remington's Pharmaceutical Sciences by E. W. Martin. Such compositions will, in any event, contain an effective amount of the active compound together with a suitable carrier so as to prepare the proper dosage form for proper administration to the recipient.

The pharmaceutical preparations can also contain preserving agents, solubilizing agents, stabilizing agents, wetting agents, emulsifying agents, sweetening agents, coloring agents, flavoring agents, salts for varying the osmotic pressure, buffers, coating agents or antioxidants. They can also contain other therapeutically valuable substances, including additional active ingredients other than those of formula I.

The "therapeutically effective amount" or "dosage" of a compound according to this invention can vary within wide limits and may be determined in a manner known in the art. Such dosage will be adjusted to the individual requirements in each particular case including the specific compound(s) being administered, the route of administration, the condition being treated, as well as the patient being treated. In general, in the case of oral or parenteral administration to adult humans weighing approximately 70 kg, a daily dosage of from about 0.01 mg/kg to about 50 mg/kg should be appropriate, although the upper limit may be exceeded when indicated. The dosage is preferably from about 0.3 mg/kg to about 10 mg/kg per day. A preferred dosage may be from about 0.70 mg/kg to about 3.5 mg/kg per day. The daily dosage can be administered as a single dose or in divided doses, or for parenteral administration it may be given as continuous infusion.

The compounds of the present invention can be prepared by any conventional manner. Suitable processes for synthesizing these compounds are provided in the examples. Generally, compounds of formula I can be prepared according to the Schemes described below. The sources of the starting materials for these reactions are also described.

In the schemes below, the substituent at the 2-position of the thiazole ring is often drawn as a substituted phenyl moiety. It will be apparent to one of ordinary skill in the art that similar reactions are possible in the case of 2-heterocyclyl-thiazoles and in some cases, 2-alkyl-thiazoles. Drawing the structures with substituted phenyl substituents was useful for illustrative purposes, and does not limit the scope of the invention.

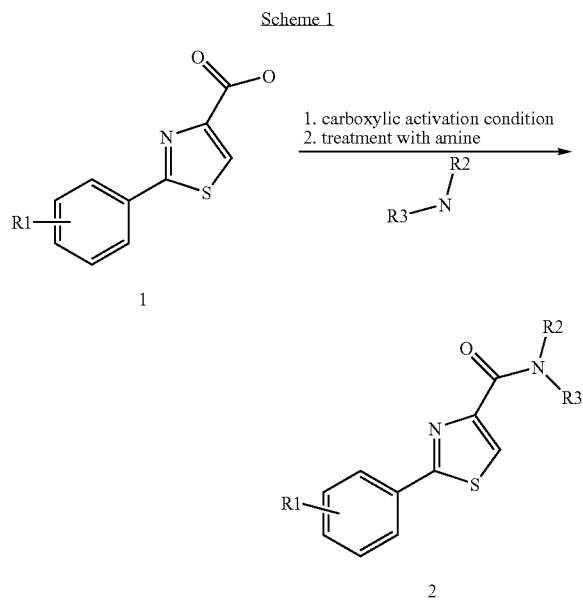

The coupling of carboxylic acids of structure 1 with amines of structure 2, according to Scheme 1, can be achieved using methods well known to one of ordinary skill in the art. For example, the transformation can be carried out by reaction of carboxylic acids of structure 1 or of appropriate derivatives thereof such as activated esters, with amines of diverse structure or their corresponding acid addition salts (e.g., the hydrochloride salts) in the presence, if necessary, of a coupling agent, many examples of which are well known per se in peptide chemistry. The reaction is conveniently carried out by treating the carboxylic acid of structure 1 with the hydrochloride of the reacting amine in the presence of an appropriate base, such as diisopropylethylamine, a coupling agent such as O-(benzotriazol-1-yl)-1,1,3,3-tetramethyluronium hexafluorophosphate, and in the optional additional presence of a substance that increases the rate of the reaction, such as 1-hydroxybenzotriazole or 1-hydroxy-7-azabenzotriazole, in an inert solvent, such as a chlorinated hydrocarbon (e.g., dichloromethane) or N,N-dimethylformamide or N-methylpyrrolidinone, at a temperature between about 0° C. and about room temperature, preferably at about room temperature. Alternatively, the reaction can be carried out by converting the carboxylic acid of formula 1 to an activated ester derivative, such as the N-hydroxysuccinimide ester, and subsequently reacting this with an amine or its corresponding acid addition salt. This reaction sequence can be carried out by reacting the carboxylic acid of formula 1 with N-hydroxysuccinimide in the presence of a coupling agent such as N,N'-dicyclohexylcarbodiimide in an inert solvent such as tetrahydrofuran at a temperature between about 0° C. and about room temperature. Alternatively, the N-hydroxysuccinimide ester can be prepared by reaction of commercially available 2-aryl-thiazole-5-carboxylic acids of formula 1 with TSTU (N,N,N',N'-Tetramethyl-O—(N-succinimidyl) uronium tetrafluoroborate, CAS #105832-38-0, available from Aldrich Chemical Company, Milwaukee, Wis.). The reaction is conveniently carried out in the presence of an organic base such as triethylamine or diisopropylethylamine. The reaction can be carried out in polar solvents such as mixtures of DMF and dioxane according to the solubility of the carboxylic acid. The reaction can be carried out at a temperature between about 0° C. and about room temperature, preferably at around room temperature. This chemistry can be carried out either in the synthesis of a single compound or in the synthesis of libraries of compounds using automated parallel synthesis methods.

Alternatively, compounds of formula 2 can be prepared by converting the carboxylic acid of formula 1 to the corresponding acyl halide, preferably the acid chloride, and then reacting this with an amine of formula HNR2R3, in the presence of base, preferably di-isopropylethyl amine, in an inert solvent such as dichloromethane or N,N-dimethylformamide. Acyl chlorides can be conveniently formed by reaction of carboxylic acids of structure 1 with chlorinating reagents, such as thionyl chloride or oxalyl chloride, preferably the latter, in dry dichloromethane at a temperature between about 0° C. and about room temperature.

Commercially available 2-aryl-thiazole-4-carboxylic acids include the following

| CAS # | Name |
|---|---|
| 368869-07-0 | 4-Thiazolecarboxylic acid, 2-(2,3-dihydro-5-benzofuranyl)- |
| 257876-07-6 | 4-Thiazolecarboxylic acid, 2-(2,3-dichlorophenyl)- |
| 255728-35-9 | 4-Thiazolecarboxylic acid, 2-[2-chloro-4-(trifluoromethyl)phenyl]- |
| 145293-20-5 | 4-Thiazolecarboxylic acid, 2-(4-aminophenyl)- |
| 144061-16-5 | 4-Thiazolecarboxylic acid, 2-[4-(trifluoromethyl)phenyl]- |
| 132307-22-3 | 4-Thiazolecarboxylic acid, 2-(3,4-dimethoxyphenyl)- |
| 115311-41-6 | 4-Thiazolecarboxylic acid, 2-(2-pyridinyl)- |
| 115311-40-5 | 4-Thiazolecarboxylic acid, 2-(2-aminophenyl)- |
| 115311-32-5 | 4-Thiazolecarboxylic acid, 2-[3-(trifluoromethyl)phenyl]- |
| 115311-25-6 | 4-Thiazolecarboxylic acid, 2-(2-methylphenyl)- |
| 115299-10-0 | 4-Thiazolecarboxylic acid, 2-(2-methoxyphenyl)- |
| 115299-07-5 | 4-Thiazolecarboxylic acid, 2-(3-methoxyphenyl)- |
| 113334-58-0 | 4-Thiazolecarboxylic acid, 2-(3-hydroxyphenyl)- |
| 57677-80-2 | 4-Thiazolecarboxylic acid, 2-(4-methoxyphenyl)- |
| 39067-29-3 | 4-Thiazolecarboxylic acid, 2-(3-pyridinyl)- |
| 36705-82-5 | 4-Thiazolecarboxylic acid, 2-(4-hydroxyphenyl)- |
| 27501-91-3 | 4-Thiazolecarboxylic acid, 2-(2-hydroxyphenyl)- |
| 21278-86-4 | 4-Thiazolecarboxylic acid, 2-(4-pyridinyl)- |
| 21160-50-9 | 4-Thiazolecarboxylic acid, 2-(4-bromophenyl)- |
| 17229-00-4 | 4-Thiazolecarboxylic acid, 2-(3-methylphenyl)- |
| 17228-99-8 | 4-Thiazolecarboxylic acid, 2-(4-methylphenyl)- |
| 17228-98-7 | 4-Thiazolecarboxylic acid, 2-(4-chlorophenyl)- |
| 17228-97-6 | 4-Thiazolecarboxylic acid, 2-(4-nitrophenyl)- |
| 7113-10-2 | 4-Thiazolecarboxylic acid, 2-phenyl- |

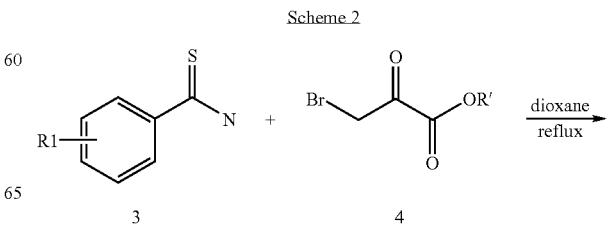

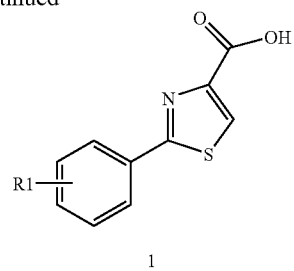

2-Aryl-thiazole-5-carboxylic acids of formula 1 can be prepared by treatment of substituted thiobenzamides (3) with 3-bromopyruvic acid (4, R'=H) in dioxane under reflux conditions as shown in Scheme 2. Compounds of formula 2 are then obtained by coupling the carboxylic acid of formula 1 with amines as described above.

Scheme 3

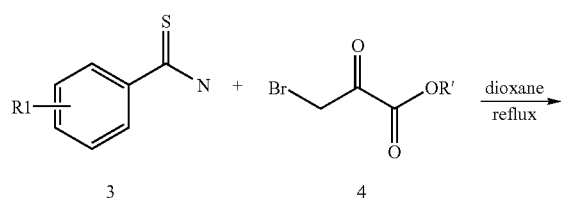

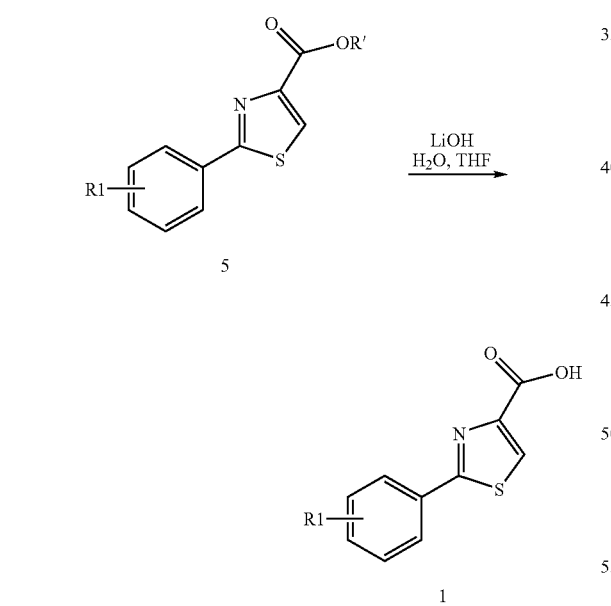

Alternatively, 2-aryl-thiazole-5-carboxylic acids of formula 1 can also be prepared by treatment of substituted thiobenzamides of formula 3 with ethyl 3-bromopyruvate (4, R'=Et) in dioxane under reflux conditions to form 2-aryl-thiazole-4-carboxylic acid ethyl esters (Scheme 3). The 2-aryl-thiazole-4-carboxylic acids are then formed by saponification of the ethyl esters, for example by treatment with lithium hydroxide in a mixture of tetrahydrofuran and water.

Many suitable aryl-thiocarboxamides (both carbocyclic and heterocyclic) are available commercially. For example, the Available Chemicals Directory (ACD, from MDL Inc., San Leandro, Calif.) lists 200 commercially available aryl-thiocarboxamides, examples of which include:

| Commercial sources of thiobenzamides | |
|---|---|
| Reagent name | Supplier |
| Thiobenzamide | Aldrich |
| 4-(Trifluoromethyl)-thiobenzamide | Aldrich |
| 2-Chlorothiobenzamide | Lancaster |
| 4-Chlorothiobenzamide | Lancaster |
| 2,3-Dichlorothiobenzamide | Maybridge International |
| 4-(tert-Butyl)thiobenzamide | Maybridge International |
| 4-Methoxythiobenzamide | Lancaster |
| 2,3-Dihydrobenzo[b]furan-5-carbothioamide | Maybridge International |
| 4-Methyl-thiobenzamide | Maybridge International |
| 2,4-Difluorothiobenzamide | Maybridge International |

Thiobenzamides useful for the preparation of compounds of this invention can also be made by reactions that are well known in the field of organic synthesis.

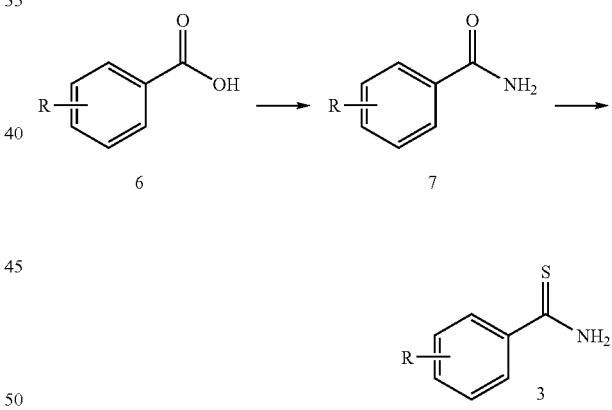

For example, thiobenzamides (3) can be made from benzoic acids of formula 6 as shown above. The amidation of a benzoic acids can be accomplished by activation of the carboxylic acid conveniently by treating it with a chlorinating agent such as thionyl chloride or phosphorus oxychloride or phosphorus pentachloride, in the optional additional presence of a catalytic amount of N,N-dimethylformamide, at a temperature between about 0° C. and about 80° C. depending on the reactivity of the chlorinating agent followed by treatment with ammonium hydroxide. The resultant benzamide (7) is then treated with $P_4S_{10}$. This method is reported in Collection of Czechoslovak Chemical Communications, 55(11), 2722-30; 1990.

Scheme 5

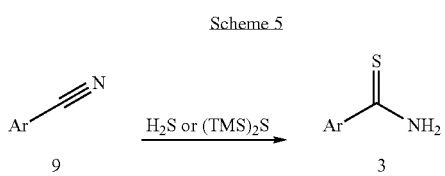

Alternatively, aryl-thiocarboxamides of formula 3 can be made by treatment of aryl nitrites in inert solvent with hydrogen sulfide or bis-(trimethylsilyl)sulfide as shown in Scheme 5 by heating the mixture at a temperature between about 70° C. and about 100° C. Aryl nitrites are available from a variety of different transformations known to those of skill in the art, such as those outlined in "Comprehensive Organic Transformations: A Guide to Functional Group Preparations" [R. C. Larock, VCH Publishers, Inc., N.Y. 1989, pages 861-862, 976-977, and 991-993] and in "Advanced Organic Chemistry" [J. March, 3$^{rd}$ Edition, Wiley Interscience, NY, 1985].

Scheme 6

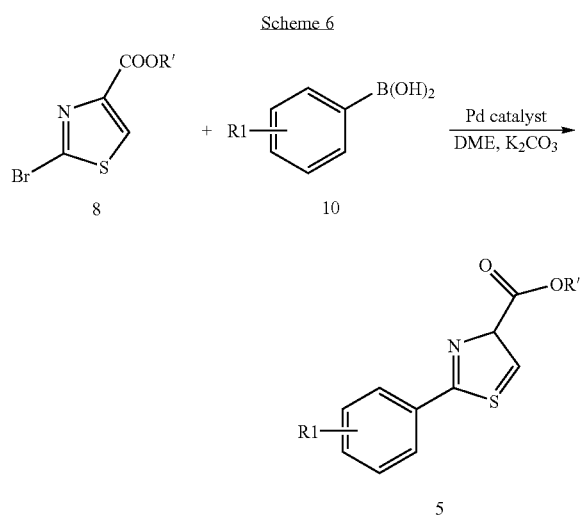

2-Aryl-thiazole-5-carboxylic acids of formula 5 can also be prepared as shown in Scheme 6 by coupling of 2-bromothiazole-4-carboxylic acid ethyl ester (8, R=Et, CAS #100367-77-9, coupling reactions conditions. The conditions of this method are disclosed in many publications which have been reviewed by A. Suzuki in an article entitled "The Suzuki reaction with arylboron compounds in arene chemistry" in *Modern Arene Chemistry* 2002, 53-106. In carrying out this reaction any of the conditions conventional in a Suzuki reaction can be utilized.

Generally these reactions are carried out in the presence of a metal catalyst such as a palladium catalyst utilizing any conventional organic solvent and a weak inorganic base. Among the preferred organic solvents are non-polar aprotic solvents, e.g. xylene or toluene, or polar aprotic solvents, e.g. dimethoxyethane. The weak inorganic base can be a carbonate or bicarbonate or phosphate or hydroxide, such as potassium carbonate, cesium carbonate, potassium phosphate or sodium hydroxide. As will be clear to one of skill in the art of organic synthesis, carrying out the reaction in the presence of sodium hydroxide will also lead to saponification of the ester. The source of palladium can be a palladium(0) complex (e.g., tetrakis(triphenylphosphine)palladium(0)) or a compound which can be reduced in situ to give palladium(0) (for example, palladium(II) acetate or bis(triphenylphosphine) palladium(II) chloride or Pd(dppf)Cl$_2$), and the reaction can be carried out in the optional additional presence of a catalytic amount of a phosphine ligand, for example tri-o-tolylphosphine or tri-tert-butylphosphine. The reaction is carried out at a temperature between about room temperature and about 100° C., and preferably about 90° C.

As will be clear to one of skill in the art of organic synthesis, the Stille or Negishi reactions can in many cases be used in place of the Suzuki reaction. Information on the Stille reaction can be found in an article by M. Kosugi and K. Fugami in *Handbook of Organopalladium Chemistry for Organic Synthesis*; E.-I. Negishi, Ed.; John Wiley & Sons, Inc., Hoboken, N.J., 2002, pages 263-283. For example, the reaction can be conveniently carried out by reacting a compound of formula 8 with a compound of formula Ar-M where M represents SnMe$_3$ or SnBu$_3$, in a convenient inert solvent such as dioxane, in the presence of a catalytic amount of a palladium(0) complex (e.g., tetrakis(triphenylphosphine)palladium(0)) or a compound which can be reduced in situ to give palladium(0) (for example, palladium(II) acetate or bis (triphenylphosphine)palladium(II) chloride), in the presence of a catalytic amount of a phosphine ligand, for example tri-o-tolylphosphine, at a temperature about 100° C. Another alternative is to use the Negishi reaction whereby a compound of formula 8 is treated with an organozinc reagent of formula Ar—ZnBr in a convenient inert solvent such as tetrahydrofuran, in the presence of a catalytic amount of a palladium(0) complex (e.g., tetrakis(triphenylphosphine)palladium(0)) or Cl$_2$Pd(dppf)-CH$_2$Cl$_2$), at a temperature about 65° C. Suitable reaction conditions can be found in the literature, for example in J. A. Miller and R. P Farrell *Tetrahedron Lett.* 1998, 39, 6441-6444; and in K. J. Hodgetts and M. T. Kershaw *Org. Lett.* 2002, 4, 1363-1365.

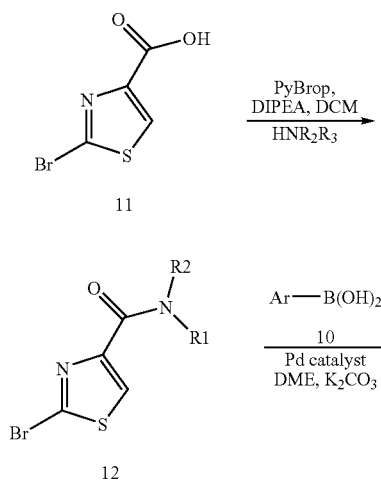

-continued

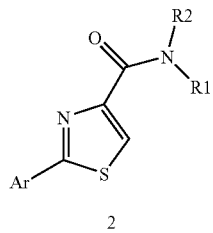

2

Alternatively, compounds of structure 2 can be prepared as shown in Scheme 7 by hydrolyzing an ester of formula 8, coupling the resulting carboxylic acid of formula 11 with an amine of formula HNR2R3, and then carrying out a Suzuki reaction on the amide of formula 12. As will be evident to one of skill in the art, a Stille reaction or Negishi reaction as mentioned above can be used in place of a Suzuki reaction. The ester hydrolysis can be conveniently effected by treating the compound of formula 8 where R'=Et with one equivalent of an alkali metal hydroxide, such as potassium hydroxide, sodium hydroxide, or lithium hydroxide, preferably lithium hydroxide, in a suitable solvent, such as a mixture of tetrahydrofuran, methanol, and water. The reaction can be carried out at a temperature between about 0° C. and about 70° C., preferably at about 65° C. The coupling of the acid of formula 11 with an amine of formula HNR2R3 can be carried out using conditions described above in connection with Scheme 1. A further example of a coupling agent which is convenient for this coupling reaction is PyBrop (bromotripyrrolidinophosphonium hexafluorophosphate, CAS #132705-51-2, available from Fluka Chemical Corp., Milwaukee, Wis.). The Suzuki reaction is conveniently carried out as described above in relation to Scheme 6.

Examples of boronic acids useful for the preparation of compounds of the invention are included in the following table:

Phenyl boronic acids and boronic esters useful in the preparation of compounds of formula 2 may be commercially available or can be made by reactions that are well known in the field of organic synthesis, such as those outlined below. Phenyl boronic acids and phenyl boronic esters are formed by treatment of aryl halides (13) with organo lithium reagents such as n-butyl lithium followed by treatment with boron triisopropoxide or 4,4,4',4',5,5,5',5'-octamethyl-2,2'-bi-1,3,2-dioxaborolane, followed by acidic work-up as is well known to those skilled in the art.

Scheme 8

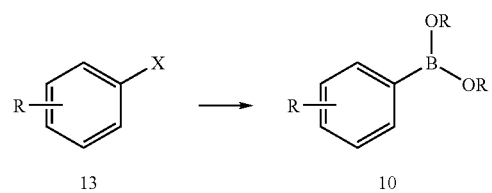

Several primary and secondary amines are applicable for use in the methods described above; such amine reagents are commercially available from suppliers such as Aldrich Chemical Company, Inc. (Milwaukee, Wis.), Lancaster Synthesis Ltd. (Lancashire, UK), TCI America (Portland, Oreg.), and Maybridge plc (Tintagel, Cornwall, UK). For the purposes of illustration, a number of commercially available amines are shown in the table below. Many other examples can be found by consulting the Available Chemicals Directory (MDL Information Systems, San Leandro, Calif.) or SciFinder (Chemical Abstracts Service, Columbus, Ohio).

| Boronic acids | |
|---|---|
| 3-Chloro-phenylboronic acid | 3-Methoxyphenylboronic acid |
| 3-Chloro-5-methylphenylboronic acid | 2-Trifluoromethoxyphenylboronic acid |
| 3-Chloro-6-methoxyphenylboronic acid | 3-Trifluoromethoxyphenylboronic acid |
| 3-Chloro-4-fluorophenylboronic acid | 2-Benzyloxyphenylboronic acid |
| 3-Chloro-4-methylphenylboronic acid | 3-Benzyloxyphenylboronic acid |
| 3-Chloro-2-methylphenylboronic acid | (2-Phenoxy)phenylboronic acid |
| 4-Chloro-3-methylphenylboronic acid | 6-Fluoro-2-methoxyphenylboronic acid |
| 2,4-Di-chlorophenylboronic acid | 2-Fluoro-3-methoxyphenylboronic acid |
| 4-Chloro-2-methylphenylboronic acid | 5-Fluoro-2-methoxyphenylboronic acid |
| 4-Chloro-2-methoxylphenylboronic acid | 3,4-Dimethoxyphenylboronic acid |
| 4-Chloro-2-ethoxylphenylboronic acid | 2,5-Dimethoxyphenylboronic acid |
| 4-Chloro-3-aminophenylboronic acid | 5-Benzo[1,3]dioxoleboronic acid |
| 3-Isopropylphenylboronic acid | 2,3,4-Trimethoxyphenylboronic acid |
| 2,5-Dichlorophenylboronic acid | 2-Methylsulfanyl-phenylboronic acid |
| Cyclopenten-1-ylboronic acid | 3-Methylsulfanyl-phenol |
| Cyclohexen-1-ylboronic acid | 2-Aminophenyl boronic acid |
| Cyclohepten-1-ylboronic acid | 3-Aminophenyl boronic acid |
| Thiophene-3-boronic acid | N-(2-Phenylboronic acid)-methanesulfonamide |
| 2-Acetylphenylboronic acid | 2-Nitrophenylboronic acid |
| 2-Methylphenylboronic acid | 4-Phenyl-phenylboronic acid |
| 3-Methylphenylboronic acid | 3-Phenyl-phenylboronic acid |
| (2-Hydroxymethylphenyl)boronic acid dehydrate | 2-Phenyl-phenylboronic acid |
| (3-Hydroxymethylphenyl)boronic acid dehydrate | 1H-Indole-5-boronic acid |
| 4-Hydroxyphenyl)boronic acid dehydrate | Quinoline-8-boronic acid |
| 2-Methoxyphenylboronic acid | |

| Commercially available amine reagent | |
|---|---|
| trans-decahydroisoquinoline | 3-pyridin-3-yl-pyrrolidine |
| (2S,6R)-2,6-dimethyl-piperidine | 4-chlorodecahydro-quinoline |
| 2-2(Pyridyl)-piperidine hdyrochloride | 4-hydroxy-cyclohexyl-amine |
| 1,7,7-trimethyl-bicyclo[2.2.1]hept-2-ylamine | 5-hydroxy-adaman-ylamine |
| 2,6,6-trimethyl-bicyclo[3.1.1]hept-3-ylamine | 7-Aza-bicyclo[2.2.1]heptane |
| 2,6-dimethyl-morpholine | adamantan-1-ylamine |
| 2,6-dimethylpiperidine | Adamantan-2-ylamine |
| 2-ethyl-piperidine | allyl-cyclohexyl-amine |
| 2-isobutyl-pyrrolidine | azepan-4-one |
| 2-isopropyl-pyrrolidine | azepane |
| 2-methylpiperidine | azocane |
| 2-propyl-piperidine | benzyl-isopropyl-amine |
| 3,3,5-Trimethyl-6-aza-bicyclo[3.2.1]octane | cycloheptylamine |
| 3,5-dimethylpiperidine | cyclohexyl-ethyl-amine |
| 3-Aza-bicyclo[3.2.2]nonane | cyclohexyl-methyl-amine |
| 3-benzyl-piperidine | cyclooctylamine |
| 3-phenyl-morpholine | decahydroisoquinoline |
| 3-phenyl-pyrrolidine | decahydro-quinoline |
| 3-phenyl-thiomorpholine | hexahydro-furo[3,2-c]quinoline |
| (1R,2R,4R)-1,7,7-trimethyl-bicyclo[2.2.1]hept-2-ylamine | |
| (1R,2S,4R)-1,7,7-trimethyl-bicyclo[2.2.1]hept-2-ylamine | |
| 4,7,7-trimethyl-bicyclo[2.2.1]hept-2-ylamine | |

The invention will now be further described in the Examples which follow, which are intended as an illustration only and do not limit the scope of the invention.

EXAMPLES

Reagents were purchased from Aldrich, Sigma, Bachem Biosciences, Advanced ChemTech, Lancaster and Argonaut Argogel and used without further purification. Unless otherwise indicated, all reagents were obtained from commercial sources. LC/MS (liquid chromatography/mass spectroscopy) spectra were recorded using the following system. For measurement of mass spectra the system was configured with a Micromass Platform II: API Ionization in positive electrospray (mass range: 150-1200 amu). The simultaneous chromatographic separation was achieved with the following HPLC system: Column, ES Industries Chromegabond WR C-18 3u 120 Å (3.2×30 mm) Cartridge; Mobile Phase A: Water (0.02% TFA) and Phase B: Acetonitrile (0.02% TFA); gradient 10% B to 90% B in 3 minutes; equilibration time, 1 minute; flow rate of 2 mL/minute.

Compounds were purified using various methods of chromatography including flash column chromatography using silica gel and eluting with ethyl acetate and hexane solvent mixtures or other appropriate solvents. Certain compounds were also purified by reversed phased HPLC, using methods well known to those skilled in the art.

Intermediate 1:
2-(2-Hydroxymethyl-phenyl)-thiazole-4-carboxylic Acid

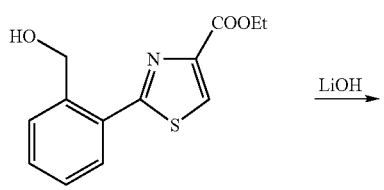

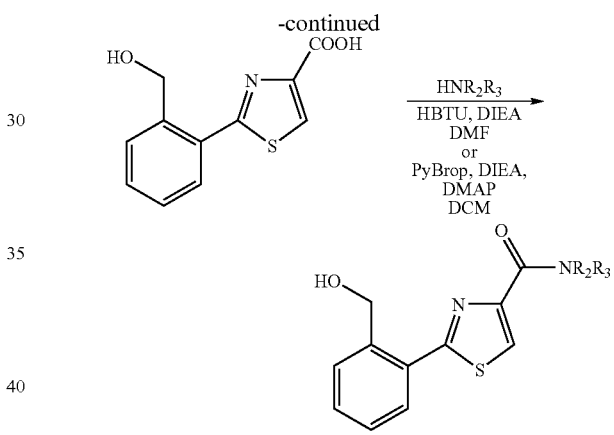

Step 1. 2-(2-hydroxymethyl-phenyl)-thiazole-4-carboxylic Acid, Ethyl Ester

Ethyl 2-bromothiazole-4-carboxylate (Combi-Blocks, Inc., San Diego, Calif.; 2.0 g, 8.5 mmol) and 2-hydroxymethylphenylboronic acid (Combi-Blocks, San Diego, Calif.; 1.1 g, 7.2 mmol) were dissolved in ethylene glycol dimethyl ether, followed by addition of 1,1'-bis(diphenylphosphino)ferrocene palladium(II) chloride complex with dichloromethane (Alfa Aesar; 350 mg, 0.43 mmol). Nitrogen was bubbled through the reaction mixture for 2 min and then 2 M aqueous solution of potassium carbonate was added (8.4 mL). The resulting mixture was stirred at 90° C. for 2 h. Then it was allowed to cool down to room temperature, diluted with ethyl acetate and filtered through Celite. The filtrate was then washed with water, dried over anhydrous sodium sulfate and filtered through a silica plug. The crude material was purified on silica gel column using ethyl acetate and hexanes to give 1.3 g of yellow oil. HRMS calcd for C13H13NO3S (M+) 263.0616, observed 263.0620.

Step 2. 2-(2-Hydroxvmethyl-phenyl)-thiazole-4-carboxylic Acid

To a solution of 2-(2-hydroxymethyl-phenyl)-thiazole-4-carboxylic acid, ethyl ester (1.3 g) in THF (5 mL) was added an aqueous solution of LiOH:H2O (472 mg in 5 mL water) and the resulting biphasic mixture was stirred vigorously at room temperature for 3 h. The reaction mixture was then acidified with 1N HCl, diluted with water and extracted three times with ethyl acetate. The combined organic extracts were dried over anhydrous sodium sulfate and then concentrated. The crude product was dissolved in a small amount of ethyl acetate and precipitated by addition of hexanes to give 2-(2-hydroxymethyl-phenyl)-thiazole-4-carboxylic acid (926 mg) as a light yellow solid. HRMS calcd for C11H9NO3S (M+) 235.0303, observed 235.0302.

Intermediate 2: 4-Amino-adamantan-1-ol

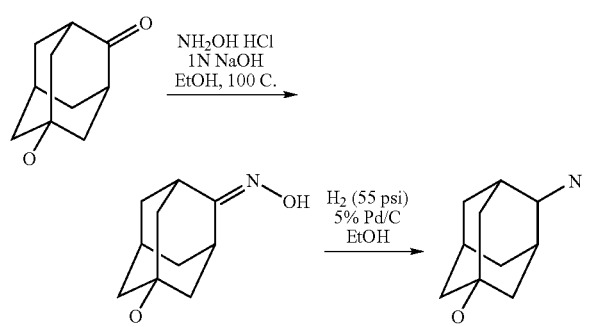

Step 1. 5-Hydroxy-adamantan-2-one Oxime

5-Hydroxyadmantan-2-one (TCI America, Portland, Oreg.; 3 g, 18.0 mmol) was dissolved in EtOH (20 mL) and the solution was added to a solution of hydroxylamine hydrochloride (12 g, 172.7 mmol) in 1N NaOH (16 mL). The mixture was heated at 100° C. for 1 hour. The EtOH was evaporated, and water and DCM were added. The separated aqueous layer was further extracted twice with DCM. The combined DCM layers were evaporated under vacuum. Crystallization from EtOAc gave 5-hydroxy-adamantan-2-one oxime (2.3 g, 71%).

Step 2. 4-Amino-adamantan-1-ol

Pd/C (5%, 0.05 g) was added to a mixture of 5-hydroxy-adamantan-2-one oxime (1 g, 5.5 mmol) in EtOH in a Parr hydrogenation bottle. The hydrogenation reaction was performed in a Parr hydrogenation instrument with 55 Psi pressure of hydrogen at room temperature for 72 hours. The mixture was filtered through celite and concentrated under vacuum to dryness to give 4-amino-adamantan-1-ol (0.82 g, 89%).

Intermediate 3: 2-Bromo-thiazole-4-carboxylic Acid

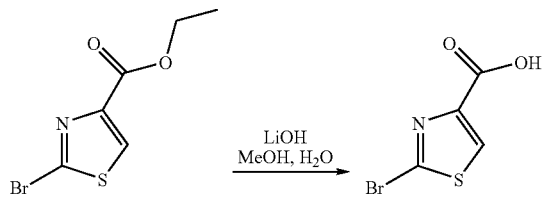

To a solution of 2-bromo-thiazole-4-carboxylic acid ethyl ester (Combi-Blocks, Inc., San Diego, Calif.; 5 g, 21.2 mmol) in MeOH (25 mL) and water (25 mL) was added LiOH (0.56 g, 23.3 mmol). After stirring for 4 h at reflux temperature, MeOH was evaporated in vacuo. To the residue was added more water, the mixture was acidified to pH 2 with concentrated HCl (3 mL), and extracted with EtOAc. The combined extracts were evaporated to give 2-bromo-thiazole-4-carboxylic acid which was used without further purification. The compounds of the present invention were preferably prepared by methods A to F:

Method A

Preparation of Activated Carboxylic Acid Esters Useful for Parallel Library Synthesis

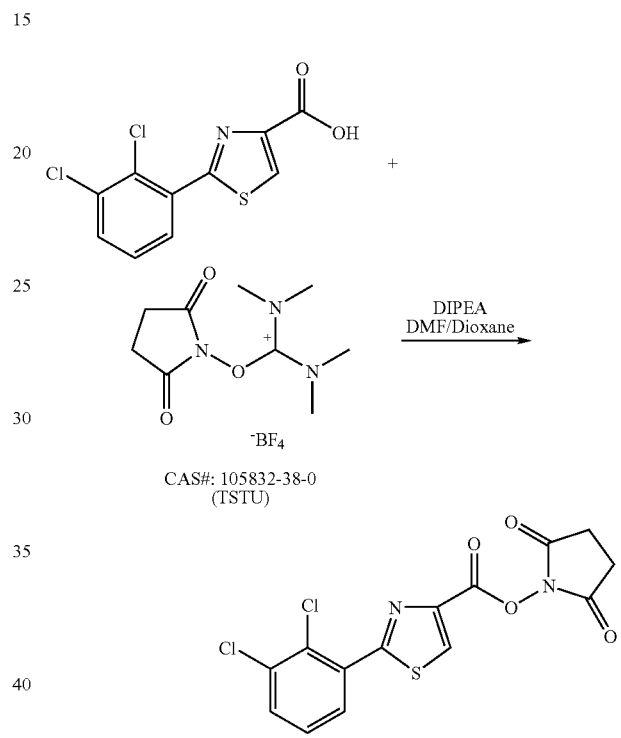

CAS#: 105832-38-0 (TSTU)

2-(2,3-Dichloro-phenyl)-thiazole-4-carboxylic acid (4.1 g, 15 mmol) was dissolved in a mixture of 50 mL of DMF and 50 mL of dioxane. To this solution diisopropylethylamine (7.8 mL, 45 mmol) and ethanaminium, N-[(dimethylamino) [(2,5-dioxo-1-pyrrolidinyl)oxy]methylene]-N-methyl-, tetrafluoroborate(1-) (TSTU, Aldrich Inc.; 6.8 g, 22.5 mmol) was added. The reaction mixture was stirred at room temperature for 3 h after which 150 mL water was added and the organic layer was separated. The organic layer was extracted with 50 mL water twice, dried and concentrated. The crude mixture was washed with 100 mL isopropanol, to give 2-(2,3-dichloro-phenyl)-thiazole-4-carboxylic acid 2,5-dioxo-pyrrolidin-1-yl ester (4.8 g, 87% yield) and used without further purification.

Parallel Library Synthesis Method

Commercially available primary and secondary amines at 0.3 molar concentration in DMF were prepared. Separately prepared were solutions of hydroxysuccinimde esters at 0.3 molar concentration in DMF. Using a multi-channel automated liquid handling system (TECAN Int.) 0.25 mL of the amine solutions were arrayed on a microtitre plate. To corresponding wells were added 0.25 mL of the hydroxysuccinimde ester solutions. To the reaction mixture of each well was added 0.15 mL of a triethylamine solution in DMF at 1.0 molar concentration. The reaction plates were sealed and shaken at room temperature overnight. At this time, the solutions in each well of the reaction plates were concentrated to remove volatile solvents at room temperature using a Genevac centrifugal evaporation system. The residue in each well was worked up using a multi-channel automated liquid handling system such as that made by TECAN to perform a dichloromethane-water liquid-liquid extraction. The desired compounds were obtained in the dichloromethane layer. From the dichloromethane layer, aliquots were removed for analysis by a LC-MS system. Subsequently, dichloromethane was removed using a centrifugal evaporation system.

Examples of compounds synthesized in this manner include [2-(2,3-Dichloro-phenyl)-thiazol-4-yl]-(octahydro-quinolin-1-yl)-methanone (compound of Example 1); Azocan-1-yl-[2-(2,3-dichloro-phenyl)-thiazol-4-yl]-methanone (compound of Example 2); and Azepan-1-yl-[2-(2,3-dichloro-phenyl)-thiazol-4-yl]-methanone (compound of Example 3).

Method B

Preparation of Activated Carboxylic Acid Esters Useful for Parallel Library Synthesis

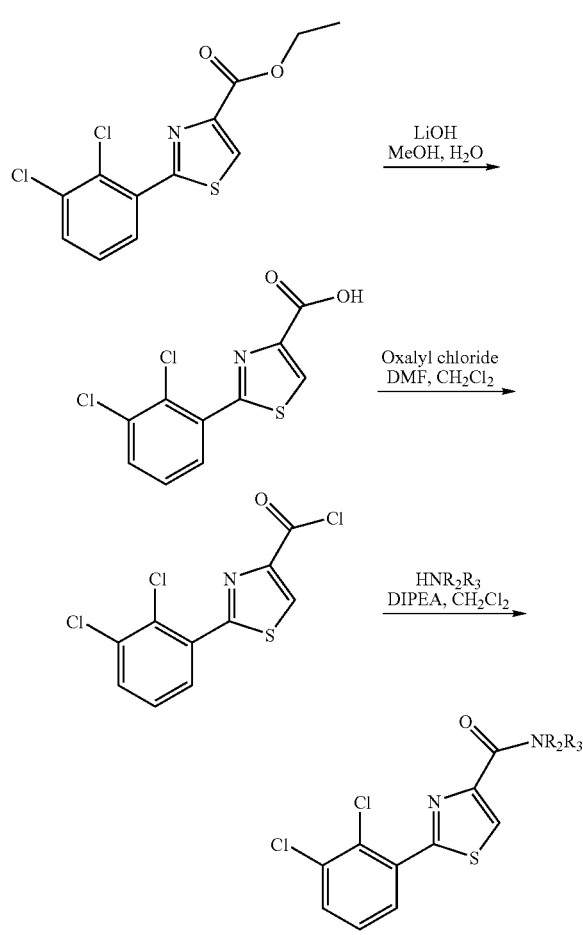

Step 1. Ester Hydrolysis

To a solution of 2-(2,3-dichloro-phenyl)-thiazole-4-carboxylic acid ethyl ester (Maybridge plc, Tintagel, Cornwall, UK; 20 g, 66.2 mmol) in MeOH (100 mL) and water (100 mL) was added LiOH (1.7 g. 72.8 mmol). After stirring for 4 h at reflux temperature, MeOH was evaporated in vacuo. To the residue was added more water, and the solution was acidified to pH 2 with concentrated HCl (7 mL), and extracted with EtOAc. The combined extracts were evaporated to give product which was used without further purification.

Step 2. Preparation of Acid Chloride

To a solution of 2-(2,3-dichloro-phenyl)-thiazole-4-carboxylic acid (40 mmol) in dry dichloromethane (150 mL) was added oxalyl chloride (10 mL of 2 M solution in dichloromethane, 20 mmol) slowly. Dry DMF (5 mL) was added subsequently with extreme caution over 10 minutes. After the gas evolution ceased, the mixture was stirred for another 30 minutes. The mixture was evaporated to dryness under reduced pressure. Then dry toluene was added to the residue and evaporated again to dryness under highly reduced pressure. The resultant product was used for the next step without further purification.

Step 3. Preparation of Amide

A 1.0 M solution of 2-(2,3-dichloro-phenyl)-thiazole-4-carbonyl chloride (11.7 g, 40 mmol) in 40 mL dichloromethane was prepared, and 0.2 mL of such solution (0.2 mmol) was distributed to reaction tubes with a TECAN automated liquid handler. Then separate 0.5 M solutions of each reacting amine in dichloromethane (DCM) were prepared, and 0.4 mL of each solution was added with TECAN automated liquid handler to the above reaction tubes cooled in an ice-water bath. 1.0 M DIPEA (0.8 mL, 0.8 mmol) in DCM was added to each tube in the ice-water bath. After stirring in the ice-water bath for 30 minutes, the reaction mixture was stirred for another 4 hours at room temperature. The reaction mixture was subjected to liquid-liquid extraction three times with water and DCM. The organic layer was combined and evaporated to dryness under reduced pressure. The final product was purified by C-18 reversed phase HPLC with a gradient of 25%-100% Acetonitrile/Water.

An example of a compound synthesized in this manner includes (Octahydro-quinolin-1-yl)-(2-phenyl-thiazol-4-yl)-methanone (compound of Example 4).

Method C

Amide Coupling for Single Compound Synthesis

Some compounds of the present invention were alternatively prepared by amide coupling. For example, [2-(2,3-Dichloro-phenyl)-thiazol-4-yl]-(octahydro-quinolin-1-yl)-methanone (the compound of Example 1) was prepared as follows:

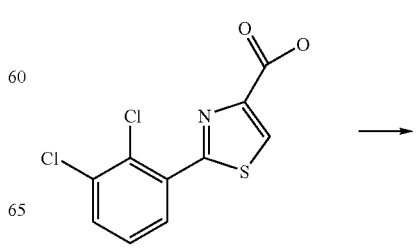

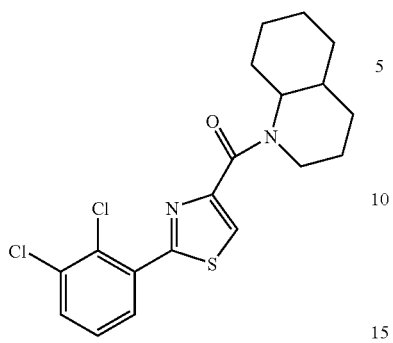

A solution of 2-(2,3-dichloro-phenyl)-thiazole-4-carboxylic acid (Maybridge; 1.0 g, 3.66 mmol), decahydro-quinoline (Aldrich; 0.56 g, 4.0 mmol), O-(7-Azabenzotriazol-1-yl)-N,N,N',N'tetramethyluronium hexafluorophosphate (HATU, 1.46 g, 3.84 mmol) and diisopropylethylamine (0.67 mL, 3.84 mmol) in DMF (2 mL) was stirred at room temperature overnight. At this time, the reaction mixture was diluted with ethyl acetate and extracted twice with 1 N HCl and twice with water. The ethyl acetate layer was washed with brine, dried over MgSO$_4$ and then treated with decolorizing carbon. The solution was concentrated in vacuo. The product was purified by silica gel flash column chromatography eluting with an ethyl acetate/hexane gradient. LC-MS m/e calcd for C19H20N2Cl2OS (M+H$^+$) 394, found 394.

Method D

Preparation of Target Compounds Starting from Thiobenzamide Precursors

Thiobenzamide precursors were used to make compounds of the invention. For example, (octahydro-quinolin-1-yl)-(2-phenyl-thiazol-4-yl)-methanone (the compound of Example 4) was synthesized in the following manner:

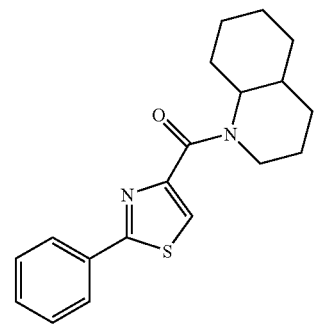

Step 1. 2-Phenyl-thiazole-4-carboxylic Acid

A solution of thiobenzamide (Aldrich; 1.37 g, 10 mmol) and 3-bromopyruvic acid (1.67 g, 10 mmol) in dioxane (50 mL) was heated at reflux for 2 hrs. The solution was concentrated in vacuo. Water (50 mL) was added. The resulting solid was filtered and triturated with ether to give a white solid (2.0 g, 99%).

Step 2. (Octahydro-quinolin-1-yl)-(2-phenyl-thiazol-4-yl)-methanone

2-Phenyl-thiazole-4-carboxylic acid (205 mg), HATU (418 mg), and decahydroquinoline (139 mg) were dissolved in DMF (5 mL). Diisopropylethylamine (192 μL) was added. The resulting mixture was stirred at ambient temperature overnight. The solution was diluted with 20 ml of ethyl acetate and washed with 0.2N HCl (2×10 mL), saturated NaHCO3 (10 mL) and brine (10 mL), dried (MgSO4) and concentrated in vacuo to give a white foam. The crude material was purified by flash chromatography (0-30% ethyl acetate/hexane) to give a white solid (305 mg, 94%): LC-MS m/e calcd for C19H22N2OS (M+H$^+$) 327, found 327.

[2-(2,3-Dichloro-phenyl)-thiazol-4-yl]-(octahydro-quinolin-1-yl)-methanone was also synthesized in the following manner.

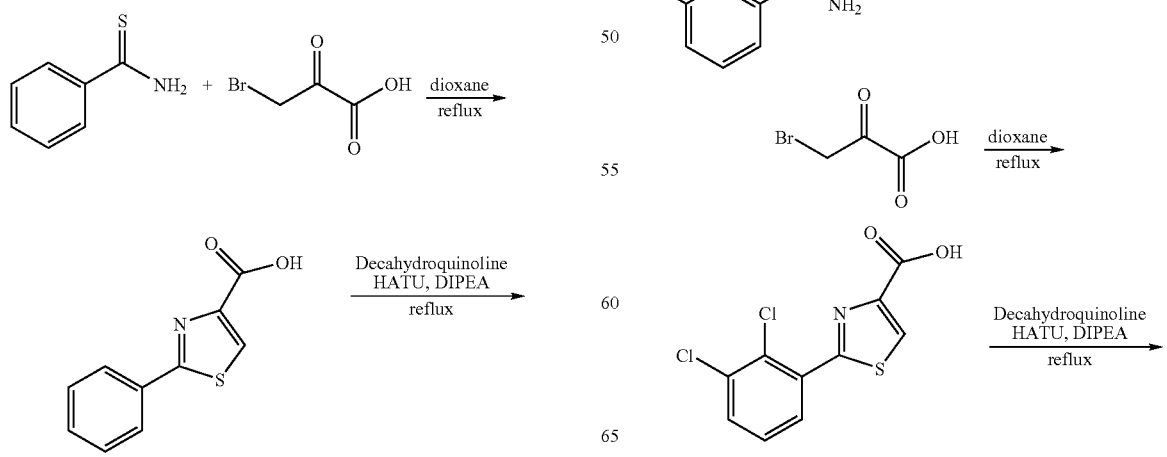

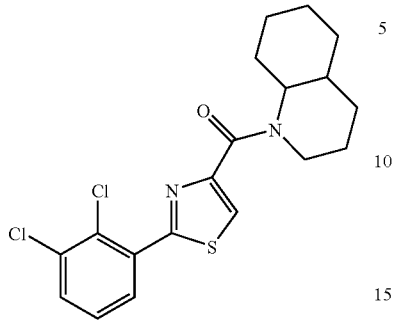

Step 1. 2-(2,3-Dichloro-phenyl)-thiazole-4-carboxylic Acid

A solution of 2,3-dichloro-thiobenzamide (Maybridge plc, Tintagel, Cornwall, UK; 2.06 g, 10 mmol) and 3-bromopyruvic acid (1.67 g, 10 mmol) in dioxane (50 mL) was heated at reflux for 2 hrs. The solution was concentrated in vacuo. Water (50 mL) was added. The resulting solid was filtered and triturated with ether to give a white solid (2.68 g, 98%).

Step 2. [2-(2,3-Dichloro-phenyl)-thiazol]-4-yl-(octahydro-quinolin-1-yl)-methanone 2-(2,3-Dichloro-phenyl)-thiazole-4-carboxylic acid (822 mg), HATU (1.25 g), and decahydroquinoline (418 mg) were dissolved in DMF (10 mL). Diisopropylethylamine (575 µL) was added. The resulting mixture was stirred at ambient temperature overnight. The solution was diluted with 50 ml of ethyl acetate and washed with 0.2N HCl (2×25 mL), saturated NaHCO3 (20 mL) and brine (20 mL), dried (MgSO4) and concentrated in vacuo to give a yellow foam. The crude material was purified by flash chromatography (0-20% ethyl acetate/hexane) to give a white solid (978 mg, 83%): LC-MS m/e calcd for C19H20Cl2N2OS (M+H$^+$) 395, found 395.

Method E

Preparation of Target Compounds Starting from Ethyl 2-bromothiazole-4-carboxylate Precursors Ethyl 2-bromothiazole-4-carboxylate precursors were used to prepare compounds of the present invention.

Preparation of [2-(2-Fluoro-6-methoxy-phenyl)-thiazol-4-yl]-(2-methyl-piperidin-1-yl)-methanone

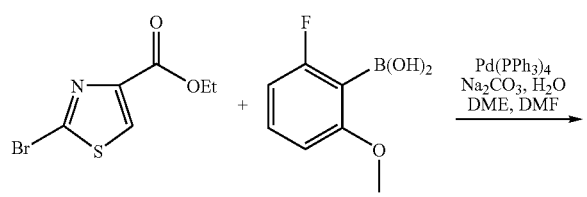

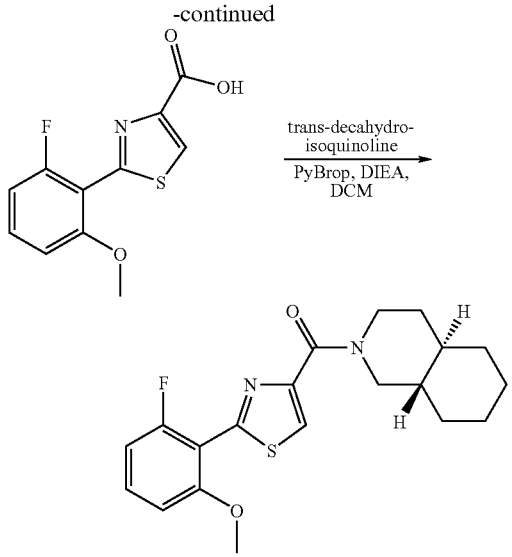

Step 1: 2-(2-Fluoro-6-methoxy-phenyl)-thiazole-4-carboxylic Acid

Tetrakis(triphenylphosphine)palladium (0.54 g, 0.48 mmol, 2.2% mol eq) was added to a degassed (nitrogen) mixture of 2-bromo-thiazole-4-carboxylic acid ethyl ester (Combi-Blocks, Inc., San Diego, Calif.; 5 g, 21.2 mmol), 1-methoxy-6-flurophenylboronic acid (4.68 g, 27.56 mmol), and sodium carbonate(23 mL, 2 M solution in water) in DME (100 mL) and DMF (100 mL). The reaction mixture was refluxed under inert atmosphere overnight. After cooling to room temperature, the reaction mixture was filtered through celite, and water and EtOAc were added. The aqueous layer was separated, acidified with conc. HCl to pH 2 and then was extracted three times with EtOAc. The combined EtOAc layers were dried under vacuum. The residue was chromatographed on silica, eluting with EtOAc/Hexane (0-30% gradient) to give 2-(2-fluoro-6-methoxy-phenyl)-thiazole-4-carboxylic acid (4.5 g) which was used directly in the next step.

Step 2: [2-(2-Fluoro-6-methoxy-phenyl)-thiazol-4-yl]-(2-methyl-piperidin-1-yl)-methanone 2-(2-Fluoro-6-methoxy-phenyl)-thiazole-4-carboxylic acid (49.5 mg, 0.2 mmol) from the previous step, trans-decahydro-isoquinoline (TCI America, Portland, Oreg.; 27.8 mg, 0.2 mmol), DIPEA (0.1 mL, 0.57 mmol), and PyBrop (103 mg, 0.22 mmol) were mixed in dry DCM (1 mL) and the mixture was left stirring for overnight at room temperature. To the mixture was added water. The DCM layer was separated and the aqueous layer was extracted with DCM twice. The combined DCM layers were dried under vacuum and purified by C-18 reversed phase HPLC with a gradient of 10-100% Acetonitrile/water to give [2-(2-fluoro-6-methoxy-phenyl)-thiazol-4-yl]-(2-methyl-piperidin-1-yl)-methanone (12 mg, 16%).

1-{2-[4-((trans)-Octahydro-isoquinoline-2-carbonyl)-thiazol-2-yl]-phenyl}-ethanone was synthesized in a similar manner, by the reaction of 2-acetyl-phenyl-boronic acid (Aldrich) with 2-bromo-thiazole-4-carboxylic acid ethyl ester (Combi-Blocks, Inc., San Diego, Calif.) in a Suzuki reaction, followed by hydrolysis and coupling with trans-decahydroquinoline.

2-(2-acetyl-phenyl)-thiazole-4-carboxylic acid (5-hydroxy-adamantan-2-yl)-amide (the compound of Example 168) was prepared using Method E:

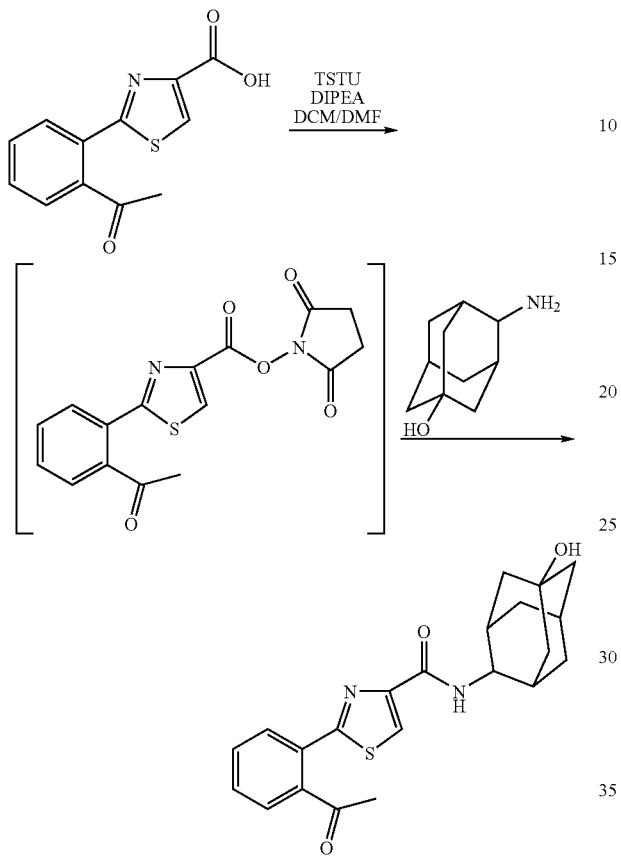

2-(2-Acetyl-phenyl)-thiazole-4-carboxylic acid (prepared in a Suzuki reaction between 2-acetyl-phenyl-boronic acid [Aldrich] with 2-bromo-thiazole-4-carboxylic acid ethyl ester [Combi-Blocks, Inc., San Diego, Calif.] using conditions similar to those described above for the preparation of 2-(2-fluoro-6-methoxy-phenyl)-thiazole-4-carboxylic acid; 49.5 mg, 0.2 mmol) was dissolved in a mixture of dry DCM (1.6 mL) and dry DMF (0.4 mL). DIPEA (0.1 mL) and TSTU (72 mg, 0.24 mmol) were added to the mixture. After the mixture was stirred for 2 h and checked with LC-MS for the generation of active ester, 4-aminoadamantan-1-ol (Intermediate 2; 33.5 mg, 0.2 mmol) from Step 2 was added to the mixture. After another 2 hours water was added to the mixture and the organic layer was separated. The aqueous layer was further extracted twice with DCM. The combined organic layers were evaporated under vacuum and purified by C-18 reversed phase HPLC with a gradient of 10-100% Acetonitrile/water to give 36 mg product.

Method F

Preparation of Target Compounds Starting from 2-bromothiazole-4-carboxylic Acid Precursors Another preferred method of synthesizing compounds of the present invention utilizes 2-bromothiazole-4-carboxylic acid precursors. The compounds of Examples 92, 119 and 125 were made in this manner:

Example 92

Synthesis of 1-{2-[4-(Octahydro-quinoline-1-carbonyl)-thiazol-2-yl]-phenyl}-ethanone

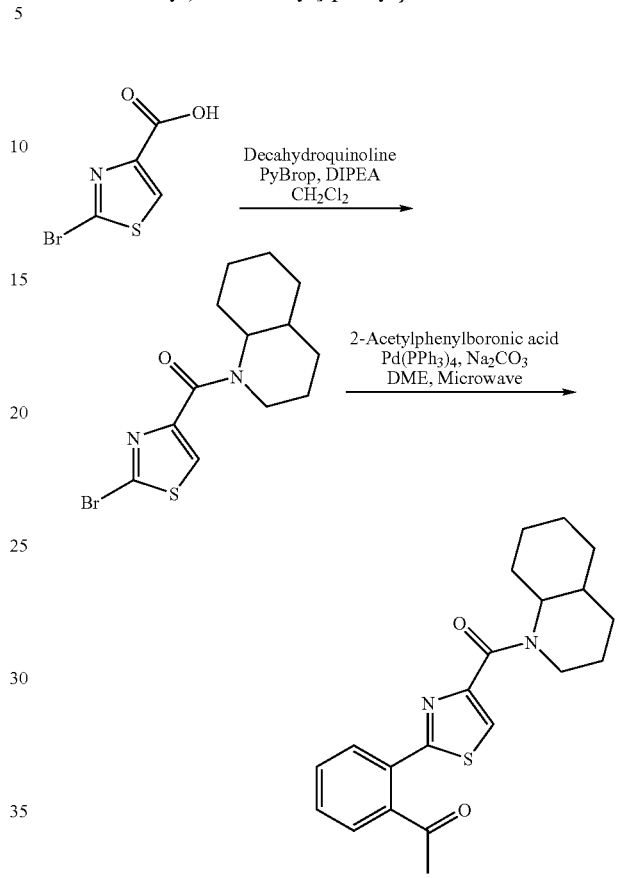

Step 1. (2-Bromo-thiazol-4-yl)-(octahydro-guinolin-1-yl)-methanone

A solution of 2-bromo-thiazole-4-carboxylic acid (Intermediate 3; 21.2 mmol), decahydroquinoline (3.54 g, 25.4 mmol), DIPEA (7.4 mL, 42.4 mmol), and PyBrop (11.9 g, 25.4 mmol) in dry DCM (70 mL) was stirred overnight at room temperature. The mixture was extracted with DCM and water three times. The combined DCM extracts were evaporated, and the residue was chromatographed on silica, eluting with EtOAc/Hexane (0-10% gradient) to give (2-bromo-thiazol-4-yl)-(octahydro-quinolin-1-yl)-methanone (6.0 g, 86%).

Step 2. 1-{2-[4-(Octahydro-quinoline-1-carbonyl)-thiazol-2-yl]-phenyl}-ethanone

In a Microwave process tube, tetrakis(triphenylphosphine)palladium (5 mg, 0.004 mmol) was added to a degassed (nitrogen) mixture of 2-acetylphenylboronic acid (Aldrich; 38 mg, 0.15 mmol) and sodium carbonate (2 M in water, 0.2 mL, 0.4 mmol), and (2-bromo-thiazol-4-yl)-(octahydro-qunolin-1-yl)-methanone (from Step 1; 50 mg, 0.15 mmol) in DME (dry, 1.5 mL). The tube was submitted to 150 W Microwave Irradiation at 160° C. for 5 minutes. The reaction mixture was cooled to room temperature, filtered through celite and silica plug, and extracted with EtOAc and water three times. The organic layers were combined, concentrated and purified by C-18 reversed phase HPLC with a gradient of 10-100% Acetonitrile/Water to give 1-{2-[4-(octahydro-quinoline-1-carbonyl)-thiazol-2-yl]-phenyl}-ethanone (40 mg, 70%).

Example 119

Synthesis of [2-(2-Methoxy-phenyl)-thiazol-4-yl]-(2-methyl-piperidin-1-yl)-methanone

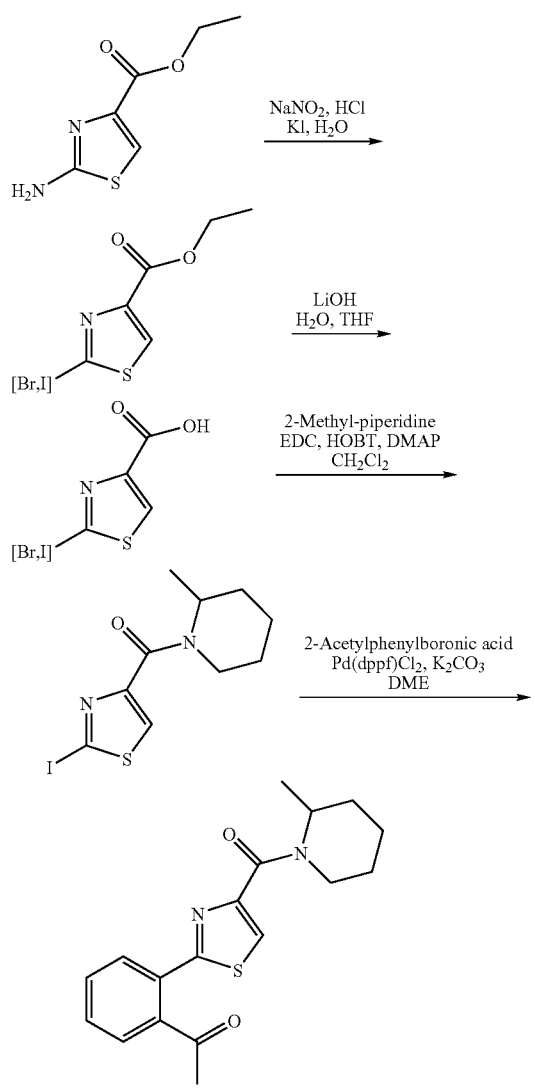

Step 1. Mixture of 2-iodo-thiazole-4-carboxylic Acid Ethyl Ester and 2-bromo-thiazole-4-carboxylic Acid Ethyl Ester To a 1 L, 3-necked round bottom flask was added 2-amino-thiazole-4-carboxylic acid ethyl ester hydrobromide (20 g, 79 mmol). This was diluted with water (150 mL) followed by conc. HCl (150 mL). This mixture was cooled to ~minus 5° C. Separately, 8.15 g of sodium nitrite was dissolved in 75 mL of water. A solution of sodium nitrite (8.15 g, 118.1 mmol) in water (75 mL) was slowly added dropwise over a 30 minute period. The mixture was stirred for approximately 2 h after the completion of the addition of the sodium nitrite solution while maintaining the reaction temperature at 0° C. To this mixture was added dropwise over 10 minutes a solution of potassium iodide (17.6 g, 106.0 mmol) in water (75 mL). During the addition, dichloromethane was added to maintain the fluidity of the reaction mixture. After 1 hour, the ice bath was removed. The mixture was extracted with dichloromethane (3×500 mL). The combined organic extracts were washed with 10% $Na_2S_2O_3$ (2×250 mL). The organic layer was dried over $MgSO_4$, filtered and concentrated in vacuo. The residue was purified by silica gel flash column chromatography eluting with 10-75% dichloromethane in hexane to give a mixture of 2-iodo-thiazole-4-carboxylic acid ethyl ester and 2-bromo-thiazole-4-carboxylic acid ethyl ester (10.8 g). This material was used for the next step without further purification.

Step 2. Mixture of 2-iodo-thiazole-4-carboxylic Acid Ethyl Ester and 2-bromo-thiazole-4-carboxylic Acid A solution of lithium hydroxide (3.27 g, 136.5 mmol) in water (65 mL) was added to a solution of the mixture of 2-iodo-thiazole-4-carboxylic acid ethyl ester and 2-bromo-thiazole-4-carboxylic acid ethyl ester (from Step 1; 10.8 g) in tetrahydrofuran (100 mL). The mixture was stirred at room temperature for 2.5 hours. At this time, the reaction mixture was concentrated in vacuo, followed by addition of water (100 mL). The resultant solution was acidified to pH 1 with 1 M HCl. A white solid was formed. The aqueous suspension was extracted with ethyl acetate (3×250 mL). The combined organic extracts were washed with water (250 mL) and brine (250 mL). The combined organic extracts were dried over $MgSO_4$, filtered and then concentrated in vacuo to give a mixture of 2-iodo-thiazole-4-carboxylic acid ethyl ester and 2-bromo-thiazole-4-carboxylic acid (11.5 g). This material was used in the next step without further purification.

Step 3. (2-Iodo-thiazol-4-yl)-(2-methyl-piperidin-1-yl)-methanone

A solution of a mixture of 2-iodo-thiazole-4-carboxylic acid ethyl ester and 2-bromo-thiazole-4-carboxylic acid (from Step 2; 11.5 g), N,N-dimethylaminopyridine (11.2 g, 91.7 mmol), HOBT (10.0 g, 74.0 mmol), 1-(3-dimethylaminopropyl)-3-ethyl-carbodiimide hydrochloride (14.0 g, 73.0 mmol), and 2-methyl-piperidine (8 mL, 68.1 mol) in dry dichloromethane (150 mL) and dry acetonitrile (20 mL) was stirred at room temperature for 72 h. At this time, the reaction mixture was concentrated in vacuo. The resulting solution was diluted with dichloromethane (25 mL) and 1 N HCl (250 mL). The mixture was stirred for several hours at room temperature. At this time, the mixture was filtered and the solids were washed with dichloromethane (200 mL). The aqueous layer was extracted with dichloromethane (2×250 mL). The combined organic layers were washed with water (450 mL) and brine (450 mL). The organic layer was dried over $MgSO_4$, filtered, concentrated in vacuo, and purified by flash column chromatography eluting with a gradient of ethyl acetate in hexanes to give (2-iodo-thiazol-4-yl)-(2-methyl-piperidin-1-yl)-methanone (8.1 g, 30% yield from 2-amino-thiazole-4-carboxylic acid ethyl ester hydrobromide).

Step 4. [2-(2-Methoxy-phenyl)-thiazol-4-yl]-(2-methyl-piperidin-1-yl)-methanone

A mixture of (2-iodo-thiazol-4-yl)-(2-methyl-piperidin-1-yl)-methanone (Step 3; 200 mg, 0.59 mmol), 2-methoxyphenylboronic acid (Combi-Blocks, Inc., San Diego, Calif.; 135 mg, 0.89 mmol), potassium carbonate (201 mg, 1.45 mmol), and $PdCl_2$dppf (Strem Chemicals, Inc., Newburyport, Mass.; 22 mg, 0.03 mmol) in dimethoxyethane (3 mL) in a scintillation vial was heated at ~78° C. for 72 h with shaking. The reaction mixture was cooled to room temperature, concentrated in vacuo using a Genevac evaporator, and purified using automated mass-directed LC-MS purification.

Example 125

Synthesis of (2,6-Dimethyl-piperidin-1-yl)-(2-o-tolyl-thiazol-4-yl)-methanone

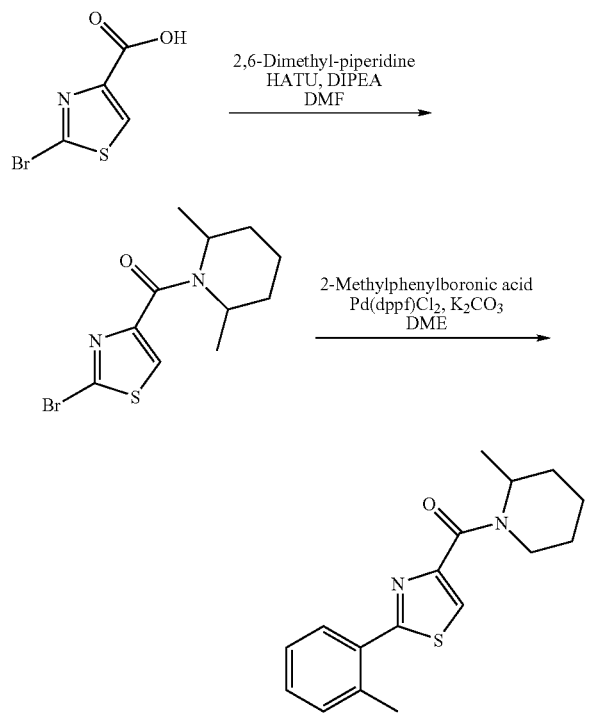

Step 1. (2-Bromo-thiazol-4-yl)-(2,6-dimethyl-piperidin-1-yl)-methanone

A solution of 2-bromothiazole-4-carboxylic acid (Intermediate 3; 2 g, 9.6 mmol), 2,6-dimethylpiperidine (1.18 mL, 8.8 mmol), HATU (4.18 g, 11.0 mmol) and DIEA (2.1 mL, 12.1 mmol) in DMF (10 mL) was stirred at room temperature for 1 h. Ethyl acetate (20 mL) was added and the solution was washed with 0.2 M HCl (2×10 mL), water (10 mL), and brine (10 mL), then it was dried (MgSO$_4$), filtered, evaporated, and purified by flash column chromatography (10-40% ethyl acetate/hexanes) to give (2-bromo-thiazol-4-yl)-(2,6-dimethyl-piperidin-1-yl)-methanone (2.3 g, 86%) as a white solid.

Step 2. (2,6-Dimethyl-piperidin-1-yl)-(2-o-tolyl-thiazol-4-yl)-methanone

A mixture containing (2-bromo-thiazol-4-yl)-(2,6-dimethyl-piperidin-1-yl)-methanone (Step 1; 91 mg, 0.3 mmol), 2-methylphenylboronic acid (45 mg, 0.33 mmol), Pd(dppf)Cl$_2$ (Dichloro-(1,1-bis(diphenylphosphino)-ferrocene) palladium(II)) (11 mg, 0.015 mmol), and potassium carbonate (0.3 mL, 2 M aqueous, 0.6 mmol) in DME (2 mL) was heated to 90° C. for 8 hrs. The solvent was evaporated and water (5 mL) was added. The mixture was extracted with ethyl acetate (3×5 mL). The combined organic layers were dried with MgSO$_4$ and concentrated in vacuo. The crude product was purified by flash chromatography with a solvent gradient of 0-30% ethyl acetate in hexanes to give (2,6-dimethyl-piperidin-1-yl)-(2-o-tolyl-thiazol-4-yl)-methanone (68 mg, 75%) as a white solid.

The compounds of the invention in Examples 1-185 below were prepared by the methods described above:

| Ex. # | Structure | Mass ES(+) | Systematic Name | Amine Reagent | Other Reagent | Method |
|---|---|---|---|---|---|---|
| 1 | 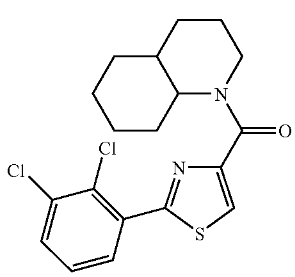 | 394 | [2-(2,3-Dichloro-phenyl)-thiazol-4-yl]-(octahydro-quinolin-1-yl)-methanone | Decahydro-quinoline | 2-(2,3-Dichloro-phenyl)-thiazole-4-carboxylic acid | Method A |
| 2 | 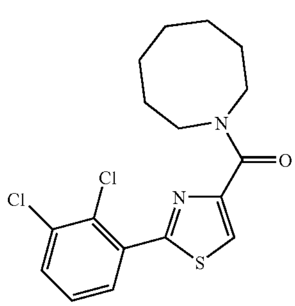 | 368 | Azocan-1-yl-[2-(2,3-dichloro-phenyl)-thiazol-4-yl]-methanone | Azocane | 2-(2,3-Dichloro-phenyl)-thiazole-4-carboxylic acid | Method D |

| Ex. # | Structure | Mass ES(+) | Systematic Name | Amine Reagent | Other Reagent | Method |
|---|---|---|---|---|---|---|
| 3 | 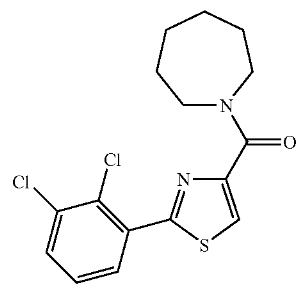 | 354 | Azepan-1-yl-[2-(2,3-dichloro-phenyl)-thiazol-4-yl]-methanone | Azepane | 2-(2,3-Dichloro-phenyl)-thiazole-4-carboxylic acid | Method D |
| 4 | 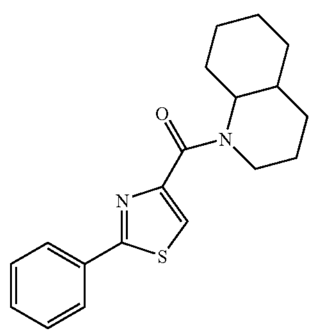 | 326 | (Octahydro-quinolin-1-yl)-(2-phenyl-thiazol-4-yl)-methanone | Decahydro-quinoline | 2-Phenyl-thiazole-4-carboxylic acid | Method D |
| 5 | 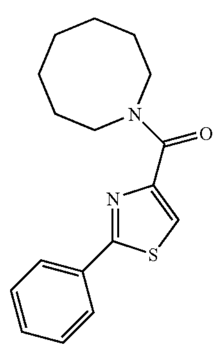 | 300 | Azocan-1-yl-(2-phenyl-thiazol-4-yl)-methanone | azocane | 2-Phenyl-thiazole-4-carboxylic acid | Method D |
| 6 | 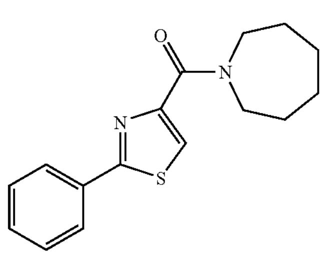 | 286 | Azepan-1-yl-(2-phenyl-thiazol-4-yl)-methanone | azepane | 2-Phenyl-thiazole-4-carboxylic acid | Method D |

-continued

| Ex. # | Structure | Mass ES(+) | Systematic Name | Amine Reagent | Other Reagent | Method |
|---|---|---|---|---|---|---|
| 7 | 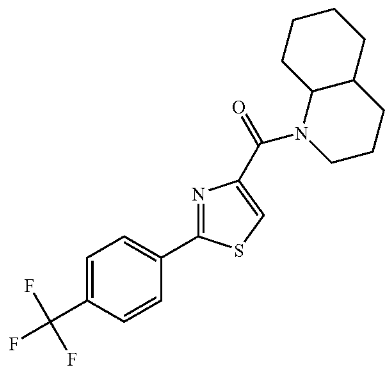 | 394 | (Octahydro-quinolin-1-yl)-[2-(4-trifluoro-methyl-phenyl)-thiazol-4-yl]-methanone | decahydro-quinoline | 2-(4-trifluoromethyl-phenyl)-thiazole-4-carboxylic acid | Method D |
| 8 | 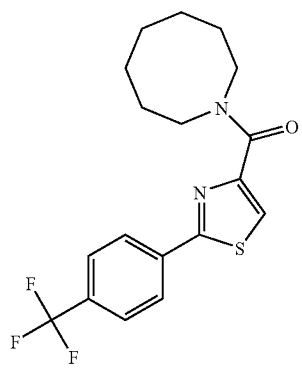 | 368 | Azocan-1-yl-[2-(4-trifluoro-methyl-phenyl)-thiazol-4-yl]-methanone | azocane | 2-(4-trifluoromethyl-phenyl)-thiazole-4-carboxylic acid | Method D |
| 9 | 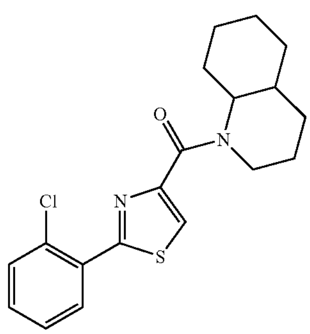 | 360 | [2-(2-Chloro-phenyl)-thiazol-4-yl]-(octahydro-quinolin-1-yl)-methanone | decahydro-quinoline | 2-(2-Chloro-phenyl)-thiazole-4-carboxylic acid | Method D |
| 10 | 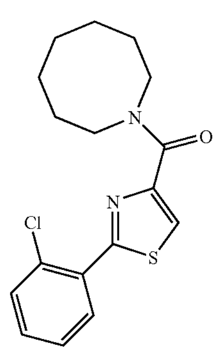 | 334 | Azocan-1-yl-[2-(2-chloro-phenyl)-thiazol-4-yl]-methanone | azocane | 2-(2-Chloro-phenyl)-thiazole-4-carboxylic acid | Method D |

| Ex. # | Structure | Mass ES(+) | Systematic Name | Amine Reagent | Other Reagent | Method |
|---|---|---|---|---|---|---|
| 11 | 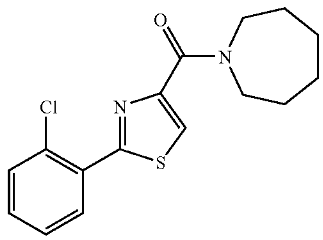 | 320 | Azepan-1-yl-[2-(2-chloro-phenyl)-thiazol-4-yl]-methanone | azepane | 2-(2-Chloro-phenyl)-thiazole-4-carboxylic acid | Method D |
| 12 | 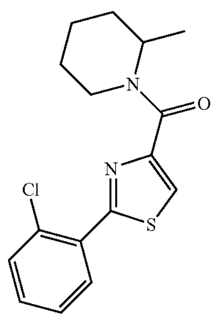 | 320 | [2-(2-Chloro-phenyl)-thiazol-4-yl]-(2-methyl-piperidin-1-yl)-methanone | 2-methyl piperidine | 2-(2-Chloro-phenyl)-thiazole-4-carboxylic acid | Method D |
| 13 | 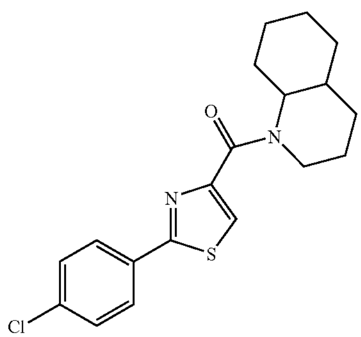 | 360 | [2-(4-Chloro-phenyl)-thiazol-4-yl]-(octahydro-quinolin-1-yl)-methanone | decahydro-quinoline | 2-(4-Chloro-phenyl)-thiazole-4-carboxylic acid | Method D |
| 14 | 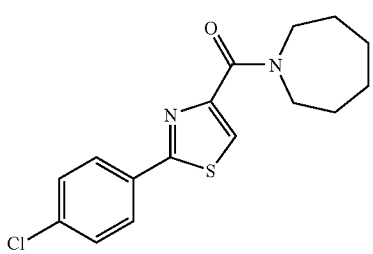 | 320 | Azepan-1-yl-[2-(4-chloro-phenyl)-thiazol-4-yl]-methanone | azepane | 2-(4-Chloro-phenyl)-thiazole-4-carboxylic acid | Method D |
| 15 | 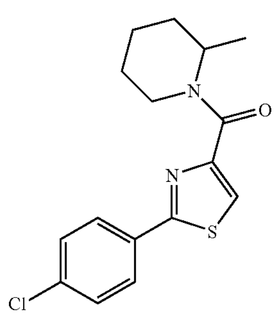 | 320 | [2-(4-Chloro-phenyl)-thiazol-4-yl]-(2-methyl-piperidin-1-yl)-methanone | 2-methyl piperidine | 2-(4-Chloro-phenyl)-thiazole-4-carboxylic acid | Method D |

-continued

| Ex. # | Structure | Mass ES(+) | Systematic Name | Amine Reagent | Other Reagent | Method |
|---|---|---|---|---|---|---|
| 16 | 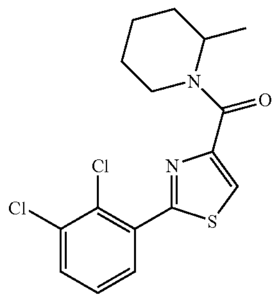 | 354 | [2-(2,3-Dichloro-phenyl)-thiazol-4-yl]-(2-methyl-piperidin-1-yl)-methanone | 2-methyl piperidine | 2-(2,3-Dichloro-phenyl)-thiazole-4-carboxylic acid | Method D |
| 17 | 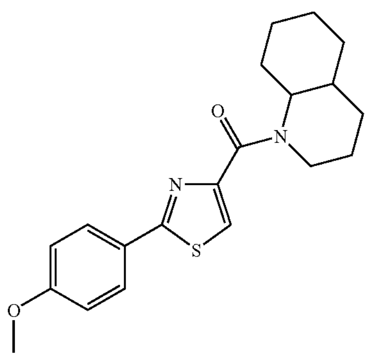 | 356 | [2-(4-Methoxy-phenyl)-thiazol-4-yl]-(octahydro-quinolin-1-yl)-methanone | decahydro-quinoline | 2-(4-methoxy-butyl-phenyl)-thiazole-4-carboxylic acid | Method D |
| 18 | 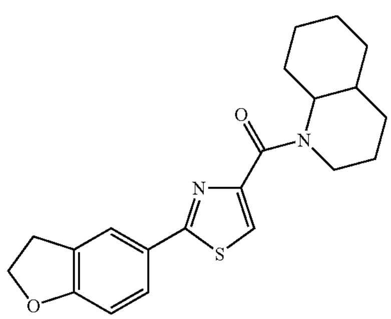 | 368 | [2-(2,3-Dihydro-benzofuran-5-yl)-thiazol-4-yl]-(octahydro-quinolin-1-yl)-methanone | decahydro-quinoline | 2,3-Dihydro-benzofuran-5-carbothioic acid amide | Method D |
| 19 | 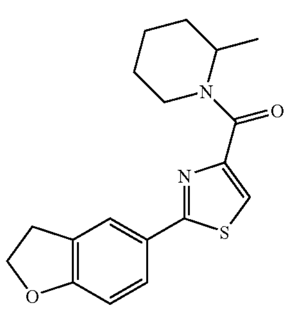 | 328 | [2-(2,3-Dihydro-benzofuran-5-yl)-thiazol-4-yl]-(2-methyl-piperidin-1-yl)-methanone | 2-methyl piperidine | 2,3-Dihydro-benzofuran-5-carbothioic acid amide | Method D |

-continued

| Ex. # | Structure | Mass ES(+) | Systematic Name | Amine Reagent | Other Reagent | Method |
|---|---|---|---|---|---|---|
| 20 | 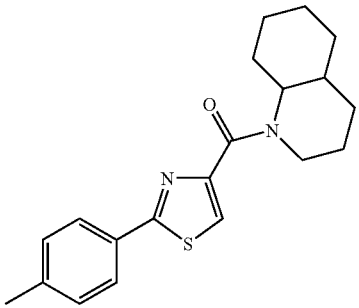 | 340 | (Octahydro-quinolin-1-yl)-(2-p-tolyl-thiazol-4-yl)-methanone | decahydro-quinoline | 2-(4-methyl-phenyl)-thiazole-4-carboxylic acid | Method D |
| 21 | 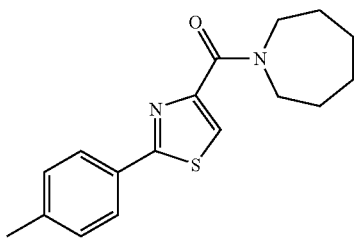 | 300 | Azepan-1-yl-(2-p-tolyl-thiazol-4-yl)-methanone | azepane | 2-(4-methyl-phenyl)-thiazole-4-carboxylic acid | Method D |
| 22 | 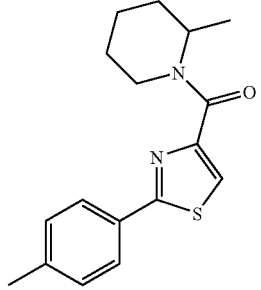 | 300 | (2-Methyl-piperidin-1-yl)-(2-p-tolyl-thiazol-4-yl)-methanone | 2-methyl piperidine | 4-methyl-phenyl-boronic acid | Method F |
| 23 | 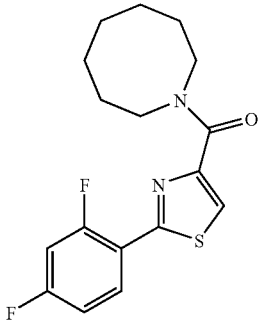 | 336 | Azocan-1-yl-[2-(2,4-difluoro-phenyl)-thiazol-4-yl]-methanone | azocane | 2-(2,4-Difluoro-phenyl)-thiazole-4-carboxylic acid | Method D |
| 24 | 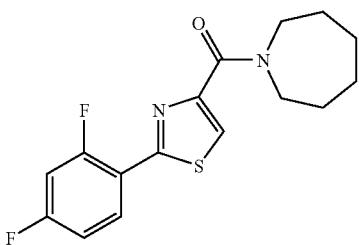 | 322 | Azepan-1-yl-[2-(2,4-difluoro-phenyl)-thiazol-4-yl]-methanone | azepane | 2-(2,4-Difluoro-phenyl)-thiazole-4-carboxylic acid | Method D |

-continued

| Ex. # | Structure | Mass ES(+) | Systematic Name | Amine Reagent | Other Reagent | Method |
|---|---|---|---|---|---|---|
| 25 | 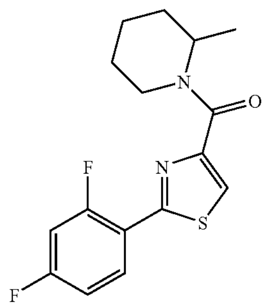 | 322 | [2-(2,4-Difluoro-phenyl)-thiazol-4-yl]-(2-methyl-piperidin-1-yl)-methanone | 2-methyl piperidine | 2-(2,4-Difluoro-phenyl)-thiazole-4-carboxylic acid | Method D |
| 26 | 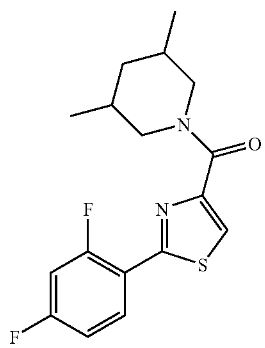 | 336 | [2-(2,4-Difluoro-phenyl)-thiazol-4-yl]-(3,5-dimethyl-piperidin-1-yl)-methanone | 3,5-dimethyl piperidine | 2-(2,4-Difluoro-phenyl)-thiazole-4-carboxylic acid | Method D |
| 27 | 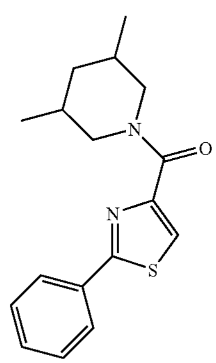 | 300 | (3,5-Dimethyl-piperidin-1-yl)-(2-phenyl-thiazol-4-yl)-methanone | 3,5-dimethyl piperidine | 2-Phenyl-thiazole-4-carboxylic acid | Method D |
| 28 | 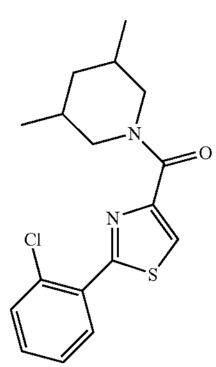 | 334 | [2-(2-Chloro-phenyl)-thiazol-4-yl]-(3,5-dimethyl-piperidin-1-yl)-methanone | 3,5-dimethyl piperidine | 2-(2-Chloro-phenyl)-thiazole-4-carboxylic acid | Method D |

-continued

| Ex. # | Structure | Mass ES(+) | Systematic Name | Amine Reagent | Other Reagent | Method |
|---|---|---|---|---|---|---|
| 29 | 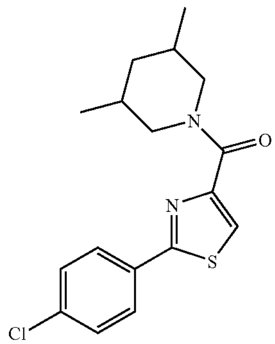 | 334 | [2-(4-Chloro-phenyl)-thiazol-4-yl]-(3,5-dimethyl-piperidin-1-yl)-methanone | 3,5-dimethyl piperidine | 2-(4-Chloro-phenyl)-thiazole-4-carboxylic acid | Method D |
| 30 | 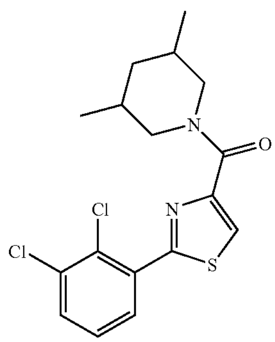 | 368 | [2-(2,3-Dichloro-phenyl)-thiazol-4-yl]-(3,5-dimethyl-piperidin-1-yl)-methanone | 3,5-dimethyl piperidine | 2-(2,3-Dichloro-phenyl)-thiazole-4-carboxylic acid | Method D |
| 31 | 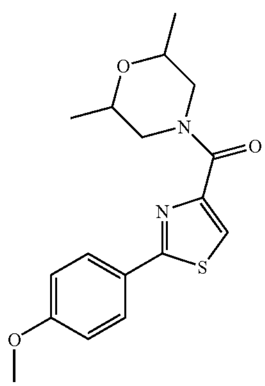 | 332 | (2,6-Dimethyl-morpholin-4-yl)-[2-(4-methoxy-phenyl)-thiazol-4-yl]-methanone | 2,6-dimethyl-morpholine | 2-(4-methoxy-butyl-phenyl)-thiazole-4-carboxylic acid | Method D |
| 32 | 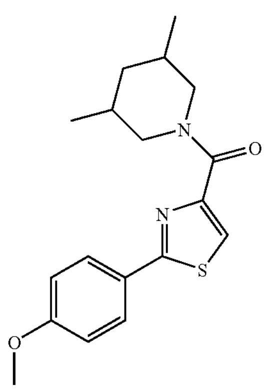 | 330 | (3,5-Dimethyl-piperidin-1-yl)-[2-(4-methoxy-phenyl)-thiazol-4-yl]-methanone | 3,5-dimethyl piperidine | 2-(4-methoxy-butyl-phenyl)-thiazole-4-carboxylic acid | Method D |

-continued

| Ex. # | Structure | Mass ES(+) | Systematic Name | Amine Reagent | Other Reagent | Method |
|---|---|---|---|---|---|---|
| 33 | 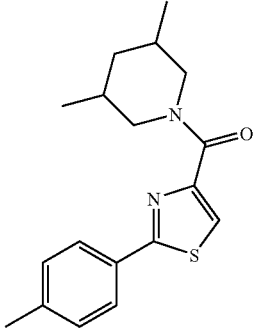 | 314 | (3,5-Dimethyl-piperidin-1-yl)-(2-p-tolyl-thiazol-4-yl)-methanone | 3,5-dimethyl piperidine | 2-(4-methyl-phenyl)-thiazole-4-carboxylic acid | Method D |
| 34 | 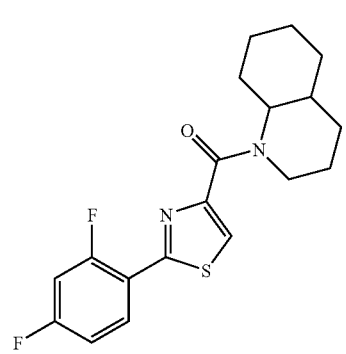 | 362 | [2-(2,4-Difluoro-phenyl)-thiazol-4-yl]-(octahydro-quinolin-1-yl)-methanone | decahydro-quinoline | 2-(2,4-Difluoro-phenyl)-thiazole-4-carboxylic acid | Method D |
| 35 | 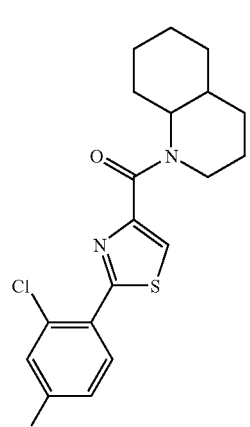 | 360 | [2-(3-Chloro-phenyl)-thiazol-4-yl]-(octahydro-quinolin-1-yl)-methanone | decahydro-quinoline | 3-Chloro-phenylboronic acid | Method F |
| 36 | 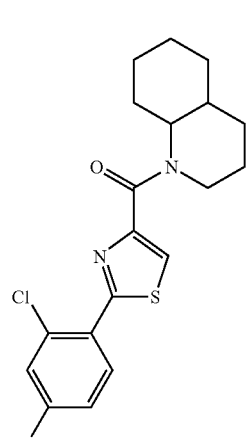 | 394 | [2-(2,4-Dichloro-phenyl)-thiazol-4-yl]-(octahydro-quinolin-1-yl)-methanone | decahydro-quinoline | 2,4-Dichlorophenyl boronic acid | Method F |

-continued

| Ex. # | Structure | Mass ES(+) | Systematic Name | Amine Reagent | Other Reagent | Method |
|---|---|---|---|---|---|---|
| 37 | 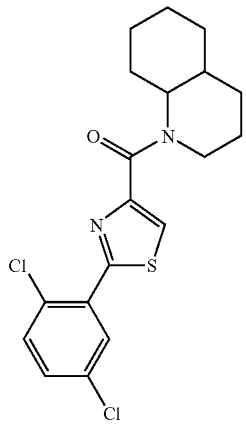 | 394 | [2-(2,5-Dichlorophenyl)-thiazol-4-yl]-(octahydroquinolin-1-yl)-methanone | decahydroquinoline | 2,5-Dichlorophenyl boronic acid | Method F |
| 38 | 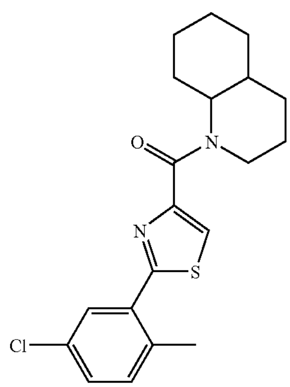 | 374 | [2-(5-Chloro-2-methylphenyl)-thiazol-4-yl]-(octahydroquinolin-1-yl)-methanone | decahydroquinoline | 3-Chloro-5-methylphenyl boronic acid | Method F |
| 39 | 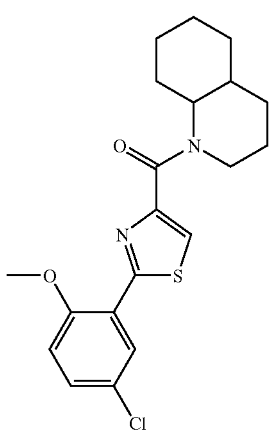 | 390 | [2-(5-Chloro-2-methoxyphenyl)-thiazol-4-yl]-(octahydroquinolin-1-yl)-methanone | decahydroquinoline | 3-Chloro-6-methoxyphenyl boronic acid | Method F |

-continued

| Ex. # | Structure | Mass ES(+) | Systematic Name | Amine Reagent | Other Reagent | Method |
|---|---|---|---|---|---|---|
| 40 | 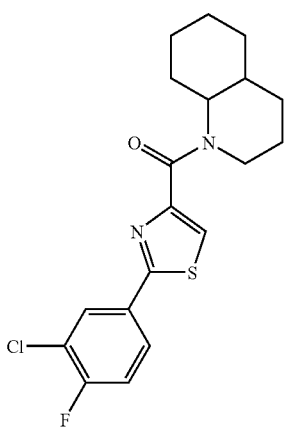 | 378 | [2-(3-Chloro-4-fluoro-phenyl)-thiazol-4-yl]-(octahydro-quinolin-1-yl)-methanone | decahydro-quinoline | 3-Chloro-4-fluorophenyl boronic acid | Method F |
| 41 | 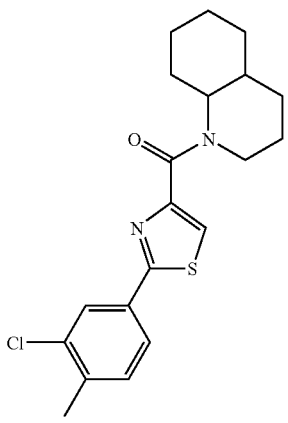 | 374 | [2-(3-Chloro-4-methyl-phenyl)-thiazol-4-yl]-(octahydro-quinolin-1-yl)-methanone | decahydro-quinoline | 3-Chloro-4-methylphenyl boronic acid | Method F |
| 42 | 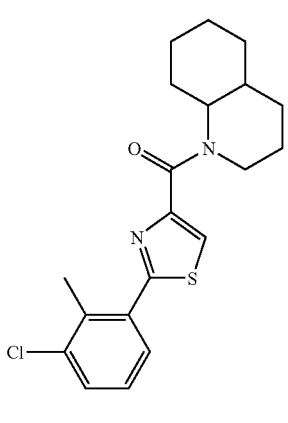 | 374 | [2-(3-Chloro-2-methyl-phenyl)-thiazol-4-yl]-(octahydro-quinolin-1-yl)-methanone | decahydro-quinoline | 3-Chloro-2-methylphenyl boronic acid | Method F |

-continued

| Ex. # | Structure | Mass ES(+) | Systematic Name | Amine Reagent | Other Reagent | Method |
|---|---|---|---|---|---|---|
| 43 | 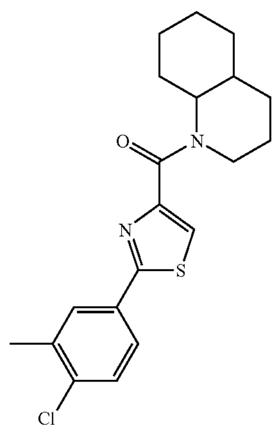 | 374 | [2-(4-Chloro-3-methyl-phenyl)-thiazol-4-yl]-(octahydro-quinolin-1-yl)-methanone | decahydro-quinoline | 4-Chloro-3-methylphenyl boronic acid | Method F |
| 44 | 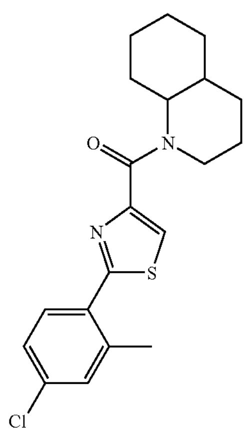 | 374 | [2-(4-Chloro-2-methyl-phenyl)-thiazol-4-yl]-(octahydro-quinolin-1-yl)-methanone | decahydro-quinoline | 4-Chloro-2-methylphenyl boronic acid | Method F |
| 45 | 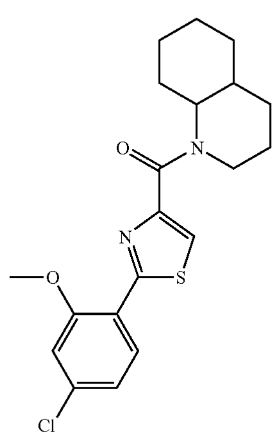 | 390 | [2-(4-Chloro-2-methoxy-phenyl)-thiazol-4-yl]-(octahydro-quinolin-1-yl)-methanone | decahydro-quinoline | 4-Chloro-2-methoxylphenyl boronic acid | Method F |

-continued

| Ex. # | Structure | Mass ES(+) | Systematic Name | Amine Reagent | Other Reagent | Method |
|---|---|---|---|---|---|---|
| 46 | 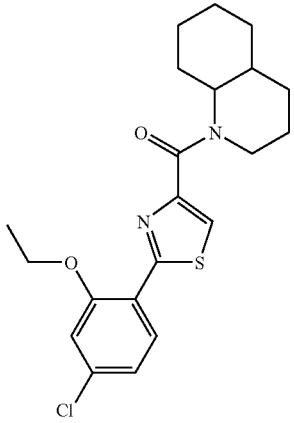 | 404 | [2-(4-Chloro-2-ethoxy-phenyl)-thiazol-4-yl]-(octahydro-quinolin-1-yl)-methanone | decahydro-quinoline | 4-Chloro-2-ethoxylphenyl boronic acid | Method F |
| 47 | 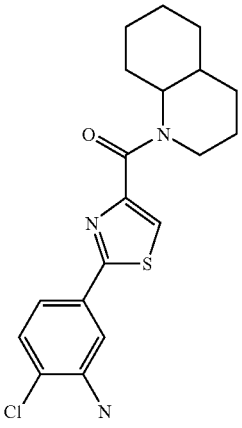 | 375 | [2-(3-Amino-4-chloro-phenyl)-thiazol-4-yl]-(octahydro-quinolin-1-yl)-methanone | decahydro-quinoline | 4-Chloro-3-aminophenyl boronic acid | Method F |
| 48 | 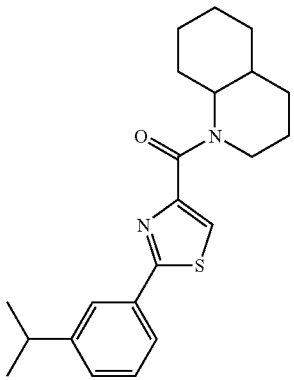 | 368 | [2-(3-Isopropyl-phenyl)-thiazol-4-yl]-(octahydro-quinolin-1-yl)-methanone | decahydro-quinoline | 3-Isopropylphenyl boronic acid | Method F |

-continued

| Ex. # | Structure | Mass ES(+) | Systematic Name | Amine Reagent | Other Reagent | Method |
|---|---|---|---|---|---|---|
| 49 | 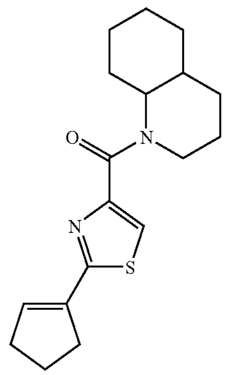 | 316 | (2-Cyclopent-1-enyl-thiazol-4-yl)-(octahydro-quinolin-1-yl)-methanone | decahydro-quinoline | Cyclopenten-1-ylboronic acid | Method F |
| 50 | 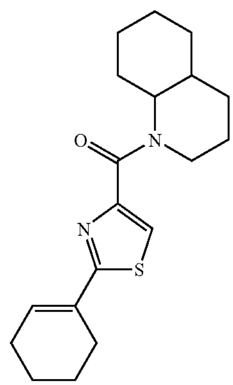 | 330 | (2-Cyclohex-1-enyl-thiazol-4-yl)-(octahydro-quinolin-1-yl)-methanone | decahydro-quinoline | Cyclohexen-1-ylboronic acid | Method F |
| 51 | 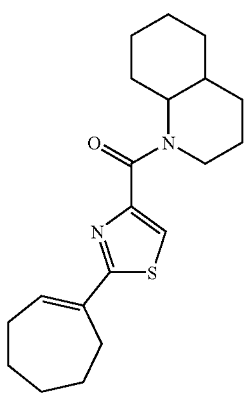 | 344 | (2-Cyclohept-1-enyl-thiazol-4-yl)-(octahydro-quinolin-1-yl)-methanone | decahydro-quinoline | Cyclohepten-1-ylboronic acid | Method F |
| 52 | 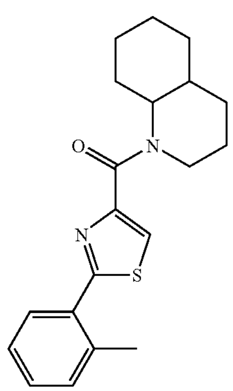 | 340 | (Octahydro-quinolin-1-yl)-(2-o-tolyl-thiazol-4-yl)-methanone | decahydro-quinoline | 2-Methylphenyl boronic acid | Method F |

-continued

| Ex. # | Structure | Mass ES(+) | Systematic Name | Amine Reagent | Other Reagent | Method |
|---|---|---|---|---|---|---|
| 53 | 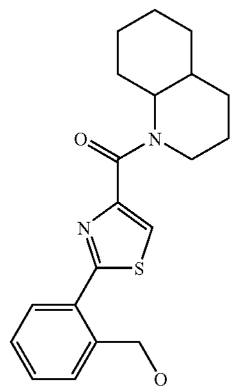 | 356 | [2-(2-Hydroxy-methyl-phenyl)-thiazol-4-yl]-(octahydro-quinolin-1-yl)-methanone | decahydro-quinoline | (2-Hydroxymethyl phenyl)boronic acid dehydrate | Method F |
| 54 | 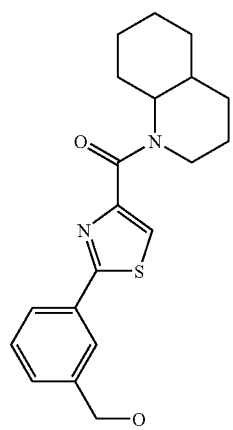 | 356 | [2-(3-Hydroxy-methyl-phenyl)-thiazol-4-yl]-(octahydro-quinolin-1-yl)-methanone | decahydro-quinoline | (3-Hydroxymethyl phenyl)boronic acid dehydrate | Method F |
| 55 | 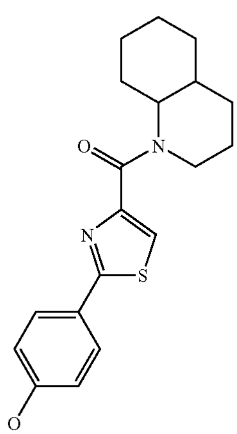 | 342 | [2-(4-Hydroxy-phenyl)-thiazol-4-yl]-(octahydro-quinolin-1-yl)-methanone | decahydro-quinoline | 4-Hydroxyphenyl boronic acid dehydrate | Method F |

-continued

| Ex. # | Structure | Mass ES(+) | Systematic Name | Amine Reagent | Other Reagent | Method |
|---|---|---|---|---|---|---|
| 56 | 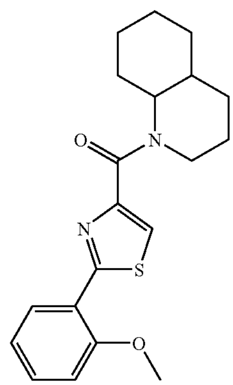 | 356 | [2-(2-Methoxy-phenyl)-thiazol-4-yl]-(octahydro-quinolin-1-yl)-methanone | decahydro-quinoline | 2-Methoxyphenyl boronic acid | Method F |
| 57 | 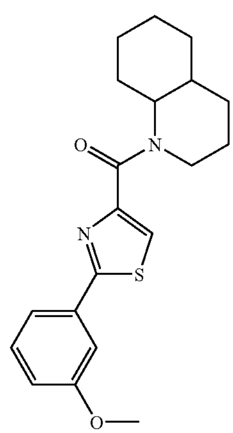 | 356 | [2-(3-Methoxy-phenyl)-thiazol-4-yl]-(octahydro-quinolin-1-yl)-methanone | decahydro-quinoline | 3-Methoxyphenyl boronic acid | Method F |
| 58 | 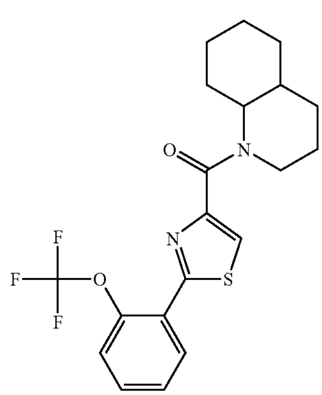 | 410 | (Octahydro-quinolin-1-yl)-[2-(2-trifluoro-methoxy-phenyl)-thiazol-4-yl]-methanone | decahydro-quinoline | 2-Trifluoro-methoxyphenyl boronic acid | Method F |

-continued

| Ex. # | Structure | Mass ES(+) | Systematic Name | Amine Reagent | Other Reagent | Method |
|---|---|---|---|---|---|---|
| 59 | 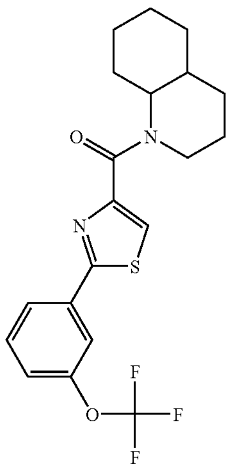 | 410 | (Octahydro-quinolin-1-yl)-[2-(3-trifluoro-methoxy-phenyl)-thiazol-4-yl]-methanone | decahydro-quinoline | 3-Trifluoro-methoxyphenyl boronic acid | Method F |
| 60 | 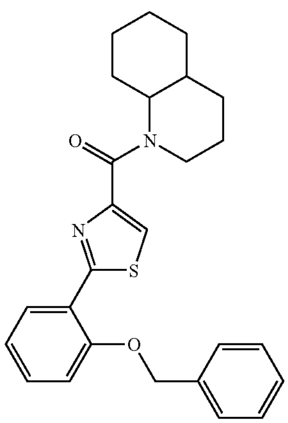 | 432 | [2-(2-Benzyloxy-phenyl)-thiazol-4-yl]-(octahydro-quinolin-1-yl)-methanone | decahydro-quinoline | 2-Benzyloxy-phenylboronic acid | Method F |
| 61 | 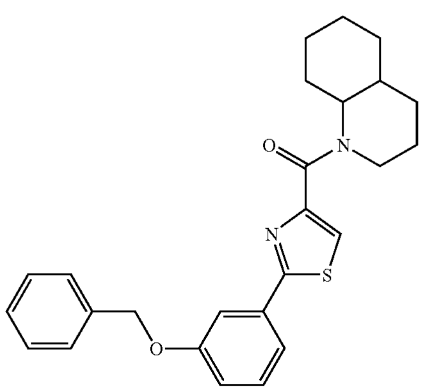 | 432 | [2-(3-Benzyloxy-phenyl)-thiazol-4-yl]-(octahydro-quinolin-1-yl)-methanone | decahydro-quinoline | 3-Benzyloxy-phenylboronic acid | Method F |

-continued

| Ex. # | Structure | Mass ES(+) | Systematic Name | Amine Reagent | Other Reagent | Method |
|---|---|---|---|---|---|---|
| 62 | 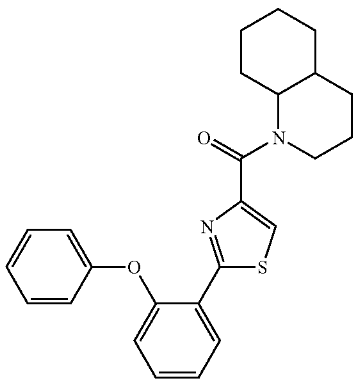 | 418 | (Octahydro-quinolin-1-yl)-[2-(2-phenoxy-phenyl)-thiazol-4-yl]-methanone | decahydro-quinoline | (2-Phenoxy)phenyl boronic acid | Method F |
| 63 | 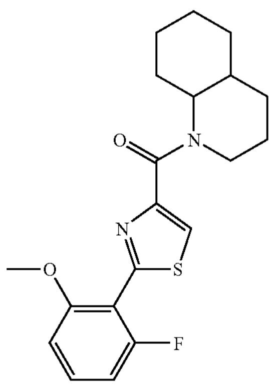 | 374 | [2-(2-Fluoro-6-methoxy-phenyl)-thiazol-4-yl]-(octahydro-quinolin-1-yl)-methanone | decahydro-quinoline | 6-Fluoro-2-methoxyphenyl boronic acid | Method F |
| 64 | 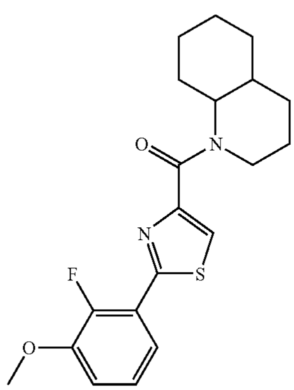 | 374 | [2-(2-Fluoro-3-methoxy-phenyl)-thiazol-4-yl]-(octahydro-quinolin-1-yl)-methanone | decahydro-quinoline | 2-Fluoro-3-methoxyphenyl boronic acid | Method F |
| 65 | 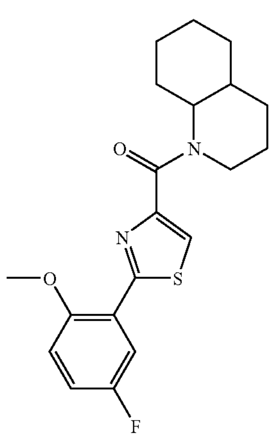 | 374 | [2-(5-Fluoro-2-methoxy-phenyl)-thiazol-4-yl]-(octahydro-quinolin-1-yl)-methanone | decahydro-quinoline | 5-Fluoro-2-methoxyphenyl boronic acid | Method F |

| Ex. # | Structure | Mass ES(+) | Systematic Name | Amine Reagent | Other Reagent | Method |
|---|---|---|---|---|---|---|
| 66 | 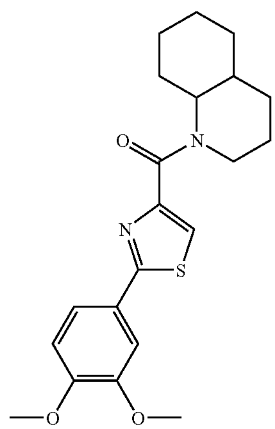 | 386 | [2-(3,4-Dimethoxy-phenyl)-thiazol-4-yl]-(octahydro-quinolin-1-yl)-methanone | decahydro-quinoline | 3,4-Dimethoxy-phenylboronic acid | Method F |
| 67 | 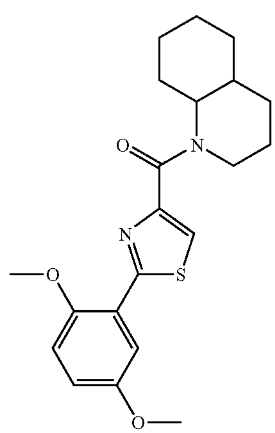 | 386 | [2-(2,5-Dimethoxy-phenyl)-thiazol-4-yl]-(octahydro-quinolin-1-yl)-methanone | decahydro-quinoline | 2,5-Dimethoxy-phenylboronic acid | Method F |
| 68 | 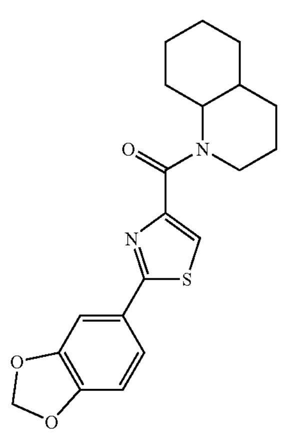 | 370 | (2-Benzo[1,3]dioxol-5-yl-thiazol-4-yl)-(octahydro-quinolin-1-yl)-methanone | decahydro-quinoline | 5-Benzo[1,3]dioxoleboronic acid | Method F |

-continued

| Ex. # | Structure | Mass ES(+) | Systematic Name | Amine Reagent | Other Reagent | Method |
|---|---|---|---|---|---|---|
| 69 | 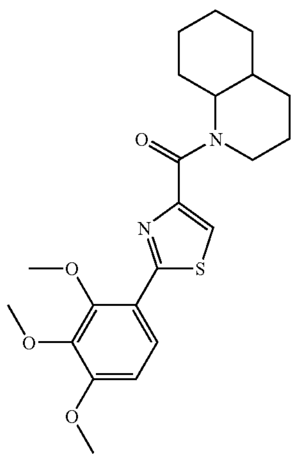 | 416 | (Octahydro-quinolin-1-yl)-[2-(2,3,4-trimethoxy-phenyl)-thiazol-4-yl]-methanone | decahydro-quinoline | 2,3,4-Trimethoxy-phenylboronic acid | Method F |
| 70 | 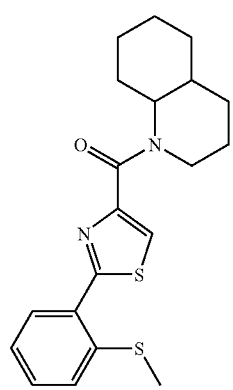 | 372 | [2-(2-Methylsulfanyl-phenyl)-thiazol-4-yl]-(octahydro-quinolin-1-yl)-methanone | decahydro-quinoline | 2-Methylsulfanyl-phenylboronic acid | Method F |
| 71 | 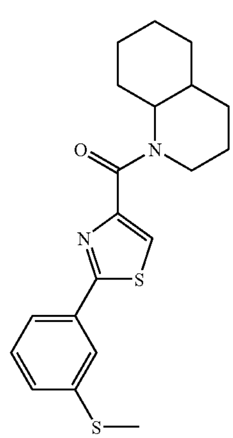 | 372 | [2-(3-Methylsulfanyl-phenyl)-thiazol-4-yl]-(octahydro-quinolin-1-yl)-methanone | decahydro-quinoline | 3-Methylsulfanyl-phenol | Method F |

| Ex. # | Structure | Mass ES(+) | Systematic Name | Amine Reagent | Other Reagent | Method |
|---|---|---|---|---|---|---|
| 72 | 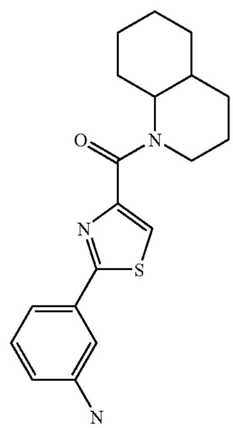 | 341 | [2-(3-Aminophenyl)-thiazol-4-yl]-(octahydroquinolin-1-yl)-methanone | decahydroquinoline | 3-Aminophenyl boronic acid | Method F |
| 73 | 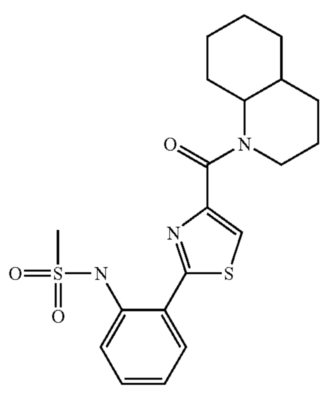 | 419 | N-{2-[4-(Octahydroquinoline-1-carbonyl)-thiazol-2-yl]-phenyl}-methanesulfonamide | decahydroquinoline | N-(2-Phenylboronic acid)-methane sulfonamide | Method F |
| 74 | 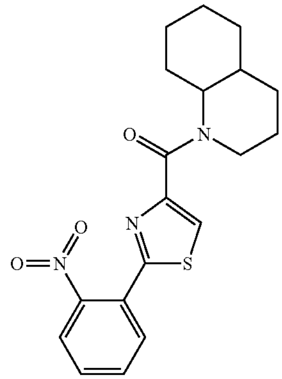 | 371 | [2-(2-Nitrophenyl)-thiazol-4-yl]-(octahydroquinolin-1-yl)-methanone | decahydroquinoline | 2-nitrophenyl boronic acid | Method F |

-continued

| Ex. # | Structure | Mass ES(+) | Systematic Name | Amine Reagent | Other Reagent | Method |
|---|---|---|---|---|---|---|
| 75 | 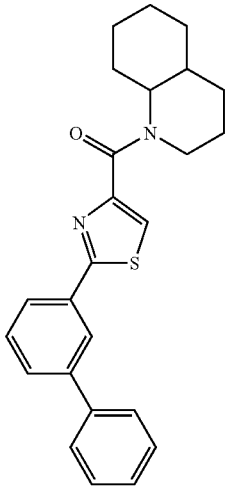 | 402 | (2-Biphenyl-3-yl-thiazol-4-yl)-(octahydro-quinolin-1-yl)-methanone | decahydro-quinoline | 3-phenyl-phenylboronic acid | Method F |
| 76 | 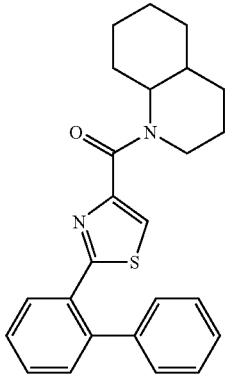 | 402 | (2-Biphenyl-2-yl-thiazol-4-yl)-(octahydro-quinolin-1-yl)-methanone | decahydro-quinoline | 2-phenyl-phenylboronic acid | Method F |
| 77 | 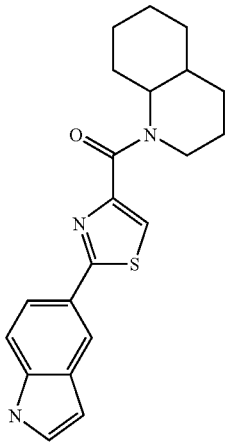 | 365 | [2-(1H-Indol-5-yl)-thiazol-4-yl]-(octahydro-quinolin-1-yl)-methanone | decahydro-quinoline | 1H-Indole-5-boronic acid | Method F |

-continued

| Ex. # | Structure | Mass ES(+) | Systematic Name | Amine Reagent | Other Reagent | Method |
|---|---|---|---|---|---|---|
| 78 | 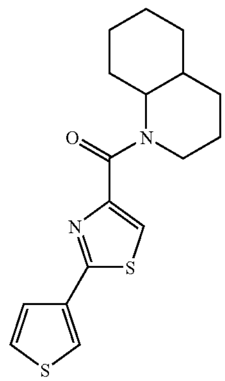 | 332 | (Octahydro-quinolin-1-yl)-(2-thiophen-3-yl-thiazol-4-yl)-methanone | decahydro-quinoline | Thiophene-3-boronic acid | Method F |
| 79 | 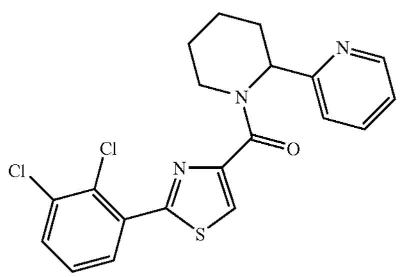 | 417 | [2-(2,3-Dichloro-phenyl)-thiazol-4-yl]-(3,4,5,6-tetrahydro-2H-[2,2']bipyridinyl-1-yl)-methanone | 1,2,3,4,5,6-Hexahydro-[2,2']bipyridine | 2-(2,3-Dichloro-phenyl)-thiazole-4-carboxylic acid | Method B |
| 80 | 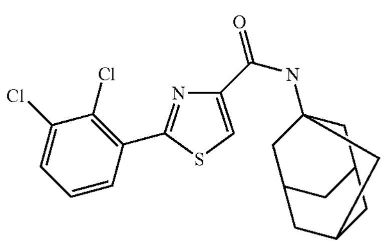 | 406 | 2-(2,3-Dichloro-phenyl)-thiazole-4-carboxylic acid adamantan-1-ylamide | adamantan-1-ylamine | 2-(2,3-Dichloro-phenyl)-thiazole-4-carboxylic acid | Method C |
| 81 | 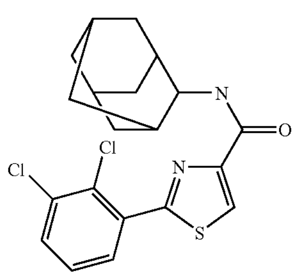 | 406 | 2-(2,3-Dichloro-phenyl)-thiazole-4-carboxylic acid adamantan-2-ylamide | Adamantan-2-ylamine | 2-(2,3-Dichloro-phenyl)-thiazole-4-carboxylic acid | Method B |
| 82 | 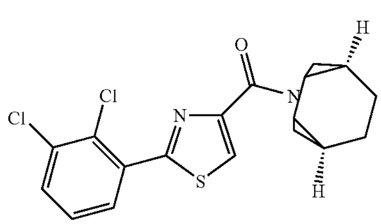 | 380 | (3-Aza-bicyclo[3.2.2]non-3-yl)-[2-(2,3-dichloro-phenyl)-thiazol-4-yl]-methanone | 3-Aza-bicyclo[3.2.2]nonane | 2-(2,3-Dichloro-phenyl)-thiazole-4-carboxylic acid | Method B |

-continued

| Ex. # | Structure | Mass ES(+) | Systematic Name | Amine Reagent | Other Reagent | Method |
|---|---|---|---|---|---|---|
| 83 | 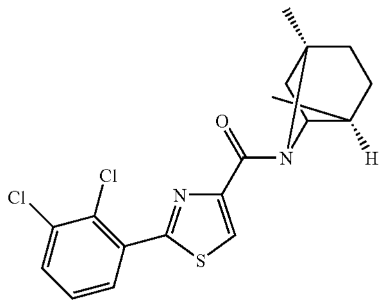 | 408 | 2-(2,3-Dichloro-phenyl)-thiazole-4-carboxylic acid ((1R,4R)-4,7,7-trimethyl-bicyclo[2.2.1]hept-2-yl)-amide | 4,7,7-trimethyl-bicyclo[2.2.1]hept-2-ylamine | 2-(2,3-Dichloro-phenyl)-thiazole-4-carboxylic acid | Method B |
| 84 | 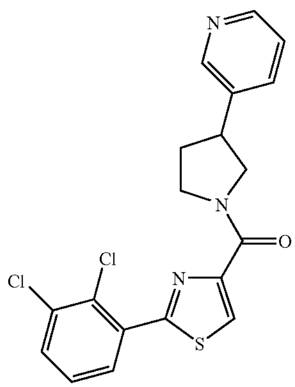 | 403 | [2-(2,3-Dichloro-phenyl)-thiazol-4-yl]-(3-pyridin-3-yl-pyrrolidin-1-yl)-methanone | 3-pyridin-3-yl-pyrrolidine | 2-(2,3-Dichloro-phenyl)-thiazole-4-carboxylic acid | Method B |
| 85 | 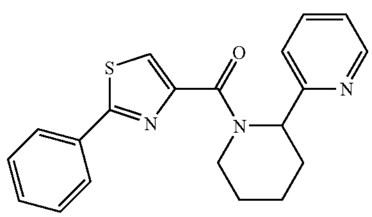 | 349 | (2-Phenyl-thiazol-4-yl)-(3,4,5,6-tetrahydro-2H-[2,2']bipyridinyl-1-yl)-methanone | 1,2,3,4,5,6-Hexahydro-[2,2']bipyridinyl | 2-Phenyl-thiazole-4-carboxylic acid | Method B |
| 86 | 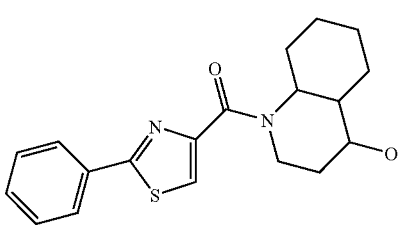 | 360 | (4-Chloro-octahydro-quinolin-1-yl)-(2-phenyl-thiazol-4-yl)-methanone | 4-chlorodecahydro-quinoline | 2-Phenyl-thiazole-4-carboxylic acid | Method B |
| 87 | 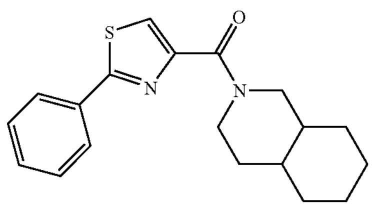 | 326 | (Octahydro-isoquinolin-2-yl)-(2-phenyl-thiazol-4-yl)-methanone | decahydro-isoquinoline | 2-(2,3-Dichloro-phenyl)-thiazole-4-carboxylic acid | Method B |
| 88 | 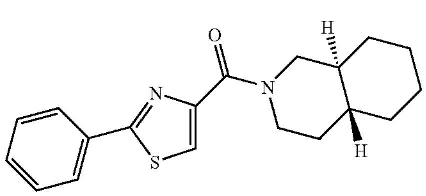 | 326 | (4aR,8aS)-Octahydro-isoquinolin-2-yl-(2-phenyl-thiazol-4-yl)-methanone | trans-decahydro-isoquinoline | 2-(2,3-Dichloro-phenyl)-thiazole-4-carboxylic acid | Method B |

-continued

| Ex. # | Structure | Mass ES(+) | Systematic Name | Amine Reagent | Other Reagent | Method |
|---|---|---|---|---|---|---|
| 89 | 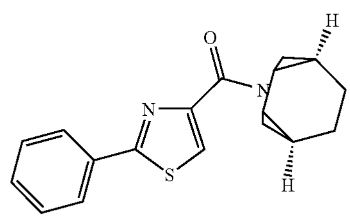 | 312 | (3-Aza-bicyclo[3.2.2]non-3-yl)-(2-phenyl-thiazol-4-yl)-methanone | 3-Aza-bicyclo[3.2.2] nonane | 2-Phenyl-thiazole-4-carboxylic acid | Method B |
| 90 | 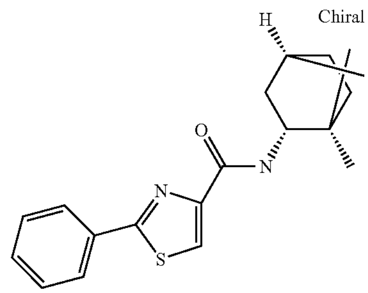 | 340 | 2-Phenyl-thiazole-4-carboxylic acid ((1R,2R,4R)-1,7,7-trimethyl-bicyclo[2.2.1]hept-2-yl)-amide | 1,7,7-trimethyl-bicyclo[2.2.1] hept-2-ylamine | 2-Phenyl-thiazole-4-carboxylic acid | Method B |
| 91 | 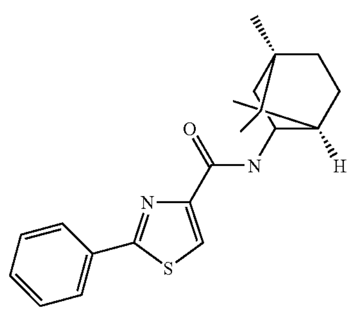 | 340 | 2-Phenyl-thiazole-4-carboxylic acid ((1R,4R)-4,7,7-trimethyl-bicyclo[2.2.1]hept-2-yl)-amide | 4,7,7-trimethyl-bicyclo[2.2.1] hept-2-ylamine | 2-(2,3-Dichloro-phenyl)-thiazole-4-carboxylic acid | Method B |
| 92 | 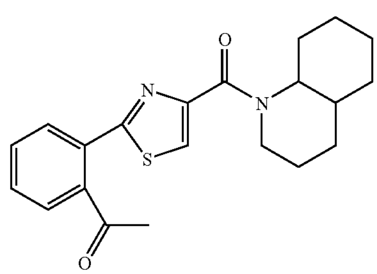 | 368 | 1-{2-[4-(Octahydro-quinoline-1-carbonyl)-thiazol-2-yl]-phenyl}-ethanone | decahydro-quinoline | 2-Acetylphenyl-boronic acid | Method F |
| 93 | 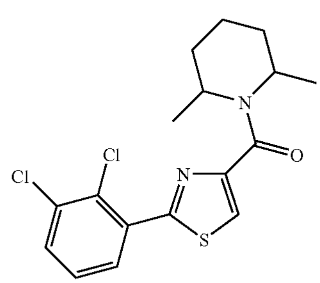 | 368 | [2-(2,3-Dichloro-phenyl)-thiazol-4-yl]-(2,6-dimethyl-piperidin-1-yl)-methanone | 2,6-methyl piperidine | 2-(2,3-Dichloro-phenyl)-thiazole-4-carboxylic acid | Method C |

-continued

| Ex. # | Structure | Mass ES(+) | Systematic Name | Amine Reagent | Other Reagent | Method |
|---|---|---|---|---|---|---|
| 94 | 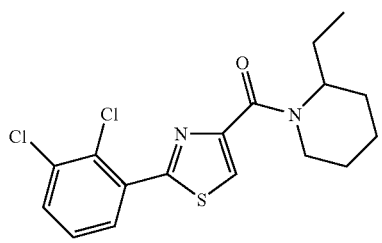 | 368 | [2-(2,3-Dichloro-phenyl)-thiazol-4-yl]-(2-ethyl-piperidin-1-yl)-methanone | 2-ethyl-piperidine | 2-(2,3-Dichloro-phenyl)-thiazole-4-carboxylic acid | Method B |
| 95 | 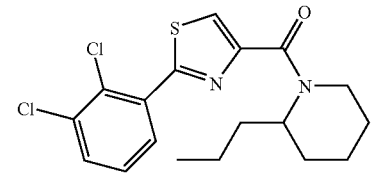 | 382 | [2-(2,3-Dichloro-phenyl)-thiazol-4-yl]-(2-propyl-piperidin-1-yl)-methanone | 2-propyl-piperidine | 2-(2,3-Dichloro-phenyl)-thiazole-4-carboxylic acid | Method B |
| 96 | 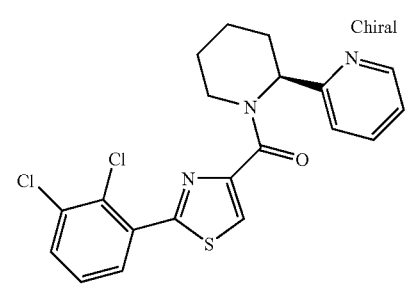 Chiral | 417 | [2-(2,3-Dichloro-phenyl)-thiazol-4-yl]-(S)-3,4,5,6-tetrahydro-2H-[2,2']bipyridinyl-1-yl-methanone | (S)-3,4,5,6-tetrahydro-2H-[2,2']bipyridine | 2-(2,3-Dichloro-phenyl)-thiazole-4-carboxylic acid | Method B |
| 97 | 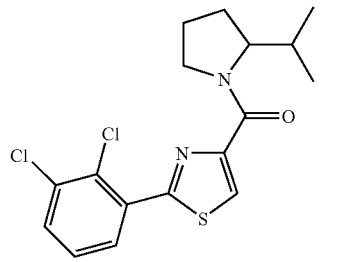 | 368 | [2-(2,3-Dichloro-phenyl)-thiazol-4-yl]-(2-isopropyl-pyrrolidin-1-yl)-methanone | 2-isopropyl-pyrrolidine | 2-(2,3-Dichloro-phenyl)-thiazole-4-carboxylic acid | Method B |
| 98 | 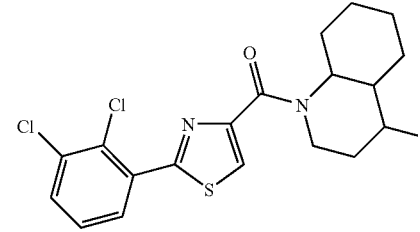 | 428 | (4-Chloro-octahydro-quinolin-1-yl)-[2-(2,3-dichloro-phenyl)-thiazol-4-yl]-methanone | decahydro-quinoline | 2-(2,3-Dichloro-phenyl)-thiazole-4-carboxylic acid | Method B |
| 99 | 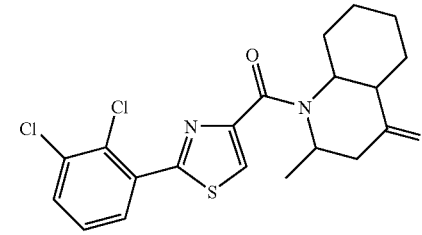 | 422 | 1-[2-(2,3-Dichloro-phenyl)-thiazole-4-carbonyl]-2-methyl-octahydro-quinolin-4-one | decahydro-quinoline | 2-(2,3-Dichloro-phenyl)-thiazole-4-carboxylic acid | Method B |

| Ex. # | Structure | Mass ES(+) | Systematic Name | Amine Reagent | Other Reagent | Method |
|---|---|---|---|---|---|---|
| 100 | 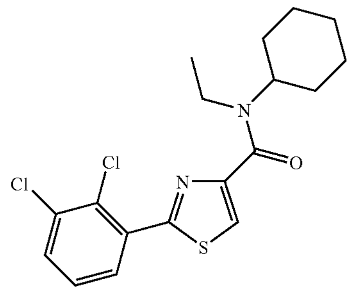 | 382 | 2-(2,3-Dichloro-phenyl)-thiazole-4-carboxylic acid cyclohexyl-ethyl-amide | cyclohexyl-ethyl-amine | 2-(2,3-Dichloro-phenyl)-thiazole-4-carboxylic acid | Method B |
| 101 | 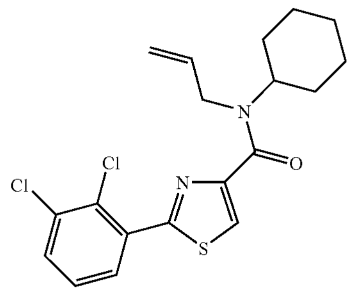 | 394 | 2-(2,3-Dichloro-phenyl)-thiazole-4-carboxylic acid allyl-cyclohexyl-amide | allyl-cyclohexyl-amine | 2-(2,3-Dichloro-phenyl)-thiazole-4-carboxylic acid | Method B |
| 102 | 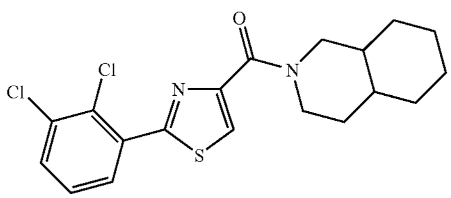 | 394 | [2-(2,3-Dichloro-phenyl)-thiazol-4-yl]-(octahydro-isoquinolin-2-yl)-methanone | Decahydro isoquinoline | 2-(2,3-Dichloro-phenyl)-thiazole-4-carboxylic acid | Method B |
| 103 | 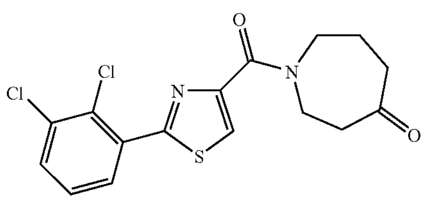 | 368 | 1-[2-(2,3-Dichloro-phenyl)-thiazole-4-carbonyl]-azepan-4-one | azepan-4-one | 2-(2,3-Dichloro-phenyl)-thiazole-4-carboxylic acid | Method B |
| 104 | 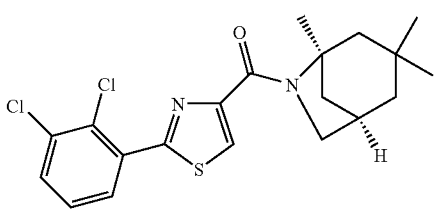 | 408 | [2-(2,3-Dichloro-phenyl)-thiazol-4-yl]-((1R,5R)-3,3,5-trimethyl-6-aza-bicyclo[3.2.1]oct-6-yl)-methanone | 3,3,5-Trimethyl-6-aza-bicyclo[3.2.1] octane | 2-(2,3-Dichloro-phenyl)-thiazole-4-carboxylic acid | Method B |
| 105 | 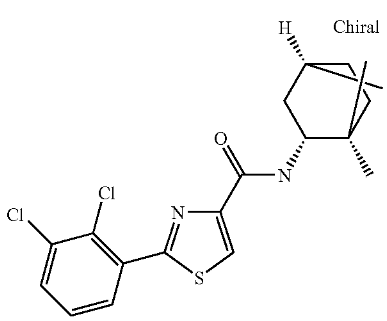 | 408 | 2-(2,3-Dichloro-phenyl)-thiazole-4-carboxylic acid ((1R,2R,4R)-1,7,7-trimethyl-bicyclo]2.2.1]hept-2-yl)-amide | 1,7,7-trimethyl-bicyclo[2.2.1] hept-2-ylamine | 2-(2,3-Dichloro-phenyl)-thiazole-4-carboxylic acid | Method B |

-continued

| Ex. # | Structure | Mass ES(+) | Systematic Name | Amine Reagent | Other Reagent | Method |
|---|---|---|---|---|---|---|
| 106 | 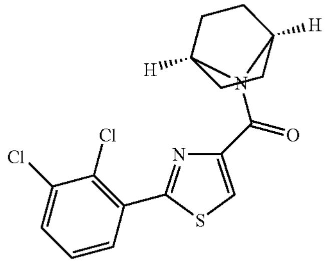 | 352 | (7-Aza-bicyclo[2.2.1]hept-7-yl)-[2-(2,3-dichloro-phenyl)-thiazol-4-yl]-methanone | 7-Aza-bicyclo[2.2.1]heptane | 2-(2,3-Dichloro-phenyl)-thiazole-4-carboxylic acid | Method B |
| 107 | 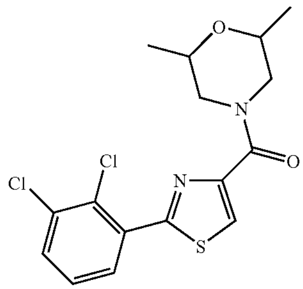 | 370 | [2-(2,3-Dichloro-phenyl)-thiazol-4-yl]-(2,6-dimethyl-morpholin-4-yl)-methanone | 2,6-dimethyl-morpholine | 2-(2,3-Dichloro-phenyl)-thiazole-4-carboxylic acid | Method B |
| 108 | 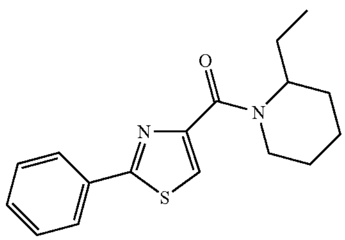 | 300 | (2-Ethyl-piperidin-1-yl)-(2-phenyl-thiazol-4-yl)-methanone | 2-ethyl-piperidine | 2-Phenyl-thiazole-4-carboxylic acid | Method B |
| 109 | Chiral | 349 | (2-Phenyl-thiazol-4-yl)-(S)-3,4,5,6-tetrahydro-2H-[2,2']bipyridinyl-1-yl-methanone | 2(S)-,2,3,4,5,6-Hexahydro-[2,2']bipyridinyl | 2-Phenyl-thiazole-4-carboxylic acid | Method B |
| 110 | 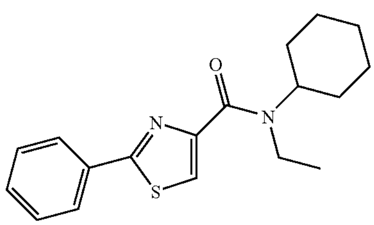 | 314 | 2-Phenyl-thiazole-4-carboxylic acid cyclohexyl-ethyl-amide | cyclohexyl-ethyl-amine | 2-Phenyl-thiazole-4-carboxylic acid | Method B |
| 111 | 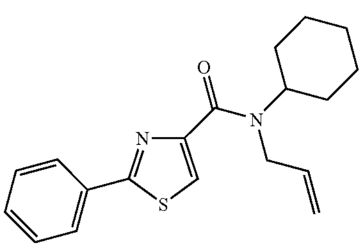 | 326 | 2-Phenyl-thiazole-4-carboxylic acid allyl-cyclohexyl-amide | allyl-cyclohexyl-amine | 2-Phenyl-thiazole-4-carboxylic acid | Method B |

-continued

| Ex. # | Structure | Mass ES(+) | Systematic Name | Amine Reagent | Other Reagent | Method |
|---|---|---|---|---|---|---|
| 112 | 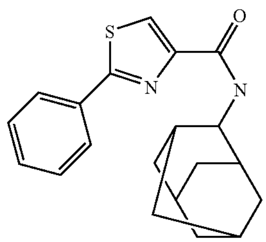 | 338 | 2-Phenyl-thiazole-4-carboxylic acid adamantan-2-ylamide | -hexahydro-furo[3,2-c]quinoline | 2-Phenyl-thiazole-4-carboxylic acid | Method B |
| 113 | 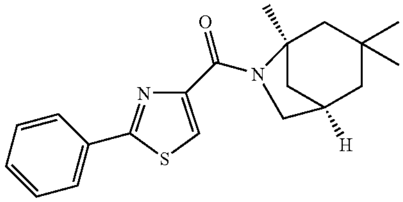 | 340 | (2-Phenyl-thiazol-4-yl)-((1R,5R)-3,3,5-trimethyl-6-aza-bicyclo[3.2.1]oct-6-yl)-methanone | 3,3,5-Trimethyl-6-aza-bicyclo[3.2.1]octane | 2-Phenyl-thiazole-4-carboxylic acid | Method B |
| 114 | 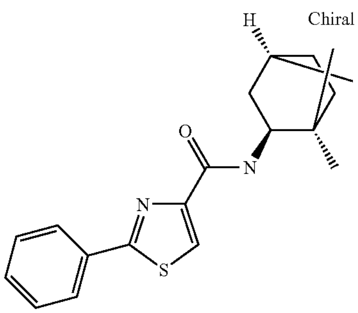 | 340 | 2-Phenyl-thiazole-4-carboxylic acid ((1R,2S,4R)-1,7,7-trimethyl-bicyclo[2.2.1]hept-2-yl)-amide | 1,7,7-Trimethyl-bicyclo[2.2.1]hept-2-ylamine | 2-Phenyl-thiazole-4-carboxylic acid | Method B |
| 115 | 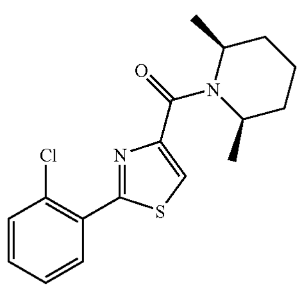 | 334 | [2-(2-Chloro-phenyl)-thiazol-4-yl]-((2S,6R)-2,6-dimethyl-piperidin-1-yl)-methanone | (2S,6R)-2,6-dimethyl-piperidine | 2-chloro-phenyl-boronic acid | Method F |
| 116 | 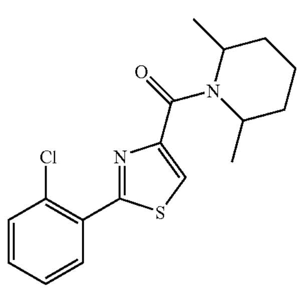 | 334 | [2-(2-Chloro-phenyl)-thiazol-4-yl]-(2,6-dimethyl-piperidin-1-yl)-methanone | 2,6-dimethyl-piperidine | 2-chloro-phenyl-boronic acid | Method F |

| Ex. # | Structure | Mass ES(+) | Systematic Name | Amine Reagent | Other Reagent | Method |
|---|---|---|---|---|---|---|
| 117 | 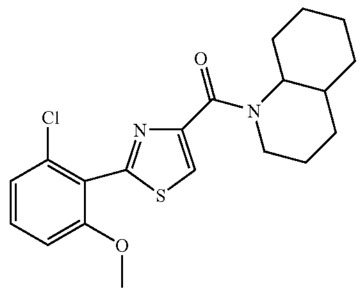 | 390 | [2-(2-Chloro-6-methoxy-phenyl)-thiazol-4-yl]-(octahydro-quinolin-1-yl)-methanone | decahydro-quinoline | 3-CHLORO-6-METHOXY-PHENYL-BORONIC ACID | Method F |
| 118 | 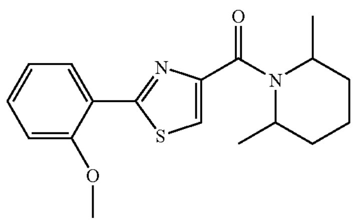 | 330 | (2,6-Dimethyl-piperidin-1-yl)-[2-(2-methoxy-phenyl)-thiazol-4-yl]-methanone | 2,6-dimethyl-morpholine | 2-methoxy-phenyl-boronic acid | Method E |
| 119 | 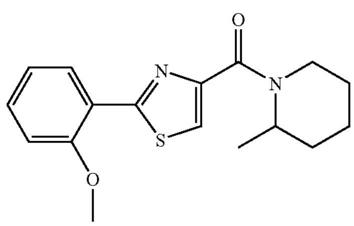 | 316 | [2-(2-Methoxy-phenyl)-thiazol-4-yl]-(2-methyl-piperidin-1-yl)-methanone | 2-methyl piperidine | 2-methoxyphenyl boronic acid | Method F |
| 120 | 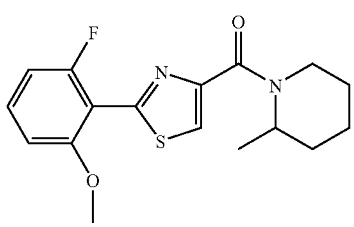 | 334 | [2-(2-Fluoro-6-methoxy-phenyl)-thiazol-4-yl]-(2-methyl-piperidin-1-yl)-methanone | 2-methyl piperidine | 2-fluoro-3-methoxyphenyl boronic acid | Method E |
| 121 | 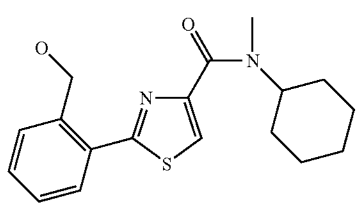 | 330 | 2-(2-Hydroxymethyl-phenyl)-thiazole-4-carboxylic acid cyclohexyl-methyl-amide | cyclohexyl-methyl-amine | 2-hydroxymethyl-phenyl-boronic acid | Method E |
| 122 | 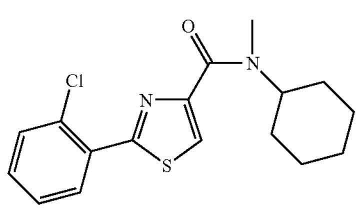 | 334 | 2-(2-Chloro-phenyl)-thiazole-4-carboxylic acid cyclohexyl-methyl-amide | cyclohexyl-methyl-amine | 2-chloro-phenyl-boronic acid | Method E |

-continued

| Ex. # | Structure | Mass ES(+) | Systematic Name | Amine Reagent | Other Reagent | Method |
|---|---|---|---|---|---|---|
| 123 | 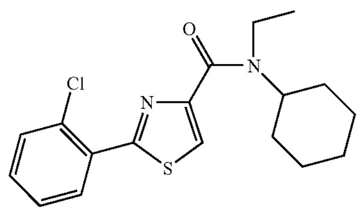 | 348 | 2-(2-Chloro-phenyl)-thiazole-4-carboxylic acid cyclohexyl-ethyl-amide | cyclohexyl-ethyl-amine | 2-chloro-boronic acid | Method E |
| 124 | 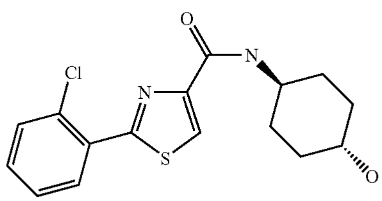 | 336 | 2-(2-Chloro-phenyl)-thiazole-4-carboxylic acid (4-hydroxy-cyclohexyl)-amide | 4-hydroxy-cyclohexyl-amine | 2-chloro-boronic acid | Method E |
| 125 | 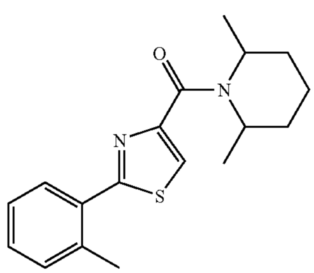 | 314 | (2,6-Dimethyl-piperidin-1-yl)-(2-o-tolyl-thiazol-4-yl)-methanone | 2,6-dimethyl-piperidine | 2-methyl-phenyl-boronic acid | Method F |
| 126 | 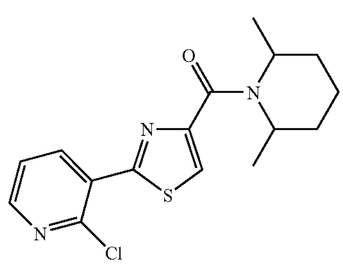 | 336 | [2-(2-Chloro-pyridin-3-yl)-thiazol-4-yl]-(2,6-dimethyl-piperidin-1-yl)-methanone | 2,6-dimethyl-piperidine | 2-chloro-3-pyridyl-boronic acid | Method F |
| 127 | 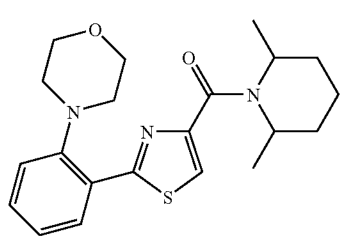 | 385 | (2,6-Dimethyl-piperidin-1-yl)-[2-(2-morpholin-4-yl-phenyl)-thiazol-4-yl]-methanone | 2,6-dimethyl-piperidine | 2-morpholin-4-yl-phenyl boronic acid | Method F |
| 128 | 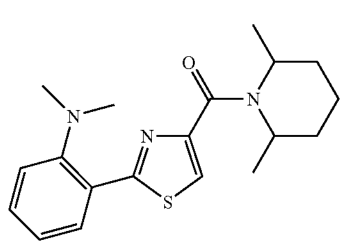 | 343 | [2-(2-Dimethyl-amino-phenyl)-thiazol-4-yl]-(2,6-dimethyl-piperidin-1-yl)-methanone | 2,6-dimethyl-piperidine | 2-dimethylamino-phenyl-boronic acid | Method F |

-continued

| Ex. # | Structure | Mass ES(+) | Systematic Name | Amine Reagent | Other Reagent | Method |
|---|---|---|---|---|---|---|
| 129 | 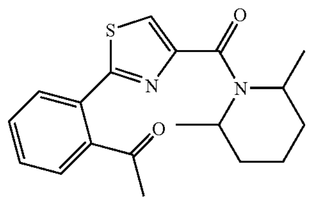 | 342 | 1-{2-[4-(2,6-Dimethyl-piperidine-1-carbonyl)-thiazol-2-yl]-phenyl}-ethanone | 2,6-dimethyl-piperidine | 2-acetyl-phenyl-boronic acid | Method E |
| 130 | 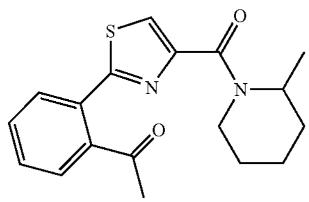 | 328 | 1-{2-[4-(2-Methyl-piperidine-1-carbonyl)-thiazol-2-yl]-phenyl}-ethanone | 2-methyl piperidine | 2-acetyl-phenyl-boronic acid | Method E |
| 131 | 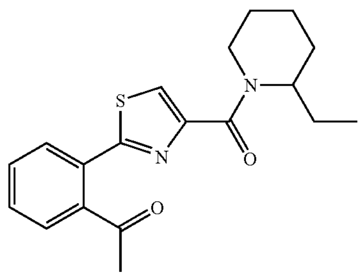 | 342 | 1-{2-[4-(2-Ethyl-piperidine-1-carbonyl)-thiazol-2-yl]-phenyl}-ethanone | 2-ethyl-piperidine | 2-acetyl-phenyl-boronic acid | Method E |
| 132 | 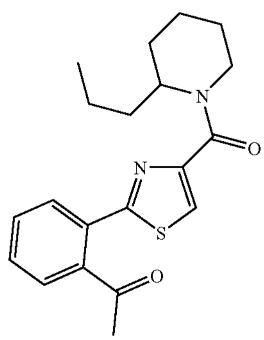 | 356 | 1-{2-[4-(2-Propyl-piperidine-1-carbonyl)-thiazol-2-yl]-phenyl}-ethanone | 2-propyl-piperidine | 2-acetyl-phenyl-boronic acid | Method E |
| 133 | 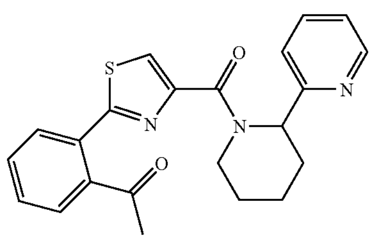 | 391 | 1-{2-[4-(3,4,5,6-Tetrahydro-2H-[2,2']bipyridinyl-1-carbonyl)-thiazol-2-yl]-phenyl}-ethanone | 1,2,3,4,5,6-hexahydro-[2,2']bipyridinyl | 2-acetyl-phenyl-boronic acid | Method E |
| 134 | Chiral | 391 | 1-{2-[4-((S)-3,4,5,6-Tetrahydro-2H-[2,2']bipyridinyl-1-carbonyl)-thiazol-2-yl]-phenyl}-ethanone | (S)-1,2,3,4,5,6-hexahydro-[2,2']bipyridinyl | 2-acetyl-phenyl-boronic acid | Method E |

-continued

| Ex. # | Structure | Mass ES(+) | Systematic Name | Amine Reagent | Other Reagent | Method |
|---|---|---|---|---|---|---|
| 135 | 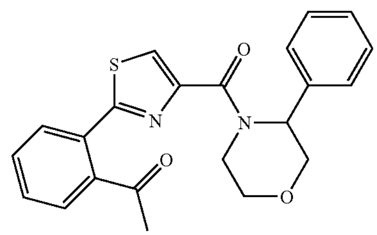 | 392 | 1-{2-[4-(3-Phenyl-morpholine-4-carbonyl)-thiazol-2-yl]-phenyl}-ethanone | 3-phenyl-morpholine | 2-acetyl-phenyl-boronic acid | Method E |
| 136 | 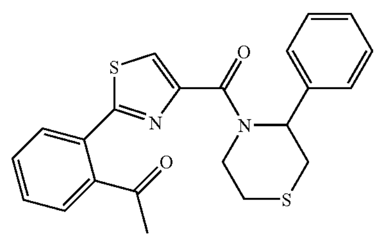 | 408 | 1-{2-[4-(3-Phenyl-thiomorpholine-4-carbonyl)-thiazol-2-yl]-phenyl}-ethanone | 3-phenyl-thiomorpholine | 2-acetyl-phenyl-boronic acid | Method E |
| 137 | 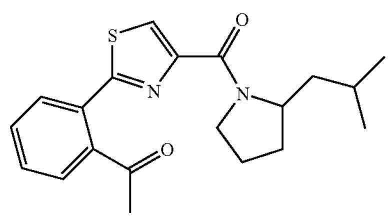 | 356 | 1-{2-[4-(2-Isobutyl-pyrrolidine-1-carbonyl)-thiazol-2-yl]-phenyl}-ethanone | 2-isobutyl-pyrrolinde | 2-acetyl-phenyl-boronic acid | Method E |
| 138 | 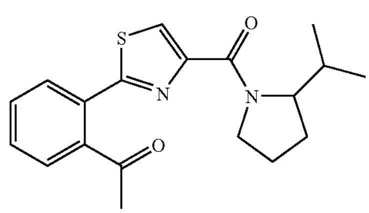 | 342 | 1-{2-[4-(2-Isopropyl-pyrrolidine-1-carbonyl)-thiazol-2-yl]-phenyl}-ethanone | 2-isobutyl-pyrrolinde | 2-acetyl-phenyl-boronic acid | Method E |
| 139 | 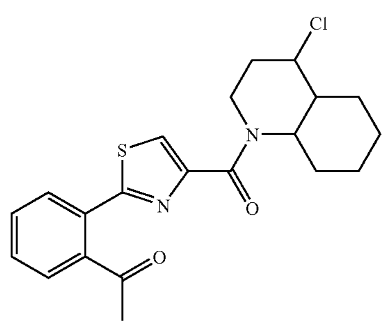 | 402 | 1-{2-[4-(4-Chloro-octahydro-quinoline-1-carbonyl)-thiazol-2-yl]phenyl}-ethanone | 4-chlorodecahydro-quinoline | 2-acetyl-phenyl-boronic acid | Method E |
| 140 | 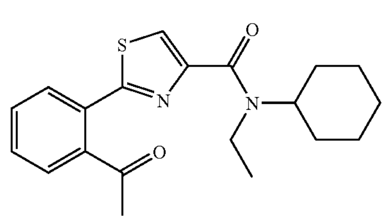 | 356 | 2-(2-Acetyl-phenyl)-thiazole-4-carboxylic acid cyclohexyl-ethyl-amide | cyclohexyl-ethyl-amine | 2-acetyl-phenyl-boronic acid | Method E |

-continued

| Ex. # | Structure | Mass ES(+) | Systematic Name | Amine Reagent | Other Reagent | Method |
|---|---|---|---|---|---|---|
| 141 | 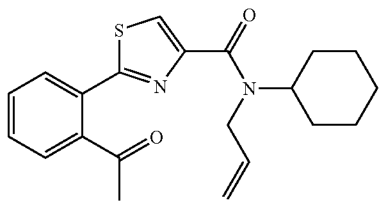 | 368 | 2-(2-Acetyl-phenyl)-thiazole-4-carboxylic acid allyl-cyclohexyl-amide | allyl-cyclohexyl-amine | 2-acetyl-phenyl-boronic acid | Method E |
| 142 | 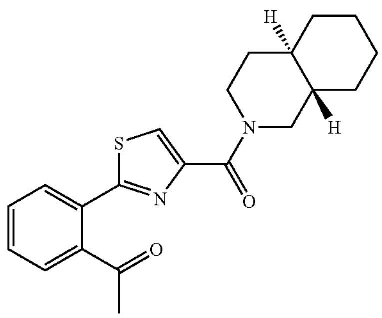 | 368 | 1-{2-[4-((trans)-Octahydro-isoquinoline-2-carbonyl)-thiazol-2-yl]-phenyl}-ethanone | trans-decahydro-isoquinoline | 2-acetyl-phenyl-boronic acid | Method E |
| 143 | 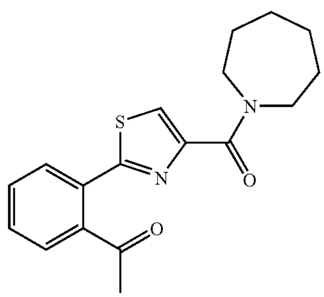 | 328 | 1-{2-[4-(Azepane-1-carbonyl)-thiazol-2-yl]-phenyl}-ethanone | azepane | 2-acetyl-phenyl-boronic acid | Method E |
| 144 | 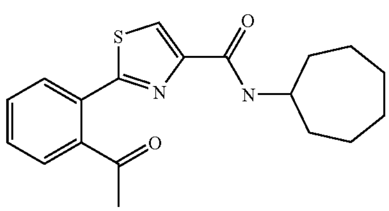 | 342 | 2-(2-Acetyl-phenyl)-thiazole-4-carboxylic acid cycloheptyl amide | Cycloheptyl amine | 2-acetyl-phenyl-boronic acid | Method E |
| 145 | 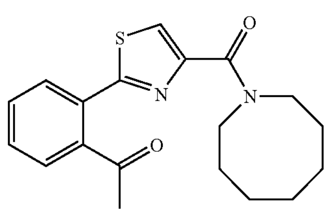 | 342 | 1-{2-[4-(Azocane-1-carbonyl)-thiazol-2-yl]-phenyl}-ethanone | azocane | 2-acetyl-phenyl-boronic acid | Method E |
| 146 | 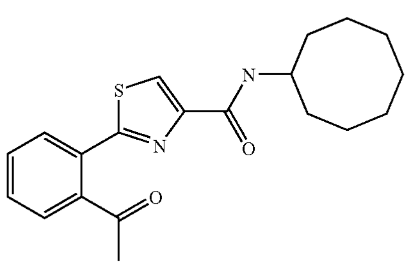 | 356 | 2-(2-Acetyl-phenyl)-thiazole-4-carboxylic acid cyclo-octylamide | Cyclooctyl amine | 2-acetyl-phenyl-boronic acid | Method E |

-continued

| Ex. # | Structure | Mass ES(+) | Systematic Name | Amine Reagent | Other Reagent | Method |
|---|---|---|---|---|---|---|
| 147 | 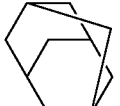 | 380 | 2-(2-Acetyl-phenyl)-thiazole-4-carboxylic acid adamantan-1-ylamide | adamantan-1-ylamine | 2-acetyl-phenyl-boronic acid | Method E |
| 148 | 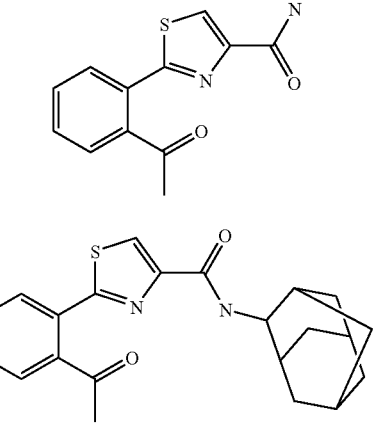 | 380 | 2-(2-Acetyl-phenyl)-thiazole-4-carboxylic acid adamantan-2-ylamide | adamantan-2-ylamine | 2-acetyl-phenyl-boronic acid | Method E |
| 149 | 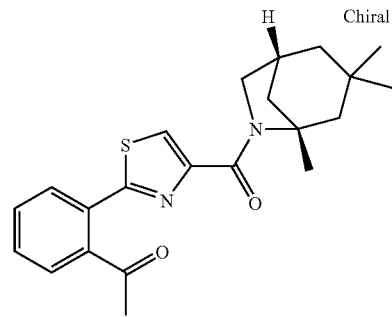 | 382 | 1-{2-[4-((1R,5R)-3,3,5-Trimethyl-6-aza-bicyclo[3.2.1]octane-6-carbonyl)-thiazol-2-yl]-phenyl}-ethanone | 3,3,5-trimethyl-6-aza-bicyclo[3.2.1]octane | 2-acetyl-phenyl-boronic acid | Method E |
| 150 | 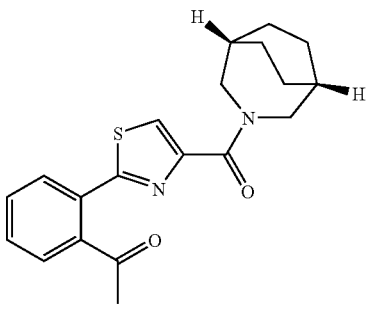 | 354 | 1-{2-[4-(3-Aza-bicyclo[3.2.2]nonane-3-carbonyl)-thiazol-2-yl]phenyl}-ethanone | 3-aza-bicyclo[3.2.2]nonane | 2-acetyl-phenyl-boronic acid | Method E |
| 151 | 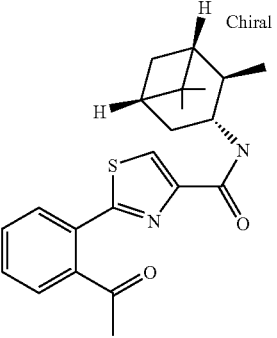 | 382 | 2-(2-Acetyl-phenyl)-thiazole-4-carboxylic acid ((1R,2R,3R,5S)-2,6,6-trimethyl-bicyclo[3.1.1]hept-3-yl)-amide | 2,6,6-trimethyl-bicyclo[3.1.1]hept-3-ylamine | 2-acetyl-phenyl-boronic acid | Method E |

| Ex. # | Structure | Mass ES(+) | Systematic Name | Amine Reagent | Other Reagent | Method |
|---|---|---|---|---|---|---|
| 152 | 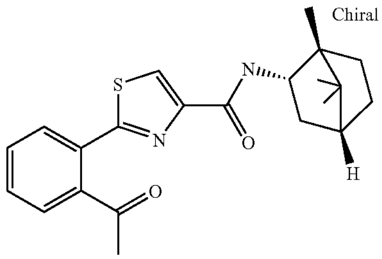 | 382 | 2-(2-Acetyl-phenyl)-thiazole-4-carboxylic acid ((1R,2S,4R)-1,7,7-trimethyl-bicyclo[2.2.1]hept-2-yl)-amide | 1,7,7-trimethyl-bicyclo[2.2.1]hept-2-ylamine | 2-acetyl-phenyl-boronic acid | Method E |
| 153 | 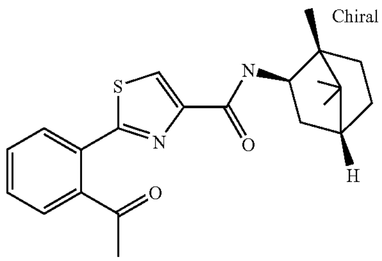 | 382 | 2-(2-Acetyl-phenyl)-thiazole-4-carboxylic acid ((1R,2R,4R)-1,7,7-trimethyl-bicyclo[2.2.1]hept-2-yl)-amide | 1,7,7-Trimethyl-bicyclo[2.2.1]hept-2-ylamine | 2-acetyl-phenyl-boronic acid | Method E |
| 154 | 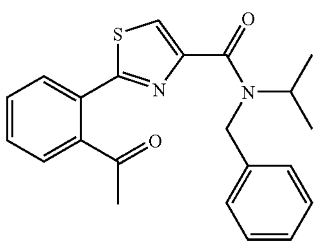 | 378 | 2-(2-Acetyl-phenyl)-thiazole-4-carboxylic acid benzyl-isopropyl-amide | benzyl-isopyropyl-amine | 2-acetyl-phenyl-boronic acid | Method E |
| 155 | 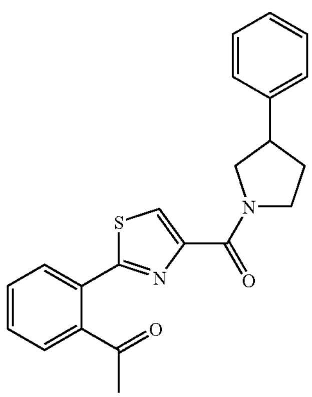 | 376 | 1-{2-[4-(3-Phenyl-pyrrolidine-1-carbonyl)-thiazol-2-yl]-phenyl}-ethanone | 3-phenyl-pyrrolidine | 2-acetyl-phenyl-boronic acid | Method E |
| 156 | 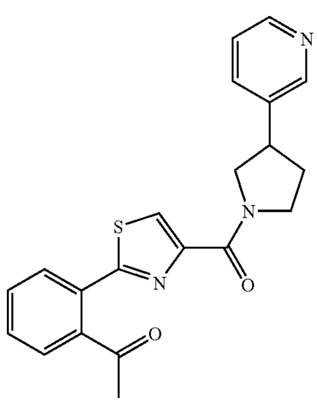 | 377 | 1-{2-[4-(3-Pyridin-3-yl-pyrrolidine-1-carbonyl)-thiazol-2-yl]-phenyl}-ethanone | 3-pyridin-3-yl-pyrrolidine | 2-acetyl-phenyl-boronic acid | Method E |

| Ex. # | Structure | Mass ES(+) | Systematic Name | Amine Reagent | Other Reagent | Method |
|---|---|---|---|---|---|---|
| 157 | 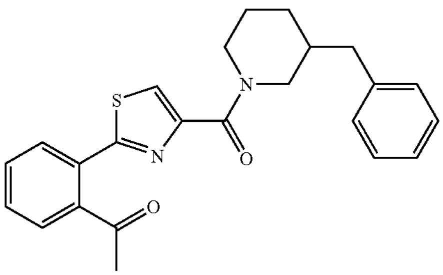 | 404 | 1-{2-[4-(3-Benzyl-piperidine-1-carbonyl)-thiazol-2-yl]-phenyl}-ethanone | 3-benzyl-piperidine | 2-acetyl-phenyl-boronic acid | Method E |
| 158 | 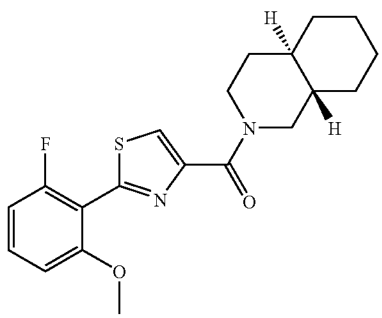 | 374 | [2-(2-Fluoro-6-methoxy-phenyl)-thiazol-4-yl]-(octahydro-isoquinolin-2-yl)-methanone | trans-decahydro-isoquinoline | 2-fluoro-6-methoxyphenyl boronic acid | Method E |
| 159 | 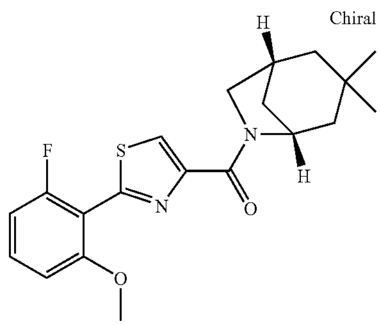 | 388 | [2-(2-Fluoro-6-methoxy-phenyl)-thiazol-4-yl]-((1R,5R)-3,3,5-trimethyl-6-aza-bicyclo[3.2.1]oct-6-yl)-methanone | 3,3,5-trimethyl-6-aza-bicyclo[3.2.1]octane | 2-fluoro-6-methoxyphenyl boronic acid | Method E |
| 160 | 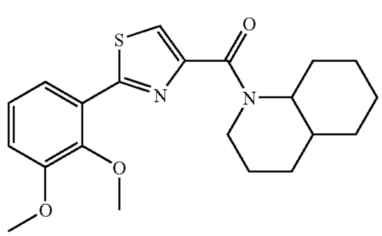 | 386 | [2-(2,3-Dimethoxy-phenyl)-thiazol-4-yl]-(octahydro-quinolin-1-yl)-methanone | decahydro-quinoline | 2,3-dimethoxy-phenyl-boronic acid | Method E |
| 161 | 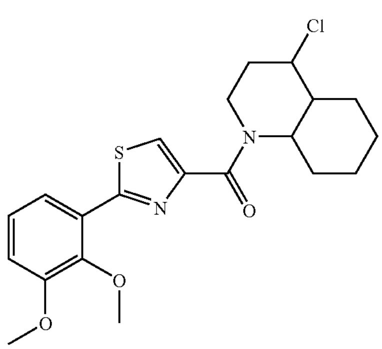 | 420 | (4-Chloro-octahydro-quinolin-1-yl)-[2-(2,3-dimethoxy-phenyl)-thiazol-4-yl]-methanone | 4-chlorodecahydro-quinoline | 2,3-dimethoxy-phenyl-boronic acid | Method E |

| Ex. # | Structure | Mass ES(+) | Systematic Name | Amine Reagent | Other Reagent | Method |
|---|---|---|---|---|---|---|
| 162 | 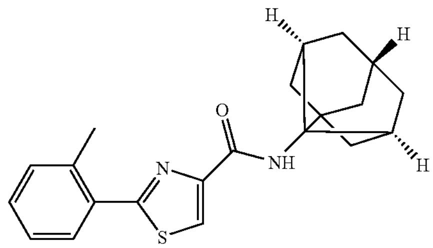 | 352 | 2-o-Tolyl-thiazole-4-carboxylic acid adamantan-2-ylamide | adamantan-2-ylamine | 2-Methylphenyl-boronic acid | Method E |
| 163 | 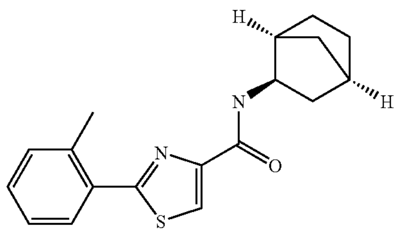 | 312 | 2-o-Tolyl-thiazole-4-carboxylic acid (1S,2R,4R)-bicyclo[2.2.1]hept-2-ylamide | 1,7,7-trimethyl-bicyclo[2.2.1]hept-2-ylamine | 2-Methylphenyl-boronic acid | Method E |
| 164 | 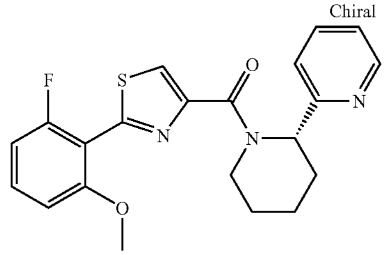 | 397 | [2-(2-Fluoro-6-methoxy-phenyl)-thiazol-4-yl]-(S)-3,4,5,6-tetrahydro-2H-[2,2']bipyridinyl-1-yl-methanone | (S)-3,4,5,6-tetrahydro-2H-[2,2']bipyridine | 2-fluoro-6-methoxy-phenyl-boronic acid | Method E |
| 165 | 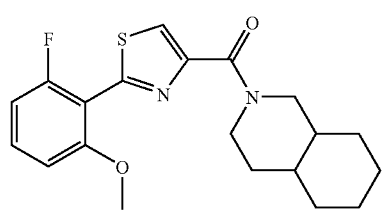 | 374 | [2-(2-Fluoro-6-methoxy-phenyl)-thiazol-4-yl]-(octahydro-isoquinolin-2-yl)-methanone | decahydro-isoquinoline | 2-fluoro-6-methoxy-phenyl-boronic acid | Method E |
| 166 | 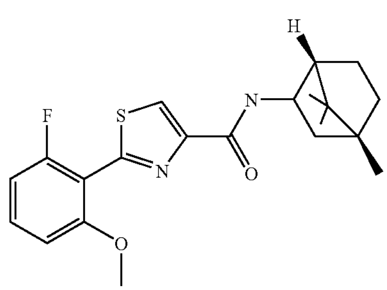 | 388 | 2-(2-Fluoro-6-methoxy-phenyl)-thiazole-4-carboxylic acid ((1R,4R)-4,7,7-trimethyl-bicyclo[2.2.1]hept-2-yl)-amide | 4,7,7-trimethyl-bicyclo[2.2.1]hept-2-ylamine | 2-fluoro-6-methoxy-phenyl-boronic acid | Method E |

| Ex. # | Structure | Mass ES(+) | Systematic Name | Amine Reagent | Other Reagent | Method |
|---|---|---|---|---|---|---|
| 167 | 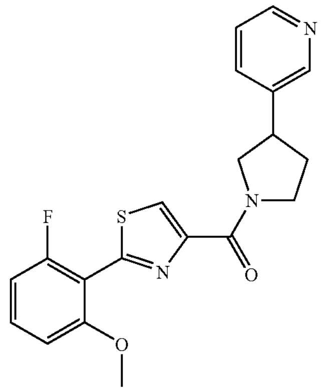 | 383 | [2-(2-Fluoro-6-methoxy-phenyl)-thiazol-4-yl]-(3-pyridin-3-yl-pyrrolidin-1-yl)-methanone | 3-pyridin-3-yl-pyrrolidine | 2-fluoro-6-methoxy-phenyl-boronic acid | Method E |
| 168 | 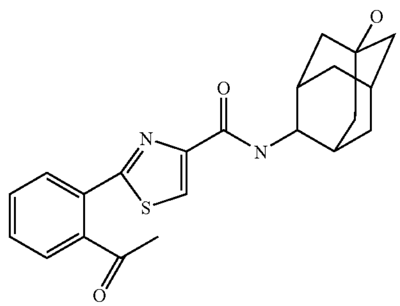 | 396 | 2-(2-Acetyl-phenyl)-thiazole-4-carboxylic acid (5-hydroxy-adamantan-2-yl)-amide | 5-hydroxy-adaman-ylamine | 2-Acetyl-phenyl-boronic acid | Method E |
| 169 | 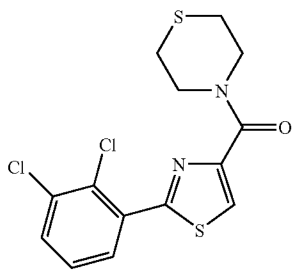 | 358 | [2-(2,3-Dichloro-phenyl)-thiazol-4-yl]-thiomorpholin-4-yl-methanone | Thiomorpholine | 2-(2,3-Dichloro-phenyl)-thiazole-4-carboxylic acid | Method D |
| 170 | 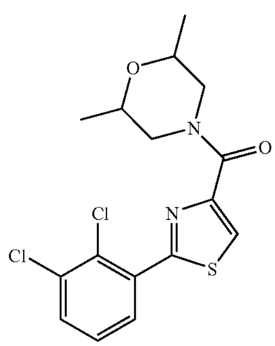 | 370 | [2-(2,3-Dichloro-phenyl)-thiazol-4-yl]-(2,6-dimethyl-morpholin-4-yl)-methanone | 2,6-dimethyl morpholine | 2-(2,3-Dichloro-phenyl)-thiazole-4-carboxylic acid | Method D |
| 171 | 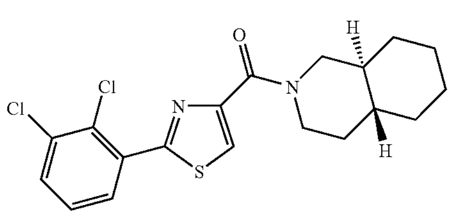 | 394 | [2-(2,3-Dichloro-phenyl)-thiazol-4-yl]-(4aR,8aS)-octahydro-isoquinolin-2-yl-methanone | Decahydro-isoquinoline (trans) | 2-(2,3-Dichloro-phenyl)-thiazole-4-carboxylic acid | Method B |

-continued

| Ex. # | Structure | Mass ES(+) | Systematic Name | Amine Reagent | Other Reagent | Method |
|---|---|---|---|---|---|---|
| 172 | Chiral | 408 | 2-(2,3-Dichloro-phenyl)-thiazole-4-carboxylic acid ((1R,2R,3R,5S)-2,6,6-trimethyl-bicyclo[3.1.1]hept-3-yl)-amide | (−)-Isopino campheylamine | 2-(2,3-Dichloro-phenyl)-thiazole-4-carboxylic acid | Method B |
| 173 | 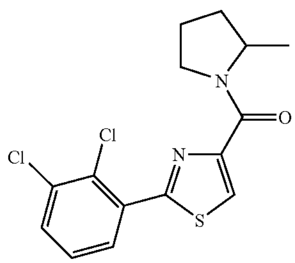 | 340 | [2-(2,3-Dichloro-phenyl)-thiazol-4-yl]-(2-methyl-pyrrolidin-1-yl)-methanone | 2-Methyl-pyrrolidine | 2-(2,3-Dichloro-phenyl)-thiazole-4-carboxylic acid | Method B |
| 174 | 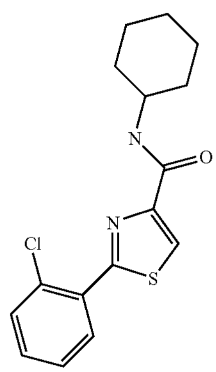 | 320 | 2-(2-Chloro-phenyl)-thiazole-4-carboxylic acid cyclo-hexylamide | Cyclohexyl amine | 2-(2-Chloro-phenyl)-thiazole-4-carboxylic acid | Method D |
| 175 | 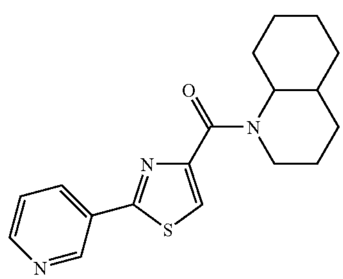 | 327 | (Octahydro-quinolin-1-yl)-(2-pyridin-3-yl-thiazol-4-yl)-methanone | Decahydro-quinoline | 2-(3-Pyridyl)-1,3-thiazole-4-carboxylic acid (Maybridge) | Method A |
| 176 | 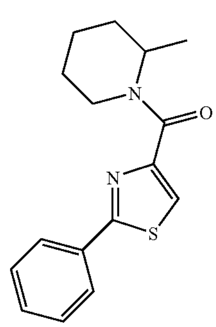 | 286 | (2-Methyl-piperidin-1-yl)-(2-phenyl-thiazol-4-yl)-methanone | 2-Methyl-piperidine | 2-Phenyl-thiazole-4-carboxylic acid | Method D |

-continued

| Ex. # | Structure | Mass ES(+) | Systematic Name | Amine Reagent | Other Reagent | Method |
|---|---|---|---|---|---|---|
| 177 | 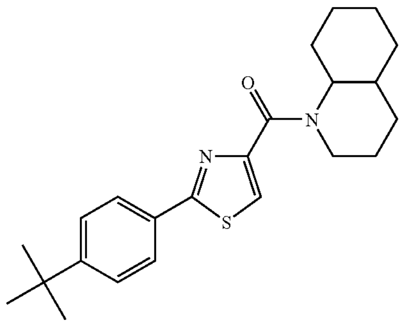 | 382 | [2-(4-tert-Butyl-phenyl)-thiazol-4-yl]-(octahydro-quinolin-1-yl)-methanone | Decahydro-quinoline | 2-(4-tert-Butyl-phenyl)-thiazole-4-carboxylic acid | Method D |
| 178 | 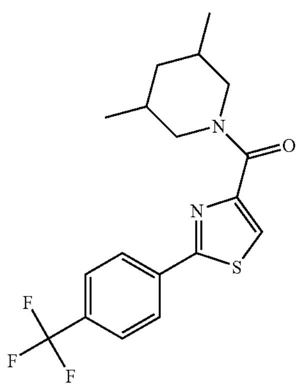 | 368 | (3,5-Dimethyl-piperidin-1-yl)-[2-(4-trifluoromethyl-phenyl)-thiazol-4-yl]-methanone | 3,5-Dimethyl-piperidine | 2-(4-Trifluoromethyl-phenyl)-thiazole-4-carboxylic acid | Method D |
| 179 | 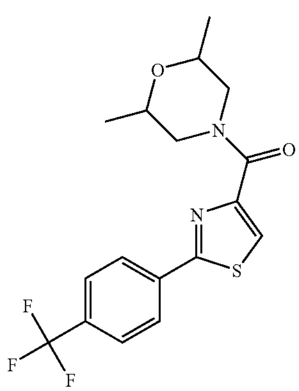 | 370 | (2,6-Dimethyl-morpholin-4-yl)-[2-(4-trifluoromethyl-phenyl)-thiazol-4-yl]-methanone | 2,6-Dimethyl-morpholine | 2-(4-Trifluoromethyl-phenyl)-thiazole-4-carboxylic acid | Method D |

-continued

| Ex. # | Structure | Mass ES(+) | Systematic Name | Amine Reagent | Other Reagent | Method |
|---|---|---|---|---|---|---|
| 180 | 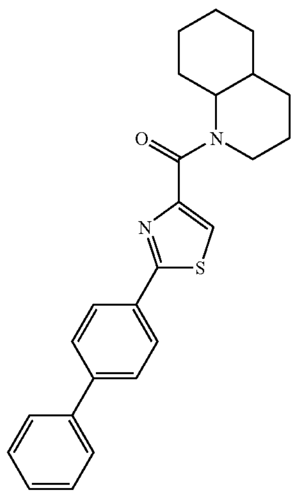 | 402 | (2-Biphenyl-4-yl-thiazol-4-yl)-(octahydro-quinolin-1-yl)-methanone | Decahydro-quinoline | 4-Biphenyl-boronic acid | Method F |
| 181 | 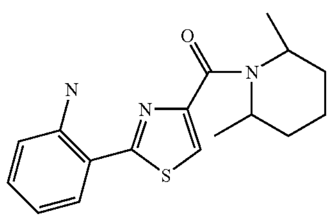 | 315 | [2-(2-Amino-phenyl)-thiazol-4-yl]-(2,6-dimethyl-piperidin-1-yl)-methanone | 2,6-Dimethyl-piperidine | 2-Amino-phenyl-boronic acid | Method E* |
| 182 | 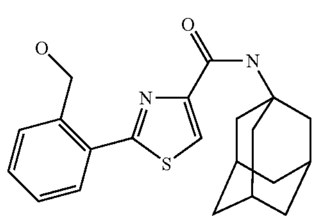 | 368 | 2-(2-Hydroxymethyl-phenyl)-thiazole-4-carboxylic acid adamantan-1-ylamide | 1-Amino-adamantane | 2-Hydroxymethyl-phenyl-boronic acid | Method E |
| 183 | 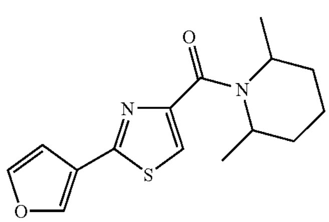 | 290 | (2,6-Dimethyl-piperidin-1-yl)-(2-furan-3-yl-thiazol-4-yl)-methanone | 2,6-Dimethyl-piperidine | 2-Bromo-thiazole-4-carboxylic acid | Method F |
| 184 | 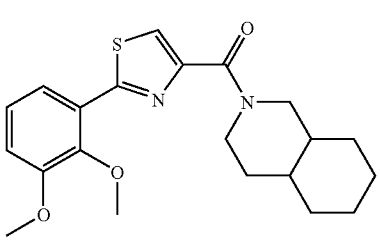 | 386 | [2-(2,3-Dimethoxy-phenyl)-thiazol-4-yl]-(octahydro-isoquinolin-2-yl)-methanone | Decahydro-isoquinoline | 2,3-Dimethoxy-phenyl-boronic acid | Method E |

| Ex. # | Structure | Mass ES(+) | Systematic Name | Amine Reagent | Other Reagent | Method |
|---|---|---|---|---|---|---|
| 185 | 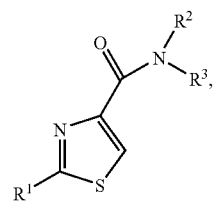 | 396 | 1-{2-[4-(3-Cyclohexyl-piperidine-1-carbonyl)-thiazol-2-yl]-phenyl}-ethanone | 3-Cyclohexyl-piperidine hydrochloride | 2-Acetyl-phenyl-boronic acid | Method E |

*In Example 181, the aniline nitrogen was protected as the bis-Boc derivative following the Suzuki reaction, and the Boc groups were removed using trifluoroacetic acid in dichloromethane following the saponification and amide coupling reactions.

Example 186

Testing of Compounds of the Invention

The in vitro inhibition of 11β-HSD1 by compounds of the present invention was demonstrated as follows:

Purified human HSD1 was diluted in 50 mM Tris-HCl, 100 mM NaCl, 0.1 mg/mL BSA, 0.02% Lubrol, 20 mM MgCl2, 10 mM glucose 6-phosphate, 0.4 mM NADPH, 60 U/mL glucose 6-phosphate dehydrogenase to a concentration of 1.5 μg/mL (Enzyme Solution). Cortisone (100 μM) in DMSO was diluted to 1 μM with 50 mM Tris-HCl, 100 mM NaCl (Substrate Solution). Test compounds (40 μM) in DMSO were diluted 3 fold in series in DMSO and further diluted 20 fold in Substrate Solution. Enzyme Solution (10 μL/well) was added into 384 well microtiter plates followed by diluted compound solutions (10 μL/well) and mixed well. Samples were then incubated at 37° C. for 30 min. EDTA/biotin-cortisol solution (10 μL/well) in 28 mM EDTA, 100 nM biotin-cortisol, 50 mM Tris-HCl, 100 mM NaCl was then added followed by 5 μL/well of anti-cortisol antibody (3.2 μg/mL) in 50 mM Tris-HCl, 100 mM NaCl, 0.1 mg/mL BSA and the solution was incubated at 37° C. for 30 min. Five μL per well of Eu-conjugated anti-mouse IgG (16 nM) and APC-conjugated streptavidin (160 nM) in 50 mM Tris-HCl, 100 mM NaCl, 0.1 mg/mL BSA was added and the solution was incubated at room temperature for 2 hours. Signals were quantitated by reading time-resolved fluorescence on a Victor 5 reader (Wallace).

Percent inhibition of HSD1 activity by an agent at various concentrations was calculated by the following formula:

% Inhibition=100*[1−(Fs−Fb)/(Ft−Fb)], wherein:
Fs is the fluorescence signal of the sample which included the agent,
Fb is the fluorescence signal in the absence of HSD1 and agent,
Ft is the fluorescence signal in the presence of HSD1, but no agent.

The inhibitory activities of test compounds were determined by the $IC_{50}$s, or the concentration of compound that gave 50% inhibition.

Results obtained by the foregoing test using a representative number of compounds of formula I as the test compounds are shown in the following table:

| Example # | Enzyme Assay IC50 (μM) |
|---|---|
| Example 10 | 0.05 |
| Example 17 | 0.373 |
| Example 33 | 0.365 |
| Example 46 | 0.102 |
| Example 61 | 0.457 |
| Example 96 | 0.04 |
| Example 115 | 0.34 |
| Example 117 | 1.5 |
| Example 119 | 0.73 |
| Example 124 | 1.9 |
| Example 144 | 0.032 |
| Example 180 | 0.93 |

It is to be understood that the invention is not limited to the particular embodiments of the invention described above, as variations of the particular embodiments may be made and still fall within the scope of the appended claims.

What is claimed is:
1. A compound of the formula (I):

(I)

wherein:
$R^1$ is benzofuran, cyclopentene, cyclohexene, cycloheptene, benzo[1,3]dioxole, indole or phenyl, wherein said phenyl is unsubstituted or mono-, bi-, or tri-substituted independently with halogen, lower alkyl, halo-lower-alkyl, phenyl, —$OCH_3$, —$O(CH_2)nCH_3$, —$(CH_2)nOH$, —OH, —$NH_2$, —$OCF_3$, —$O(CH_2)$n-phenyl, —$SCH_3$, —$NHSO_2CH_3$, thiophene, morpholine, —$C(O)CH_3$, —$N(CH_3)_2$ or —$NO_2$;
one of $R^2$ or $R^3$ is cyclohexane and the other is alkyl or allyl, or
$R^2$ and $R^3$, together with the N atom to which they are attached, is decahydroquinoline, azocane, azepane, pipendine, morpholine, adamantane, thiomorpholine, cyclooctane, cyclohepane, pyrrolidine, decahydroisoauinoline, azepane-4-one, hydroxyadaman-ylamine, azabicyclo[3.2.2.]nonane, bicycle[2.2.1]hept-2-ylamine, hexahydro[3.2-c]quinoline, bicycle[3.1.1]heptane or azabicyclo[3.2.1]octane;

or a pharmaceutically acceptable salt thereof, with the proviso that the following compounds are excluded:

[2-(2,3-Dihydro-benzo[1,4]dioxin-2-yl)-thiazol-4-yl]-pyrrolidin-1-yl-methanone;

[2-(2,3-Dihydro-benzo[1,4]dioxin-2-yl)-thiazol-4-yl]-morpholin-4-yl-methanone;

(4-Phenyl-3,6-dihydro-2H-pyridin-1-yl)-(2-phenyl-thiazol-4-yl)-methanone;

(2-Benzo[1,2,5]oxadiazol-5-yl-thiazol-4-yl)-morpholin-4-yl-methanone;

Morpholin-4-yl-(2-pyridin-3-yl-thiazol-4-yl)-methanone

[2-(4-Methyl-pyridin-3-yl)-thiazol-4-yl]-pipendin-1-yl-methanone;

[2-(4-Methyl-pyridin-3-yl)-thiazol-4-yl]-morpholin-4-yl-methanone;

[2-(5-Methyl-isoxazol-3-yl)-thiazol-4-yl]-pipendin-1-yl-methanone; and

[2-(3-Methyl-5-trifluoromethyl-pyrazol-1-yl)-thiazol-4-yl]-morpholin-4-yl-methanone.

2. The compound according to claim 1, wherein $R^1$ is phenyl.

3. The compound according to claim 1, wherein $R^1$ is phenyl mono- or bi-substituted with halogen, alkyl, lower alkoxy, —SCH$_3$ or —C(O)CH$_3$.

4. The compound according to claim 1, wherein said compound is azocan-1-yl-[2-(2,3-dichloro-phenyl)-thiazol-4-yl]-methanone.

5. The compound according to claim 1, wherein said compound is [2-(3-chloro-phenyl)-thiazol-4-yl]-(octahydro-quinolin-1-yl)-methanone.

6. The compound according to claim 1, wherein said compound is [2-(3-methylsulfanyl-phenyl)-thiazol-4-yl]-(octahydro-quinolin-1-yl)-methanone.

7. The compound according to claim 1, wherein said compound is (2-phenyl-thiazol -4-yl)-((1R,5R)-3,3,5-trimethyl-6-aza-bicyclo[3.2.1]oct-6-yl)-methanone.

8. The compound according to claim 1, wherein said compound is 1-{2-[4-(2-isopropyl-pyrrolidine-1-carbonyl)-thiazol-2-yl]-phenyl}-ethanone.

9. The compound according to claim 1, wherein said compound is 2-(2-acetyl-phenyl)-thiazole-4-carboxylic acid cyclooctylamide.

10. The compound according to claim 1, wherein said compound is 2-(2-acetyl-phenyl)-thiazole-4-carboxylic acid adamantan-2-ylamide.

11. The compound according to claim 1, wherein said compound is 1-{2-[4-((1R,5R)-3,3,5-trimethyl-6-aza-bicyclo[3.2.1]octane-6-carbonyl)-thiazol-2-yl]-phenyl}-ethanone.

12. The compound according to claim 1, wherein said compound is 2-(2-acetyl-phenyl)-thiazole-4-carboxylic acid ((1R,2R,3R,5S)-2,6,6-trimethyl-bicyclo[3.1.1]hept-3-yl)-amide.

13. The compound according to claim 1, wherein said compound is [2-(2-fluoro-6-methoxy-phenyl)-thiazol-4-yl]-((1R,5R)-3,3,5-trimethyl-6-aza-bicyclo[3.2.1]oct-6-yl)-methanone.

14. The compound according to claim 1, wherein said compound is 2-o-tolyl-thiazole-4-carboxylic acid adamantan-2-ylamide.

15. The compound according to claim 1, wherein said compound is 2-(2-Acetyl-phenyl)-thiazole-4-carboxylic acid (5-hydroxy-adamantan-2-yl)-amide.

16. A pharmaceutical composition, comprising a therapeutically effective amount of a compound according to claim 1 or a pharmaceutically acceptable salt thereof, and a pharmaceutically acceptable carrier.

17. A method for treating type II diabetes mellitus or metabolic syndrome, comprising the step of administering to a patient in need thereof a therapeutically effective amount of a compound according to claim 1.

* * * * *

UNITED STATES PATENT AND TRADEMARK OFFICE
CERTIFICATE OF CORRECTION

PATENT NO. : 7,645,773 B2
APPLICATION NO. : 11/650645
DATED : January 12, 2010
INVENTOR(S) : Paul Gillespie et al.

It is certified that error appears in the above-identified patent and that said Letters Patent is hereby corrected as shown below:

In Claim 1, Column 118, Line 65, delete "decahydroguinoline" and insert --decahydroquinoline--

In Claim 1, Column 118, Line 66, delete "pipendine" and insert --piperidine--

In Claim 1, Column 118, Line 67, delete "cyclohepane" and insert --cycloheptane--

In Claim 1, Column 119, Line 1, delete "soauinoline" and insert --soquinoline--

In Claim 1, Column 119, Line 17, delete "pipendin" and insert --piperidin--

In Claim 1, Column 119, Line 22, delete "pipendin" and insert --piperidin--

Signed and Sealed this

Twenty-fifth Day of May, 2010

David J. Kappos
*Director of the United States Patent and Trademark Office*